US008530226B2

(12) United States Patent (10) Patent No.: US 8,530,226 B2
Festel et al. (45) Date of Patent: Sep. 10, 2013

(54) FERMENTATIVE PRODUCTION OF ISOBUTANOL WITH YEAST

(75) Inventors: Gunter Festel, Fürigen (CH); Eckhard Boles, Darmstadt (DE); Christian Weber, Kelkheim am Taunus (DE); Dawid Brat, Frankfurt am Main (DE)

(73) Assignee: Butalco GmbH, Hunenberg/Zug (CH)

( * ) Notice: Subject to any disclaimer, the term of this patent is extended or adjusted under 35 U.S.C. 154(b) by 54 days.

(21) Appl. No.: 12/918,722

(22) PCT Filed: Feb. 19, 2009

(86) PCT No.: PCT/EP2009/001191
§ 371 (c)(1),
(2), (4) Date: Nov. 8, 2010

(87) PCT Pub. No.: WO2009/103533
PCT Pub. Date: Aug. 27, 2009

(65) Prior Publication Data
US 2011/0053235 A1 Mar. 3, 2011

(30) Foreign Application Priority Data
Feb. 20, 2008 (DE) .......................... 10 2008 010 121

(51) Int. Cl.
*C12N 1/16* (2006.01)
*C12N 1/18* (2006.01)
*C12P 7/16* (2006.01)

(52) U.S. Cl.
USPC .................. 435/255.1; 435/255.2; 435/255.4; 435/160

(58) Field of Classification Search
None
See application file for complete search history.

(56) References Cited

U.S. PATENT DOCUMENTS
2007/0092957 A1* 4/2007 Donaldson et al. ........... 435/157

OTHER PUBLICATIONS

Maniatis, T., Fritsch, E.F., Sambrook, J., "Molecular Cloning A Laboratory Manual", Cold Spring Harbor Laboratory Press, 1982, pp. 1-15, 55-62, 68-73, 86-185, 249-255, 363-401, 435-520.
S. Atsumi et al., Non-Fermentative Pathways for Synthesis of Branch-Chain Higher Alcohols As Biofuels, Nature Publishing Group, vol. 451, No. 3, (2008), pp. 86-90.
J. E. Bailey, Host-Vector Interactions in Escherichia coli, Advances in Biochemical Engineering Biotechnology, vol. 48, (1993), pp. 29-52.
J. Becker et al., A Modified Saccharomyces cerevisiae Strain That Consumes L-Arabinose and Produces Ethanol, Applied and Environmental Microbiology, vol. 69, No. 7, (2003), pp. 4144-4150.
V Biou, et al., The Crystal Struture of Plant Acetohydroxy Acid Isomeroreductase Complexed With NADPH, Two Magnesium Ions and A Herbicidal Transition State Analog Determined At 1.65 Å Resolution, EMBO Journal, vol. 16, No. 12, (1997), pp. 3405-3415.
H. C. Birnboim et al., A Rapid Alkaline Extraction Procedure for Screening Recombinant Plasmid DNA, Nucleic Acids Research, vol. 7. No. 6, (1979), pp. 1513-1523.
E. Boles et al., The Role of the NAD-Dependent Glutamate Dehydrogenase in Restoring Growth on Glucose of a Saccharomyces cerevisiae Phosphoglucose Isomerase Mutant, Eur. J. Biochem, vol. 217, (1993), pp. 469-477.
J. Richard Dickinson et al., An Investigation of the Metabolism of Valine to Isobutyl Alcohol in Saccharomyces cerevisiae, The Journal of Biological Chemistry, vol. 273, No. 40, 1998, pp. 25751-25756.
J. Richard Dickinson et al., The Catabolism of Amino Acids to Long Chain and Complex Alcohols in Saccharomyces cerevisiae, The Journal of Biological Chemistry, vol. 278, No. 10, (2003), pp. 8028-8034.
W. J. Dower et al., High Efficiency Transformation of E. coli by High Voltage Electroporation, Nucleic Acids Research,. vol. 16, No. 13, (1988), pp. 6127-6145.
A Eden et al., Involvement of Branched-Chain Amino Acid Aminotransferases in the Production of Fusel Alcohols During Fermentation in Yeast, Appl. Microbiol Biotechnol, vol. 55, (2001), pp. 296-300.
S. Fillinger et al., Two Glyceraldehydes-3-Phosphate Dehydrogenases With Opposite Physiological Roles in a Nonphotosynthetic Bacterium, The Journal of Biological Chemistry, vol. 275, No. 19, (2000), pp. 14031-14037.
L. Kotula et al., Evaluation of Foreign Gene Codon Optimization in Yeast: Expression of a Mouse IG Kappa Chain, Bio/Technology, Nature Publishing Group, vol. 9, (1991), pp. 1386-1389.
R. D. Gietz et al., High Efficiency Transformation With Lithium Acetate, vol. 8, pp. 121-134, 1998.
F. Omura, Targeting of Mitochondrial Saccharomyces cerevisiae Ilv5p to the Cytosol and Its Effect on Vicinal Diketone Formation in Brewing, Appl. Microbiol Biotechnol, vol. 78, (2008), pp. 503-513.
S. Siew Pang et. al., Expression, Purification, Characterization, and Reconstitution of the Large and Small Subunits of Yeast Acetohydroxyacid Synthase, Biochemistry, American Chemical Society vol. 38, (1999), pp. 5222-5231.
U. Sauer, Evolutionary Engineering of Industrially Important Microbial Phenotypes, Advances in Biochemical Engineering/Biotechnology, vol. 73, (2001), pp. 129-469.
C. Taxis et al., System of Centromeric, Episomal, and Integrative Vectors Based on Drug Resistance Markers for Saccharomyces cerevisiae, Short Technical Reports, Bio Techniques, vol. 40, No. 1, (2006), pp. 73-77.
C. Verduyn et al., Effect of Benzoic Acid on Metabolic Fluxes in Yeasts: A Continuous-Culture Study on the Regulation of Respiration and Alcoholic Fermentation, Published by John Wiley & Sons, Ltd., vol. 8, (1992), pp. 501-517.

(Continued)

*Primary Examiner* — Tekchand Saidha
*Assistant Examiner* — Md. Younus Meah
(74) *Attorney, Agent, or Firm* — RatnerPrestia

(57) ABSTRACT

The invention relates to a yeast cell producing isobutanol, characterized in that the cell has an increased metabolic flow of material from pyruvate and acetolactate, 2,3-dihydroxy isovalerate, 2-ketoisovalerate, isobutyraldehyde to isobutanol, in that at least one of the genes coding the enzymes, which are involved in this conversion, is over-expressed, and without any of said genes being heterologous to said yeast cell, and to a method for the production of isobutanol using yeast cells, comprising the provision of the yeast cells according to the invention, and bringing the yeast cell into contact with a fermentable carbon source.

27 Claims, 2 Drawing Sheets

(56) References Cited

OTHER PUBLICATIONS

K. D. Villa et al., Control of Vicinal Diketone Production by Brewer's Yeast. I. Effects of *ILV5* and *ILV3* Gene Amplification on Vicinal Diketone Production and *ILV* Enzyme Activity, J. Am. Soc. Chem., vol. 53, No. 2, (1995), pp. 49-53.

Z. Vuralhan et al., Identification and Characterization of Phenylpyruvate Decarboxylase Genes in *Saccharomyces cerevisiae*, Applied and Environmental Microbiology, vol. 69, No. 8, (2003), pp. 4534-4541.

R. Wieczorke et al., Concurrent Knock-Out of At Least 20 Transporter Genes Is Required to Block Uptake of Hexoses in *Saccharomyces cerevisiae*, FEBS Letters, 464 (1999), pp. 123-128.

B. Wiedemann et al., Codon-Optimized Bacterial Genes Improved L-Arabinose Fermentation in Recombinant *Saccharomyces cerevisiae*, Applied and Environmental Microbiology, vol. 74, No. 7, (2003), pp. 2043-2050.

R. Wirth, An Alternative Method for Transformation of Bacteria with Plasmid DNA, Genetir, forum Mikrobiologie (1989), pp. 507-515.

F. K. Zimmermann, Procedures Used in the Induction of Mitotic Recombination and Mutation in the Yeast *Saccharomyces cerevisiae*, Mutation Research, vol. 31, (1975), pp. 71-86, Elsevier Scientific Publishing Company, Amsterdam.

Verho et al., Identification of the First Fungal NADP-GAPDH From Kluyveromyces Lactis, Biochemistry, vol. 41, pp. 13833-13838, 2002.

International Search Report dated Jun. 16, 2009.

Goossens et al., "Control of diacetyl formation by intensification of the anabolic flux of acetohydroxy acid intermediates," *Proc. Congr. Eur. Brew. Conv.* vol. 21, p. 553-560, (1987).

Kondo et al., "Genetic engineering to enhance the Ehrlich pathway and alter carbon flux for increased isobutanol production from glucose by *Saccharomyces cerevisiae*"; *Journal of Biotechnology*, vol. 159, p. 32-37 (2012).

Matsuda et al., "Construction of an Artificial Pathway for Isobutanol Biosynthesis in the Cytosol of *Saccharomyces cerevisiae*", *Biosci. Biotechnol. Biochem.*, vol. 76(11), p. 2139-2141 (2012).

Villanueba et al., "Subthreshold Vicinal Diketone Levels in Lager Brewing Yeast Fermentations by Means of ILV5 Gene Amplification," *J. Am. Soc. Brew. Chem.* vol. 48(3), p. 111-114 (1990).

\* cited by examiner

FERMENTATIVE PRODUCTION OF ISOBUTANOL WITH YEAST

CROSS REFERENCE TO RELATED APPLICATIONS

This is a U.S. national application under 35 U.S.C. §371 of International Application No. PCT/EP2009/001191, filed Feb. 19, 2009, which claims priority to German Application No. 10 2008 010 121.4, filed Feb. 20, 2008, the contents of each of which are incorporated by reference in their entirety.

BACKGROUND

The invention relates to a fermentative method of producing isobutanol from sugars.

Isobutanol has excellent properties as fuel. In addition, it is also a useful chemical e.g. as base chemical for the production of other chemicals or as solvent. Today, isobutanol is predominantly produced by petrochemical methods from fossil resources. However, a much more promising prospect would be to produce it from renewable resources such as e.g. vegetable sugars or vegetable waste. Recently, two microbial, non-fermentative methods were presented with which isobutanol can be produced from sugars (Atsumi et al., 2008; US patent application 2007/0092957). In both methods host cells were induced, by the insertion of heterologous DNA, to produce isobutanol and also other branch-chained alcohols from the metabolic intermediate pyruvate, which forms as a result of the breakdown of sugars. However, common to both described methods is that they are non-fermentative, i.e. their redox balances are not equilibrated when sugars break down into isobutanol. They can therefore only be used in complex media by simultaneous conversion of co-substrates, through the formation of by-products or under aerobic conditions. This greatly reduces the practicability of the methods and makes them economically unappealing.

One solution would be the development of a fermentative microbial process which could take place in minimal media, without co-substrates and also under anaerobic or oxygen-limited conditions. In particular yeasts and in particular those of the genus *Saccharomyces* such as e.g. *Saccharomyces cerevisiae* would be suitable as microorganisms. Interestingly, yeasts already have all the enzymes that are necessary for the formation of isobutanol from sugars. However, these enzymes are located in different compartments of the yeast cells (cytosol and mitochondria), they use different co-factors that are not or not effectively convertible into one another ($NAD^+$/NADH and $NADP^+$/NADPH) and the enzymes are expressed only weakly or under special conditions or have a low enzyme activity. In order to achieve an effective production of isobutanol from sugars, the metabolic pathways present would have to be modified such that with their help isobutanol could be produced in redox-neutral manner and with energy gain in the form of ATP, including under anaerobic or oxygen-limited conditions. The development of such a fermentative method of producing isobutanol from sugars is the object and aim of this invention.

Sugars such as e.g. glucose are broken down into pyruvate in host cells such as e.g. yeasts predominantly through the metabolic pathway of glycolysis. Two molecules of pyruvate are produced from one molecule of glucose. In addition, 2 energy-rich compounds are produced in the form of ATP and 2 molecules of $NAD^+$ are reduced to $NADH+H^+$. Pyruvate is then usually converted to ethanol either by the pyruvate decarboxylases and alcohol dehydrogenases or it is transported into the mitochondria, where it is converted into acetyl-CoA by pyruvate dehydrogenase and finally funneled into the citric acid cycle. In addition, pyruvate can also be converted in some other reactions. One of these reaction paths is the biosynthetic pathway to the amino acid valine. On the other hand, however, valine can also be broken down i.a. into the product isobutanol. If the biosynthetic pathway and the catabolic path of valine could be shortened, isobutanol could then be produced direct from sugars via pyruvate. Such a metabolic pathway combines the enzymes which are involved in the biosynthesis of valine (from pyruvate to α-ketoisovalerate) with those which are involved in valine breakdown (from α-ketoisovalerate to isobutanol). The yeast *Saccharomyces cerevisiae* itself contains all the genes required for this. ILV2 (YMR108W) (SEQ. ID. no. 1) encodes the acetolactate synthase which converts two pyruvate molecules into acetolactate. The Ilv2 enzyme (SEQ. ID. no. 2) is activated by the Ilv6 protein (=YCL009C) (SEQ. ID. no. 4). ILV5 (YLR355C) (SEQ. ID. no. 5) encodes the acetohydroxy acid reducto-isomerase which converts acetolactate into 2,3-dihydroxy isovalerate. ILV3 (YJR016C) (SEQ. ID. no. 7) encodes the dihydroxy acid dehydratase which converts 2,3-dihydroxy isovalerate into 2-ketoisovalerate. 2-ketoisovalerate is then usually transaminated into valine; by the transaminases Bat1 (SEQ. ID. no. 10) and Bat2 (SEQ. ID. no. 12). But if this reaction is bypassed or reduced, 2-ketoisovalerate could then also be converted by different 2-keto acid decarboxylases into isobutyraldehyde, e.g. by the enzymes Pdc1 (SEQ. ID. no. 14), Pdc5 (SEQ. ID. no. 16), Pdc6 (SEQ. ID. no. 18), Aro10 (SEQ. ID. no. 20), Thi3 (SEQ. ID. no. 22) (Dickinson et al., 1998; 2003). This direct conversion is usually impeded inter alia by the different compartmentalization of the enzymes (mitochondria, cytosol). Isobutyraldehyde can then finally be reduced to isobutanol by different alcohol dehydrogenases (Dickinson et al., 2003). These include i.a. Adh1-7 (SEQ. ID. no. 24), (SEQ. ID. no. 26), (SEQ. ID. no. 28), (SEQ. ID. no. 30), (SEQ. ID. no. 32), (SEQ. ID. no. 34), (SEQ. ID. no. 36), Sfa1 (SEQ. ID. no. 38), Ypr1 (SEQ. ID. no. 40).

However, most of the named enzymes are not strongly enough expressed or have low levels of enzyme activity for an efficient production of isobutanol from pyruvate or sugars. Another problem is the co-factor specificity and redox balance. During the reduction of the two molecules of pyruvate produced from glycolysis to isobutanol, one molecule of NADPH from the acetohydroxy acid reducto-isomerase and one molecule of NADH or NADPH from the branch-chained alcohol dehydrogenases are required. However, in glycolysis, two molecules of NADH are produced from one molecule of glucose in the glyceraldehyde-3-phosphate dehydrogenase reaction. Thus there is a shortfall of NADPH and an excess of NADH. But NADH is not easily convertible into NADPH. On the other hand, the enzymes Ilv2/Ilv6, Ilv5 (SEQ. ID. no. 6) and Ilv3 (SEQ. ID. no. 8) are at least mainly located in the mitochondria of the yeast cells. The pyruvate must therefore firstly be transported into the mitochondria and finally the 2-ketoisovalerate transported out of the mitochondria into the cytosol. As transport via membranes can often have a limiting effect on flows of material, it would therefore be desirable to shift all reactions into the cytosol. Equally disadvantageous for an efficient production of isobutanol is that some intermediates are drawn off for other metabolic reactions on the way from the sugar to the product. This applies above all to pyruvate which is largely converted to ethanol by the pyruvate decarboxylases and alcohol dehydrogenases. It is therefore important for a more efficient production of isobutanol to reduce or completely eliminate these secondary reactions.

The object and aim of this invention is therefore to provide a fermentative method of producing isobutanol from sugars in which (i) the yeast's own set of enzymes is used for the metabolic pathway from pyruvate to isobutanol by increasing their expression or activities, i.e. without heterologous genes having to be introduced into the yeast, (ii)a) the co-factor specificity of acetohydroxy acid reducto-isomerase is modified such that this enzyme preferably uses NADH instead of NADPH as a co-factor, or (ii)b) the co-factor specificity of the glyceraldehyde-3-phosphate dehydrogenase is modified such that this enzyme preferably uses $NADP^+$ instead of $NAD^+$ as co-factor or a heterologous NADP glyceraldehyde-3-phosphate dehydrogenase is expressed in the yeast cells, (iii) the formation of secondary products such as e.g. ethanol is minimized and (iv) in which as many of the enzymes involved as possible are located in the cytosol of the yeast cells.

The object is achieved according to the invention by the over-expression of the enzyme activities of Ilv2 with or without its activator Ilv6, Ilv5, Ilv3, at least one 2-keto acid decarboxylase such as e.g. Aro10 and at least one alcohol dehydrogenase which can also reduce isobutyraldehyde (preferably Adh1 or Adh6, but also Adh2-5, Sfa1, Ypr1 or others). This is carried out firstly through the exchange of the respective promoters of the corresponding genes for stronger promoters, preferably, but not exclusively, constitutive promoters. Preferably, but not exclusively, promoter sequences are selected from HXT7, shortened HXT7, PFK1, FBA1, TPI1, PGK1, PMA1, ADH1, TDH3. Furthermore, the corresponding nucleic acid sequences of the genes are converted into codon-optimized alleles. Every amino acid is encoded at gene level by a codon. However, for most amino acids there are several different codons which code for a single amino acid. The genetic code is consequently degenerated. The preferred codon choice for a corresponding amino acid differs from organism to organism. Thus in the case of heterologously expressed genes, problems can occur if the host organism or the host cell has a very different codon usage. The gene may not be expressed at all, or only slowly. But a different codon usage can also be detected in genes of different proteins and metabolic pathways within a cell. Glycolysis genes from *S. cerevisiae* are known to be strongly expressed. They have a strongly restrictive codon usage which corresponds approximately to the quantity ratios of the corresponding tRNAs. The adaptation of the codon usage of the genes ILV2, (ILV6) (SEQ. ID. no. 3), ILV5, ILV3, one of the above-named 2-keto acid decarboxylase genes and one of the above-named alcohol dehydrogenase genes to the preferred codon usage of *S. cerevisiae* results in an improvement of the isobutanol formation rate in yeast. The preferred codon usage can be defined as described in Wiedemann and Boles (2008) for the glycolytic genes, but need not necessarily be restricted to these examples. The over-expressed, possibly codon-optimized genes can either be inserted cloned on plasmids into the yeast cells, they can be integrated into the genome of the yeast cells or they can genomically replace the naturally occurring alleles.

SUMMARY

The present invention therefore relates in a first embodiment to a yeast cell producing isobutanol, characterized in that the cell has an increased metabolic flow of material from pyruvate via acetolactate, 2,3-dihydroxy isovalerate, 2-ketoisovalerate, isobutyraldehyde to isobutanol, in that at least one of the genes which code for the enzymes which are involved in this conversion is over-expressed and without any of these genes being heterologous to the said yeast cell, wherein Ilv2 (=YMR108W) catalyzes the acetolactate synthase reaction from pyruvate to acetolactate, Ilv5 (=YLR355C) catalyzes the acetohydroxy acid reducto-isomerase reaction from acetolactate to 2,3-dihydroxy isovalerate, Ilv3 (=YJR016C) catalyzes the dihydroxy acid dehydratase reaction from 2,3-dihydroxy isovalerate to 2-ketoisovalerate, a 2-keto acid decarboxylase catalyzes the reaction from 2-ketoisovalerate to isobutyraldehyde, and an alcohol dehydrogenase catalyzes the reaction from isobutyraldehyde to isobutanol, wherein either at least one of the promoters of these genes is exchanged for at least one stronger promoter or the nucleic acid sequences of these genes are converted into codon-optimized alleles.

In a preferred embodiment, the yeast cell according to the invention is characterized in that the at least one stronger promoter is a constitutive promoter.

In a further preferred embodiment, the yeast cell according to the invention is characterized in that the promoter sequence is selected from the group consisting of HXT7, shortened HXT7, PFK1, FBA1, TPI1, PGK1, PMA1, ADH1 and TDH3.

In a further preferred embodiment, the yeast cell according to the invention is characterized in that the 2-keto acid decarboxylase is selected from at least one of the enzymes Pdc1, Pdc5, Pdc6, Aro10 or Thi3.

In a further preferred embodiment, the yeast cell according to the invention is characterized in that the alcohol deyhdrogenase is selected from at least one of the enzymes Adh1 (SEQ. ID. no. 24), Adh2 (SEQ. ID. no. 26), Adh3 (SEQ. ID. no. 28), Adh4 (SEQ. ID. no. 30), Adh5 (SEQ. ID. no. 32), Adh6 (SEQ. ID. no. 34), Adh7 (SEQ. ID. no. 36), Sfa1 (SEQ. ID. no. 38) or Ypr1 (SEQ. ID. no. 40).

In a further preferred embodiment, the yeast cell according to the invention is characterized in that the over-expressed gene is over-expressed in a codon-optimized variant.

In a further preferred embodiment, the yeast cell according to the invention is characterized in that the over-expressed gene is over-expressed in a codon-optimized variant, wherein the codon optimization is aligned with the codon usage of the highly-expressed glycolysis genes of yeast.

In a further preferred embodiment, the yeast cell according to the invention is characterized in that the genes of all the enzymes which are involved in the conversion of pyruvate to isobutanol are over-expressed.

In a further preferred embodiment, the yeast cell according to the invention is characterized in that all these genes are over-expressed in codon-optimized variants.

In a further preferred embodiment, the yeast cell according to the invention is characterized in that all these genes are over-expressed in codon-optimized variants, wherein the codon optimization is aligned with the codon usage of the highly-expressed glycolysis genes of yeast.

In a further preferred embodiment, the yeast cell according to the invention is characterized in that the cell expresses an acetohydroxy acid reducto-isomerase which has an increased specificity for NADH compared with NADPH.

In a further preferred embodiment, the yeast cell according to the invention is characterized in that this NADH-preferring acetohydroxy acid reducto-isomerase is a mutated variant of the Ilv5 enzyme of the yeast.

In a further preferred embodiment, the yeast cell according to the invention is characterized in that an NADH-preferring alcohol dehydrogenase of yeast which converts isobutyraldehyde into isobutanol is simultaneously over-expressed.

In a further preferred embodiment, the yeast cell according to the invention is characterized in that the cell also expresses a phosphorylative glyceraldehyde-3-phosphate dehydrogenase which has an increased specificity for $NADP^+$ compared with $NAD^+$.

In a further preferred embodiment, the yeast cell according to the invention is characterized in that this NADP-preferring glyceraldehyde-3-phosphate dehydrogenase is heterologous to the yeast host cell.

In a further preferred embodiment, the yeast cell according to the invention is characterized in that this NADP-glyceraldehyde-3-phosphate dehydrogenase is encoded by mutated alleles of one, two or all three TDH1-3 (SEQ. ID. no. 41), (SEQ. ID. no. 43), (SEQ. ID. no. 45) genes of yeast.

In a further preferred embodiment, the yeast cell according to the invention is characterized in that this NADP-glyceraldehyde-3-phosphate dehydrogenase is expressed in a yeast cell which displays no or a reduced expression or activity of the NAD-glyceraldehyde-3-phosphate dehydrogenases.

In a further preferred embodiment, the yeast cell according to the invention is characterized in that an NADPH-preferring alcohol dehydrogenase which converts isobutyraldehyde into isobutanol is simultaneously over-expressed.

In a further preferred embodiment, the yeast cell according to the invention is characterized in that the enzymes acetolactate synthase, acetohydroxy acid reducto-isomerase and dihydroxy acid dehydratase are located in the cytosol of the cell.

In a further preferred embodiment, the yeast cell according to the invention is characterized in that in addition the Ilv6 protein (=YCL009C) is over-expressed in the same cell compartment as Ilv2.

In a further preferred embodiment, the yeast cell according to the invention is characterized in that in addition the expression of the genes PDC1 (SEQ. ID. no. 13), PDC5 (SEQ. ID. no. 15) and PDC6 (SEQ. ID. no. 17) or the activity of the encoded enzymes is reduced or switched off.

In a further preferred embodiment, the yeast cell according to the invention is characterized in that additional mutations increase the production of isobutanol.

In a further preferred embodiment, the yeast cell according to the invention is characterized in that additional mutations increase the resistance to toxic concentrations of isobutanol.

In a further preferred embodiment, the yeast cell according to the invention is characterized in that the cell is selected from the following group: *Pichia, Candida, Hansenula, Kluyveromyces, Yarrowia* and *Saccharomyces*.

In a further preferred embodiment, the yeast cell according to the invention is characterized in that the host cell is *Saccharomyces cerevisiae*.

DETAILED DESCRIPTION

Figure 1:
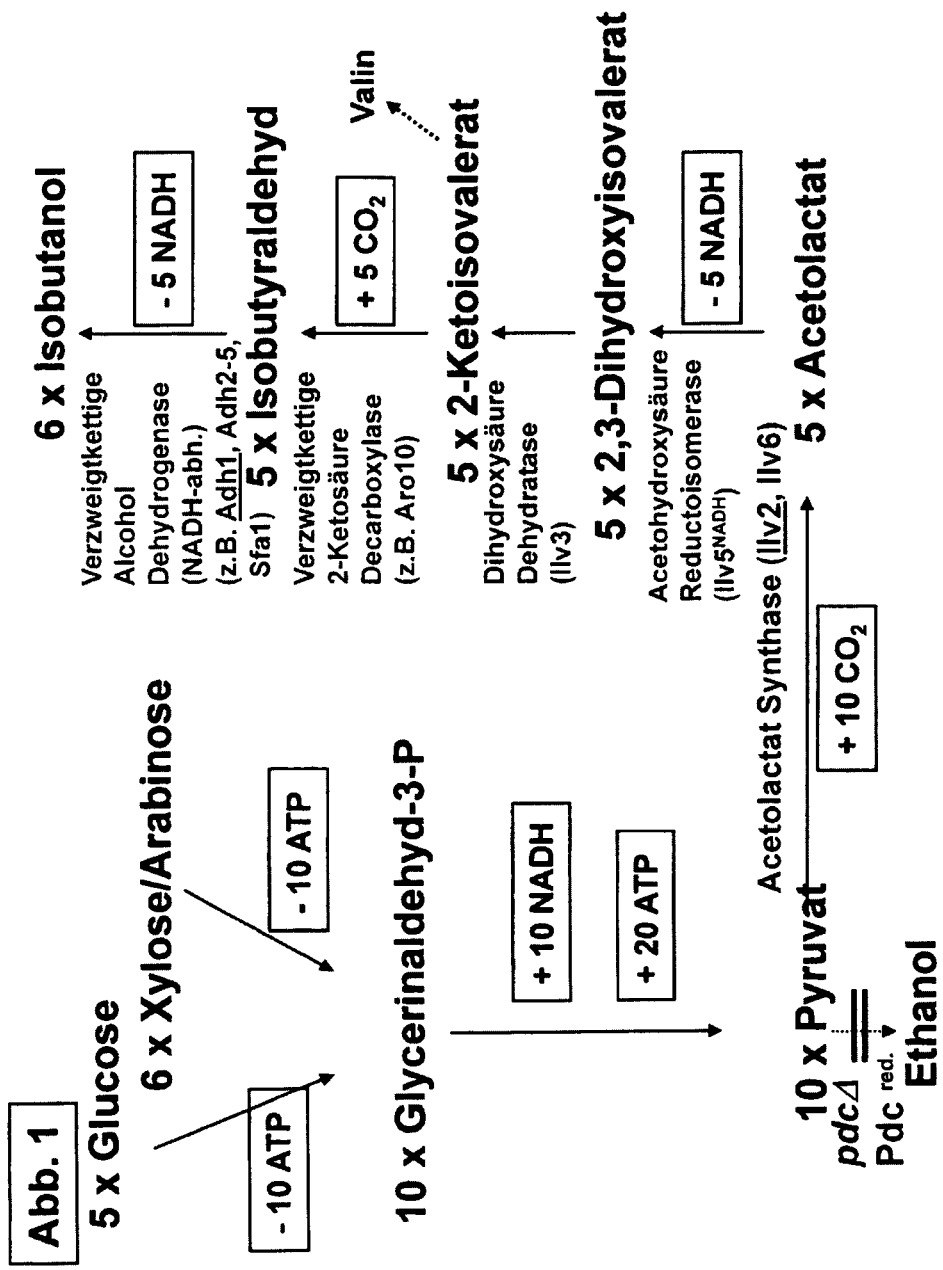
FIG. 1 illustrates one embodiment of the invention.

In a possible embodiment of the invention (see FIG. 1) the enzyme Ilv5 (acetohydroxy acid reducto-isomerase) is modified such that it preferably uses NADH instead of NADPH as co-factor. At the same time, an alcohol dehydrogenase which also uses NADH as co-factor (e.g. Adh1 or Adh2-5 or Sfa1) is preferably but not necessarily over-expressed. Ilv5 catalyzes the reduction of acetolactate to 2,3-dihydroxy isovalerate accompanied by the simultaneous oxidation of NADPH+H$^+$ to NADP$^+$. As a result of the glycolytic breakdown of sugars, however, no or only small quantities of NADPH form. However, NADH does form. But NADH is not easily convertible into NADPH (Boles et al., 1993). For this reason, it would be desirable to modify the co-factor specificity of acetohydroxy acid reducto-isomerase such that this enzyme prefers NADH instead of NADPH. This can be achieved by replacing specific amino acids of Ilv5, which are required for the exclusive use of NADPH, by others which also or preferably allow a use of NADH. Such amino acids are preferably but not exclusively the amino acids Arg108, Gly111, Ala112 and/or Ser113 of the non-processed precursor enzymes which can be derived by comparing the yeast-Ilv5 enzyme with the structure of the acetohydroxy acid reducto-isomerase of spinach (Biou et al., 1997). Arg108 can preferably but not exclusively be converted to Met, Trp, Phe, Glu or Asp, Gly111 preferably but not exclusively into Glu or Asp, Ala112 preferably but not exclusively into Ser or Gly and Ser113 preferably but not exclusively into Glu or Asp. However, it is not to be ruled out that the exchange of further or different amino acids also leads to a modification of the co-factor specificity of Ilv5 in favour of NADH.

Figure 2:
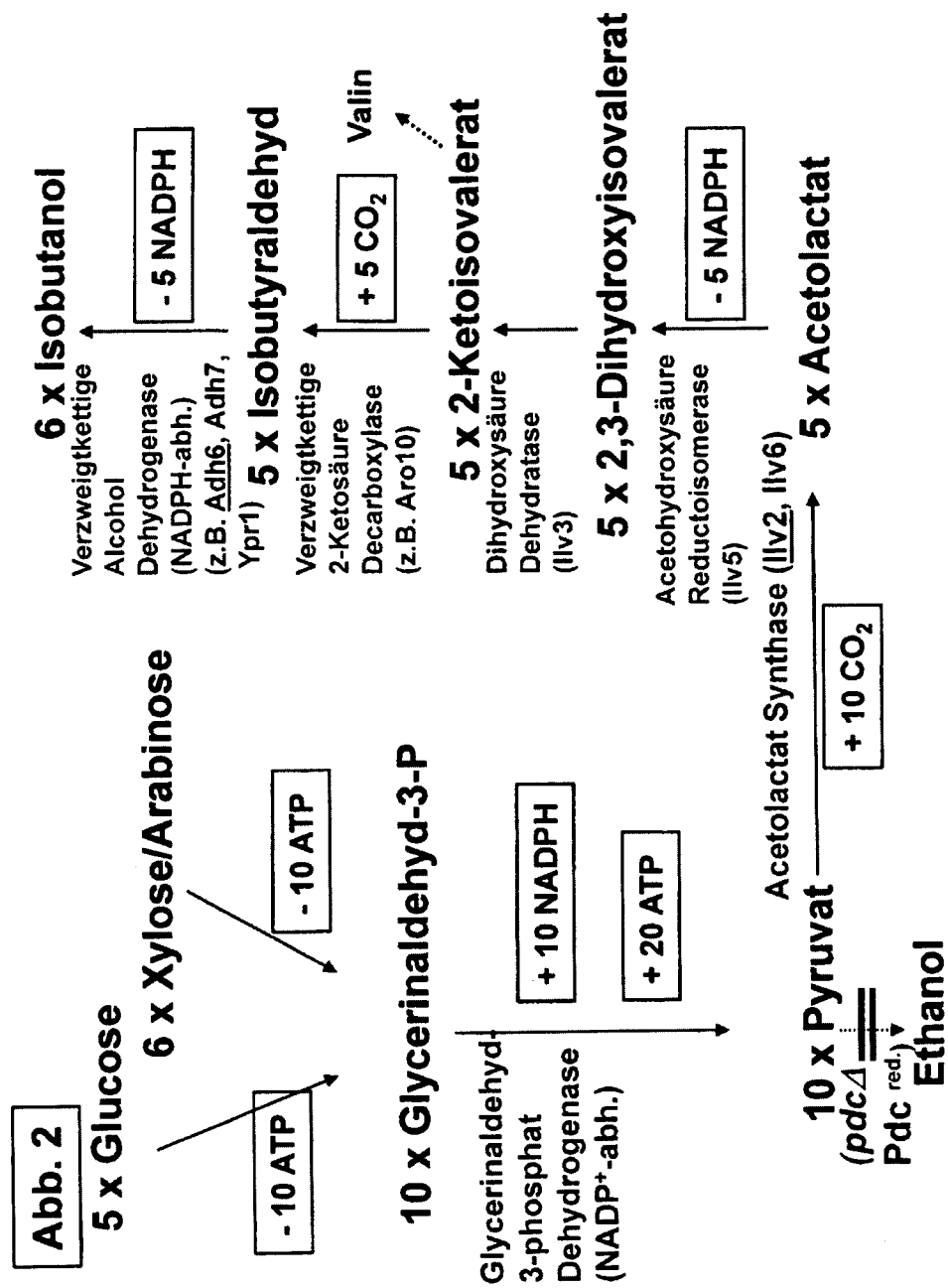
FIG. 2 illustrates another embodiment of the invention.

In another possible embodiment of the invention (see FIG. 2) the glyceraldehyde-3-phosphate dehydrogenase (GAPDH) of the yeast is modified such that it prefers NADP$^+$ instead of NAD$^+$, or is replaced or supplemented by a glyceraldehyde-3-phosphate dehydrogenase which prefers NADP$^+$ compared with NAD$^+$. At the same time, an alcohol dehydrogenase which prefers NADPH as co-factor (e.g. Adh6 or Ypr1) is preferably but not necessarily over-expressed. GAPDH is encoded e.g. in *S. cerevisiae* by the genes TDH1 (SEQ. ID. no. 41), TDH2 (SEQ. ID. no. 43) and TDH3 (SEQ. ID. no. 45) and catalyzes the oxidation of glyceraldehyde-3-phosphate accompanied by simultaneous phosphorylation to 1,3-diphosphoglycerate. During the glycolytic breakdown of sugars, NAD$^+$ is usually used as co-factor, and NADH+H$^+$ forms. NADH is not easily convertible into NADPH (Boles et al., 1993). However, as the acetohydroxy acid reducto-isomerase NADPH is used as co-factor, it would be desirable to modify the co-factor specificity of GAPDH such that this enzyme prefers NADP$^+$ instead of NAD$^+$. A modification of the co-factor specificity of the yeast-GAPDH can be achieved by replacing specific amino acids of Tdh1 (SEQ. ID. no. 42), Tdh2 (SEQ. ID. no. 44) and/or Tdh3 (SEQ. ID. no. 46), which are required for the exclusive use of NAD$^+$, by others which also or preferably allow a use of NADP$^+$. Such amino acids are preferably but not exclusively the amino acids Asp33 and/or Gly188-Pro189, which can be derived by comparing the yeast-GAPDH enzymes with the structure of NADP$^+$-preferred GAPDHs (Fillinger et al., 2000). Asp33 can preferably but not exclusively be converted to Asn, Gly, Ala or Ser, Gly188-Pro189 preferably but not exclusively into Ala-Ser, Val-Arg, Asn-Pro or Thr-Lys. However, it is not to be ruled out that the exchange of further or different amino acids also leads to a modification of the co-factor specificity of Tdh1-3 in favour of NADP$^+$. Alternatively, a heterologous GAPDH which preferably uses NADP$^+$, e.g. but not exclusively Gdp1 (SEQ. ID. no. 48) from *Kluyveromyces lactis* (Verho et al., 2002) or GapB (SEQ. ID. no. 50) from *Bacillus subtilis* (Fillinger et al., 2000) could be over-expressed in yeast. The NADP-GAPDH can be over-expressed codon-optimized in a preferred embodiment. The mutated or heterologous NADP-GAPDHs can be expressed in addition to the NAD-GAPDHs present or in a preferred version in yeast mutants with reduced or switched-off NAD-GAPDH expression or activity.

Proteins that are transported into the mitochondrial matrix are synthesized as precursor proteins in the cytosol and then transported via translocases into the mitochondrial matrix. The N-terminal presequences are split from a mitochondrial peptidase during translocation. In a preferred embodiment, but not necessarily, the genes ILV2, (ILV6), ILV5 or ILV5$^{(NADHmut.)}$ and ILV3 are over-expressed without the mitochondrial targeting sequence of the corresponding proteins or with a broken, inactivated mitochondrial targeting sequence, with the result that the produced proteins are preferably located in the cytosol of the yeast cells (Pang and Duggleby, 1999; Omura, 2008). This can be carried out with the natural or codon-optimized alleles.

Pyruvate can be further converted by various reaction paths. The quantitatively strongest of these reaction paths is its conversion into ethanol. Pyruvate is decarboxylated to acetaldehyde and further to ethanol by the pyruvate decarboxylases (Pdcs). Pyruvate is lost to the production of isobutanol. In a preferred embodiment of the invention, but not necessarily, the flow of the pyruvate to ethanol is therefore blocked or reduced by switching off or reducing the pyruvate decarboxylase expression or activities. This is carried out e.g. by deleting or reducing the expression of the genes PDC1, PDC5 and/or PDC6. However, as yeast requires the acetyl-CoA produced in the cytosol from acetaldehyde, this must also be made available when the pyruvate decarboxylases are completely switched off. This is carried out either (i) by an incomplete switching-off of the expression or activity of the pyruvate decarboxylases, (ii) by expression of a heterologous pyruvate-formiate lyase with its activating enzyme including the over-expression of a formiate dehydrogenase, (iii) by heterologous expression of a reversible mitochondrial carnitine carrier or (iv) by the introduction of spontaneous suppressor mutations. In addition, the possibility of reducing or switching off further metabolic reactions in order to intensify the flow of the intermediate metabolites to isobutanol still remains.

Furthermore, the production of isobutanol as well as the resistance to toxic concentrations of isobutanol in the recombinant yeast cells can be further increased by random mutagenesis or the "Evolutionary Engineering" or "Directed Evolution" methods (Sauer, 2001).

The present invention furthermore relates to a method for the production of isobutanol with yeast cells, comprising the provision of a yeast cell as defined above as well as bringing the yeast cell into contact with a fermentable carbon source.

In a preferred embodiment, the method according to the invention is characterized in that the fermentable carbon source is a C3-C6 carbon source.

In a further preferred embodiment, the method according to the invention is characterized in that the carbon source belongs to the group consisting of monosaccharides, oligosaccharides or polysaccharides.

In a further preferred embodiment, the method according to the invention is characterized in that the carbon source belongs to the group consisting of glucose, fructose, mannose, galactose, saccharose, maltose, xylose or arabinose.

In a further preferred embodiment, the method according to the invention is characterized in that the host cell is brought into contact with the carbon source in culture medium.

METHODS

1. Strains and Media 1.1 Bacteria
 E. coli SURE (Stratagene)
 E. coli DH5α (Stratagene)
 Full medium LB 1% Trypton, 0.5% yeast extract, 0.5% NaCl, pH 7.5 (see Maniatis, 1982).
 For the selection for a plasmid-encoded resistance to antibiotics 40 µg/ml ampicillin was added to the medium after autoclaving. Solid nutrient media also contained 2% agar. Culture took place at 37° C.

1.2 Yeast
 Strains from the CEN.PK series, industrial yeasts
 synthetic complete selective medium SC:
 0.67% yeast nitrogen base w/o amino acids, pH 6.3, amino acid/nucleobase solution, carbon source in the respective given concentration
 synthetic minimal selective medium SM:
 0.16% yeast nitrogen base w/o amino acid and ammonium sulphate, 0.5% ammonium sulphate, 20 mM potassium dihydrogen phosphate, pH6.3, carbon source in the respective given concentration
 synthetic fermentation medium (mineral medium) SFM:
 (Verduyn et al., 1992), pH 5.5
 Salts: $(NH_4)_2SO_4$, 5 g/l; $KH_2PO_4$, 3 g/l; $MgSO_4*7H_2O$, 0.5 g/l
 Trace elements: EDTA, 15 mg/l, $ZnSO_4*4.5$ mg/l; $MnCl_2*4H_2O$, 0.1 mg/l; $CoCl_2*6H_2O$, 0.3 mg/l; $CuSO_4$, 0.192 mg/l; $Na_2MoO_4*2H_2O$, 0.4 mg/l; $CaCl_2*2H_2O$, 4.5 mg/l; $FeSO_4*7H_2O$, 3 mg/l; $H_3BO_3$, 1 mg/l; KI, 0.1 mg/l
 Vitamins: biotin, 0.05 mg/l; p-aminobenzoic acid, 0.2 mg/l; nicotinic acid, 1 mg/l; calcium pantothenate, 1 mg/l; pyridoxine-HCL, 1 mg/l; thiamine-HCL, 1 mg/l; minositol, 25 mg/l
 Concentration of the amino acids and nucleobases in the synthetic complete medium (according to Zimmermann, 1975): adenine (0.08 mM), arginine (0.22 mM), histidine (0.25 mM), isoleucine (0.44 mM), leucine (0.44 mM), lysine (0.35 mM), methionine (0.26 mM), phenylalanine (0.29 mM), tryptophane (0.19 mM), threonine (0.48 mM), tyrosine (0.34 mM), uracil (0.44 mM), valine (0.49 mM). L-arabinose and D-glucose were used as carbon source.

Solid full and selective media also contained 1.8% agar. Cultivation of the yeast cells took place at 30° C. The synthetic mineral medium used for the fermentations contained salts, trace metals and vitamins in the concentrations listed above and L-arabinose as carbon source. A parent solution of the trace metals and vitamins was prepared. Both solutions were sterile-filtered. Both were stored at 4° C. The pH was a decisive factor for the production of the trace metal solution. The different trace elements had to be fully dissolved in water one after the other in the order given above. After every addition, the pH had to be adjusted to 6.0 with KOH before the next trace element could be added. At the end, the pH was adjusted to 4.0 with HCL. To avoid foaming, 200 µl antifoam (Antifoam2004, Sigma) was added to the medium. As the experiments were carried out under anaerobic conditions, 2.5 ml/l of a Tween80-Ergosterol solution also had to be added to the medium after autoclaving. This consists of 16.8 g Tween80 and 0.4 g Ergosterol, which were made up to 50 ml with ethanol and dissolved therein. The solution was sterile-filtered. The salts and the antifoam were autoclaved jointly with the complete fermenter. The arabinose was autoclaved separately from the rest of the medium. After cooling of the medium, the trace elements as well as the vitamins were added.

2. Transformation 2.1 Transformation of E. coli
 The transformation of the E. coli cells took place using the electroporation method according to Dower et al. (1988) and Wirth (1993) by means of an Easyject prima device (EQUIBO).

2.2 Transformation of S. cerevisiae

The transformation of S. cerevisiae strains with plasmid DNA or DNA fragments took place according to the lithium acetate method of Gietz and Woods (1994).

3. Preparation of DNA

3.1 Isolation of Plasmid DNA from E. coli

The isolation of plasmid DNA from E. coli took place according to the alkaline lysis method of Birnboim and Doly (1979), modified according to Maniatis et al. (1982) or alternatively with the Qiagen "QIAprep Spin Miniprep Kit".

High-purity plasmid DNA for sequencing was prepared with the Qiagen "Plasmid Mini Kit" according to the manufacturer's instructions.

3.2 Isolation of Plasmid DNA from S. cerevisiae

The cells of a stationary yeast culture (5 ml) were harvested by centrifugation, washed and resuspended in 400 µl buffer P1 (Plasmid Mini Kit, Qiagen). Following the addition of 400 µl buffer P2 and ⅔ volume glass beads (Ø 0.45 mm), cells were broken by 5 minutes' shaking on a Vibrax (Vibrax-VXR from Janke & Kunkel or IKA). ½ volume buffer P3 was added to the supernatant, and the whole mixed and incubated on ice for 10 min. After 10 minutes' centrifugation at 13000 rpm, the plasmid DNA was precipitated at room temperature by adding 0.75 ml isopropanol to the supernatant. The DNA pelleted by centrifugation for 30 min at 13000 rpm was washed with 70% ethanol, dried and resuspended in 20 µl water. 1 µl of DNA was used for the transformation into E. coli.

3.3 Determination of the DNA Concentration

The DNA concentration was spectrophotometrically measured in a wavelength range of from 240-300 nm. If the purity of the DNA, determined by the quotient $E_{260nm}/E_{280nm}$, is 1.8, the absorbance $E_{260nm}=1.0$ corresponds to a DNA concentration of 50 µg dsDNA/ml (Maniatis et al., 1982).

3.4 DNA Amplification by Means of PCR

Use of the Phusion™ High Fidelity System

The polymerase chain reaction was carried out in a total volume of 50 µl with the Finnzymes "Phusion™ High Fidelity PCR System" in accordance with the manufacturer's instructions. Each batch consisted of 1-10 ng DNA or 1-2 yeast colonies as synthesis template, 0.2 mM dNTP-Mix, 1× buffer 2 (contains 1.5 mM $MgCl_2$), 1 U polymerase and 100 pmol of each of the corresponding oligonucleotide primer. The PCR reaction was carried out in a Techne thermocycler and the PCR conditions selected as follows according to the requirements:

| 1 | 1x | 30 sec, 98° C. | denaturation of DNA |
|---|-----|----------------|---------------------|
| 2 | 30x | 10 sec, 98° C. | denaturation of DNA |
|   |     | 30 sec, 56-62° C. | annealing/binding of the oligonucleotides to the DNA |
|   |     | 0.5-1 min, 72° C. | DNA synthesis/elongation |
| 3 | 1x | 7 min, 72° C. | DNA synthesis/elongation |

After the first denaturation step, the polymerase was added ("hot start PCR"). The number of synthesis steps, the annealing temperature and the elongation time were adapted to the specific melting temperatures of the oligonucleotides used or to the size of the expected product. The PCR products were examined by an agarose gel electrophoresis and then purified.

3.5 DNA Purification of PCR Products

The purification of the PCR products was carried out with the "QIAquick PCR Purification Kit" from Qiagen in accordance with the manufacturer's instructions.

3.6 Gel Electrophoretic Separation of DNA Fragments

The separation of DNA fragments measuring 0.15-20 kb was carried out in 0.5-1% agarose gels with 0.5 µg/ml ethidium bromide. 1×TAE buffer (40 mM TRIS, 40 mM ethyl acetate, 2 mM EDTA) was used as gel and running buffers (Maniatis et al., 1982). A lambda phage DNA cut with the restriction endonucleases EcoRI and HindIII served as marker. ⅒ volume blue marker (1×TAE buffer, 10% glycerol, 0.004% bromphenol blue) was added to the DNA samples before application and made visible after separation by irradiation with UV light (254 nm).

3.7 Isolation of DNA Fragments from Agarose Gels

The desired DNA fragment was cut out from the TAE agarose gel under long-wave UV light (366 nm) and isolated with the Qiagen "QIAquick Gel Extraction Kit" in accordance with the manufacturer's instructions.

4. Enzymatic Modification of DNA

4.1 DNA Restriction

Sequence-specific splitting of the DNA with restriction endonucleases was carried out under the manufacturer's recommended incubation conditions for 1 hour with 2-5 U enzyme per µg DNA.

Further possible expression vectors are from the pRS303X, p3RS305X and p3RS306X series. These are integrative vectors which have a dominant antibiotic marker. Further details about these vectors are to be found in Taxis and Knop (2006).

5. Cloning of DNA Fragments by In Vivo Recombination

For an in-vivo cloning of DNA fragments in S. cerevisiae, first the corresponding gene or DNA sequence is synthesized by a PCR reaction. The therein used oligonucleotides each contain in the 5' region 36-39 nucleotides comprising specific appendages which are homologous to the 5'- or 3'-flanking sequences of the integration region in the target vector. In the 3' region, the oligonucleotides contain 20-22 bases homologous to the 3' or 5' ends of the gene to be amplified. The PCR product produced was transformed into yeast together with the vector linearized and purified by restriction in the integration region. The cells were plated out onto synthetic selective medium which lacked the corresponding amino acid or nucleotide base for the selection on the auxotrophic marker of the vector. In this way, only transformants which had again formed a stable, circular plasmid due to homologous recombination of the DNA fragment in the linearized vector were obtained. The plasmids were isolated, amplified in E. coli and examined by subsequent restriction analysis, or by sequencing.

6. Exchange of and Integration into Genomic DNA

This was carried out as described in Becker and Boles (2003) and Wieczorke et al. (1999).

REFERENCES

Atsumi S, Hanai T and Liao J C (2008) Non-fermentative pathway for synthesis of branched-chain higher alcohols as biofuels. Nature 451, 86-90.

Bailey J E (1993) Host-vector interactions in Escherichia coli. Adv Biochem Eng. 48, 29-52

Becker J, Boles E (2003) A modified Saccharomyces cerevisiae strain that consumes L-Arabinose and produces ethanol. Appl Environ Microbiol. 69, 4144-4150.

Biou V, Dumas R, Cohen-Addad C, Douce R, Job D and Pebay-Peyroula E (1997) The crystal structure of plant acetohydroxy acid isomeroreductase complexed with NADPH, two magnesium ions and a herbicidal transition state analog determined at 1.65 A resolution. EMBO J. 16, 3405-3415.

Birnboim H C, Doly J (1979) A rapid alkaline extraction procedure for screening recombinant plasmid DNA. Nucl. Acids Res. 7, 1513-1523

Boles E, Lehnert W and Zimmermann F K (1993) The role of the NAD-dependent glutamate dehydrogenase in restoring growth on glucose of a *Saccharomyces cerevisiae* phosphoglucose isomerase mutant. Eur. J. Biochem. 217, 469-477.

Dickinson J R, Harrison S J and Hewlins M J E (1998) An investigation of the metabolism of valine to isobutyl alcohol in *Saccharomyces cerevisiae*. J. Biol. Chem. 273, 25751-25756.

Dickinson J R, Salgado L E J and Hewlins M J E (2003) The catabolism of amino acids to long chain and complex alcohols in *Saccharomyces cerevisiae*. J. Biol. Chem. 278, 8028-8034.

Dower W J, Miller J F, Ragsdale C W (1988) High efficiency transformation of *E. coli* by high voltage electroporation. Nucl. Acids Res. 16, 6127-6145

Fillinger S, Boschi-Muller S, Azza S, Dervyn E, Branlant G and Aymerich S (2000) Two glyceraldehyde-3-phosphate dehydrogenases with opposite physiological roles in a non-photosynthetic bacterium. J. Biol. Chem. 275, 14031-14037.

Gietz R D, Woods R A (1994) High efficiency transformation in yeast. In: Molecular Genetics of Yeast: Practical Approaches, J. A. Johnston (Ed.). Oxford University Press pp. 121-134

Maniatis T, Fritsch E F, Sambrook J (1982) Molecular cloning. A laboratory manual. Cold Spring Harbor Laboratory, New York.

Omura F (2008) Targeting of mitochondrial *Saccharomyces cerevisiae* Ilv5p to the cytosol and its effect on vicinal diketone formation in brewing. Appl. Microbiol. Biotechnol. (DOI 10.1007/s00253-007-1333-x)

Pang S S and Duggleby R G (1999) Expression, purification, characterization, and reconstitution of the large and small subunits of yeast acetohydroxyacid synthase. Biochemistry 38, 5222-5231

US patent application 2007/0092957 A1 (Fermentive production of four carbon alcohols)

Sauer U (2001) Evolutionary engineering of industrially important microbial phenotypes. Adv Biochem. Eng. Biotechnol. 73, 129-169.

Taxis C, Knop M (2006) System of centromeric, episomal, and integrative vectors based on drug resistance markers for *Saccharomyces cerevisiae*. BioTechniques 40, No. 1

Verduyn C, Postma E, Scheffers W A, Van Dijken J P (1992) Effect of benzoic acid on metabolic fluxes in yeasts: a continuous culture study on the regulation of respiration and alcoholic fermentation. Yeast 8, 501-17

Verho R, Richard P, Jonson P H, Sundqvist L, Londesbrorough J and Penttilä M (2002) Identification of the first fungal NADP-GAPDH from *Kluyveromyces lactis*. Biochemistry 41, 13833-13838.

Wieczorke R, Krampe S, Weierstall T, Freidel K, Hollenberg C P, Boles E (1999) Concurrent knock-out of at least 20 transporter genes is required to block uptake of hexoses in *Saccharomyces cerevisiae*. FEBS Lett 464, 123-128.

Wiedemann B and Boles E (2008), Codon-optimized bacterial genes improve L-arabinose fermentation in recombinant *Saccharomyces cerevisiae*. Appl. Environ. Microbiol. 74, 2043-2050.

Wirth R (1989) Elektroporation: Eine alternative Methode zur Transformation von Bakterien mit Plasmid-DNA. Forum Mikrobiologie 11, 507-515.

Zimmermann F K (1975) Procedures used in the induction of mitotic recombination and mutation in the yeast *Saccharomyces cerevisiae*. Mutation Res. 31, 71-81.

The invention claimed is:

1. A yeast cell producing isobutanol, characterized in that the cell has an increased metabolic flow of material from pyruvate via acetolactate, 2,3-dihydroxy isovalerate, 2-ketoisovalerate, isobutyraldehyde to isobutanol, in that at least one of the genes which code for the enzymes which are involved in this conversion is over-expressed and without any of these genes being heterologous to the said yeast cell, wherein Ilv2 (=YMR108W) (SEQ. ID. no. 2) catalyzes the acetolactate synthase reaction from pyruvate to acetolactate, Ilv5 (=YLR355C) (SEQ. ID. no. 6) catalyzes the acetohydroxy acid reducto-isomerase reaction from acetolactate to 2,3-dihydroxy isovalerate, Ilv3 (=YJR016C) (SEQ. ID. no. 8) catalyzes the dihydroxy acid dehydratase reaction from 2,3-dihydroxy isovalerate to 2-ketoisovalerate, a 2-keto acid decarboxylase catalyzes the reaction from 2-ketoisovalerate to isobutyraldehyde, characterized in that the 2-keto acid decarboxylase is selected from at least one of the enzymes Aro10 (SEQ. ID no. 20) or Thi3 (SEQ. ID. no. 22), and an alcohol dehydrogenase catalyzes the reaction from isobutyraldehyde to isobutanol, characterized in that the alcohol dehydrogenase is selected from at least one of the enzymes Adh1 (SEQ. ID no. 24), and Adh2 (SEQ. ID. no. 26). Adh3 (SEQ. ID. no. 28), Adh4 (SEQ. ID. no. 30), Adh5 (SEQ. ID. no. 32), Adh6 (SEQ. ID. no. 34), Adh7 (SEQ. ID. no. 36), Sfa1 (SEQ. ID. no. 38) or Ypr1 (SEQ. ID. no. 40), wherein either at least one of the promoters of these genes is exchanged for at least one stronger promoter or the nucleic acid sequences of these genes are converted into codon-optimized alleles; characterized in that the enzymes acetolactate synthase, acetohydroxy acid reducto-isomerase and dihydroxy acid dehydratase are located in the cytosol of the cell.

2. The yeast cell according to claim 1, characterized in that the at least one stronger promoter is a constitutive promoter.

3. The yeast cell according to claim 1, characterized in that the promoter sequence is selected from the group consisting of HXT7, shortened HXT7, PFK1, FBA1, TPI1, PGK1, PMA1, ADH1 and TDH3.

4. The yeast cell according to claim 1, characterized in that the over-expressed gene is over-expressed in a codon-optimized variant.

5. The yeast cell according to claim 4, characterized in that the over-expressed gene is over-expressed in a codon-optimized variant, wherein the codon optimization is aligned with the codon usage of the highly-expressed glycolysis gene of yeast.

6. The yeast cell according to claim 1, characterized in that the genes of all enzymes which are involved in the conversion of pyruvate to isobutanol are over-expressed.

7. The yeast cell according to claim 6, characterized in that all of these genes are over-expressed in codon-optimized variants.

8. The yeast cell according to claim 7, characterized in that all of these genes are over-expressed in codon-optimized variants, wherein the codon optimization is aligned with the codon usage of the highly-expressed glycolysis gene of yeast.

9. The yeast cell according to claim 1, characterized in that the cell expresses an acetohydroxy acid reducto-isomerase which has an increased specificity for NADH compared with NADPH.

10. The yeast according to claim 9, characterized in that this NADH-preferring acetohydroxy acid reducto-isomerase is a mutated variant of the Ilv5-enzyme of yeast.

11. The yeast cell according to claim 9, characterized in that an NADH-preferring alcohol dehydrogenase of yeast which converts isobutyraldehyde into isobutanol is simultaneously over-expressed.

12. The yeast cell according to claim 1, characterized in that the cell also expresses a phosphorylative glyceraldehyde-3-phosphate dehydrogenase which has an increased specificity for $NADP^+$ compared with $NAD^+$.

13. The yeast cell according to claim 12, characterized in that this NADP-preferring glyceraldehyde-3-phosphate dehydrogenase is heterologous to the yeast host cell.

14. The yeast cell according to claim 12, characterized in that this NADP-glyceraldehyde-3-phosphate dehydrogenase is encoded by mutated alleles of one, two or all three TDH1-3 (SEQ. ID. no. 41), (SEQ. ID. no. 43), (SEQ. ID. no. 45) genes of yeast.

15. The yeast cell according to claim 12, characterized in that this NADP-glyceraldehyde-3-phosphate dehydrogenase is expressed in a yeast cell which displays no or a reduced expression or activity of the NAD-glyceraldehyde-3-phosphate dehydrogenases.

16. The yeast cell according to claim 12, characterized in that an NADPH-preferring alcohol dehydrogenase which converts isobutyraldehyde into isobutanol is simultaneously over-expressed.

17. The yeast cell according to claim 1, characterized in that in addition the Ilv6 protein (=YCL009C) (SEQ. ID. no. 4) is over-expressed in the same cell compartment as Ilv2.

18. The yeast cell according to claim 1, characterized in that in addition the expression of the genes PDC1 (SEQ. ID. no. 13), PDC5 (SEQ. ID. no. 15) and PDC6 (SEQ. ID. no. 17) or the activity of the encoded enzymes is reduced or switched off.

19. The yeast cell according to claim 1, characterized in that additional mutations increase the production of isobutanol.

20. The yeast cell according to claim 1, characterized in that additional mutations increase the resistance to toxic concentrations of isobutanol.

21. The yeast cell according to claim 1, characterized in that the cell is selected from the group consisting of *Pichia, Candida, Hansenula, Kluyveromyces, Yarrowia* and *Saccharomyces*.

22. The yeast cell according to claim 21, characterized in that the host cell is *Saccharomyces cerevisiae*.

23. A method for the production of isobutanol with yeast cells, comprising the provision of a yeast cell according to claim 1 as well as bringing the yeast cell into contact with a fermentable carbon source.

24. The method according to claim 23, characterized in that the fermentable carbon source is a C3-C6 carbon source.

25. The method according to claim 23, characterized in that the carbon source belongs to the group consisting of monosaccharides, oligosaccharides and polysaccharides.

26. The method according to claim 25, characterized in that the carbon source belongs to the group consisting of glucose, fructose, mannose, galactose, saccharose, maltose, xylose and arabinose.

27. The method according to claim 23, characterized in that the host cell is brought into contact with the carbon source in culture medium.

* * * * *

UNITED STATES PATENT AND TRADEMARK OFFICE
CERTIFICATE OF CORRECTION

PATENT NO. : 8,530,226 B2  
APPLICATION NO. : 12/918722  
DATED : September 10, 2013  
INVENTOR(S) : Festel et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 134 days.

Signed and Sealed this
Fifteenth Day of September, 2015

Michelle K. Lee
*Director of the United States Patent and Trademark Office*

SEQUENCE LISTING

```
<160> NUMBER OF SEQ ID NOS: 50

<210> SEQ ID NO 1
<211> LENGTH: 2064
<212> TYPE: DNA
<213> ORGANISM: Saccharomyces cerevisiae

<400> SEQUENCE: 1
atgatcagac aatctacgct aaaaaacttc gctattaagc gttgctttca acatatagca      60
taccgcaaca cacctgccat gagatcagta gctctcgcgc agcgcttta tagttcgtct     120 tcccgttatt acagtgcgtc tccattacca gcctctaaaa ggccagagcc tgctccaagt     180
ttcaatgttg atccattaga acagcccgct gaaccttcaa aattggctaa gaaactacgc     240
gctgagcctg acatggatac ctctttcgtc ggtttaactg gtggtcaaat atttaacgaa     300
atgatgtcca gacaaaacgt tgatactgta tttggttatc caggtggtgc tatcctacct     360
gtttacgatg ccattcataa cagtgataaa ttcaacttcg ttcttccaaa acacgaacaa     420
ggtgccggtc acatggcaga aggctacgcc agagcttctg gtaaaccagg tgttgtcttg     480
gttacttctg ggccaggtgc caccaatgtc gttactccaa tggcagatgc ctttgcagac     540
gggattccaa tggttgtctt tacagggcaa gtcccaacta gtgctatcgg tactgatgct     600
```

```
ttccaagagg ctgacgtcgt tggtatttct agatcttgta cgaaatggaa tgtcatggtc    660
aagtccgtgg aagaattgcc attgcgtatt aacgaggctt ttgaaattgc acgagcggt     720 agaccgggac cagtcttggt cgatttacca aaggatgtta cagcagctat cttaagaaat    780
ccaattccaa caaaaacaac tcttccatca acgcactaa accaattaac cagtcgcgca     840
caagatgaat tgtcatgca aagtatcaat aaagcagcag atttgatcaa cttggcaaag     900
aaacctgtct tatacgtcgg tgctggtatt ttaaaccatg cagatggtcc aagattacta    960
aaagaattaa gtgaccgtgc tcaaatacct gtcaccacta ctttacaagg tttaggttca   1020
ttcgaccaag aagatccaaa atcattggat atgcttggta tgcacggttg tgctactgcc   1080
aacctggcag tgcaaaatgc cgacttgata attgcagttg gtgctagatt cgacgaccgt   1140
gtcactggta atatttctaa attcgctcca gaagctcgtc gtgcagctgc cgagggtaga   1200
ggtggtatta ttcatttcga ggttagtcca aaaaacataa acaaggttgt tcaaactcaa   1260
atagcagtgg aaggtgatgc tacgaccaat ctgggcaaaa tgatgtcaaa gattttccca   1320
gttaaggaga ggtctgaatg gtttgctcaa ataaataaat ggaagaagga atacccatac   1380
gcttatatgg aggagactcc aggatctaaa attaaaccac agacggttat aaagaaacta   1440
tccaaggttg ccaacgacac aggaagacat gtcattgtta caacgggtgt ggggcaacat   1500
caaatgtggg ctgctcaaca ctggacatgg agaaatccac atactttcat cacatcaggt   1560
ggtttaggta cgatgggtta cggtctccct gccgccatcg gtgctcaagt tgcaaagcca   1620
gaatctttgg ttattgacat tgatggtgac gcatccttta acatgactct aacggaattg   1680
agttctgccg ttcaagctgg tactccagtg aagattttga ttttgaacaa tgaagagcaa   1740
ggtatggtta ctcaatggca atccctgttc tacgaacatc gttattccca cacacatcaa   1800
ttgaaccctg atttcataaa actagcggag gctatgggtt taaaaggttt aagagtcaag   1860
aagcaagagg aattggacgc taagttgaaa gaattcgttt ctaccaaggg cccagttttg   1920
cttgaagtgg aagttgataa aaaagttcct gttttgccaa tggtggcagg tggtagcggt   1980
ctagacgagt tcataaattt tgacccagaa gttgaaagac aacagactga attacgtcat   2040
aagcgtacag gcggtaagca ctga                                          2064
```

<210> SEQ ID NO 2
<211> LENGTH: 687
<212> TYPE: PRT
<213> ORGANISM: Saccharomyces cerevisiae

<400> SEQUENCE: 2

```
Met Ile Arg Gln Ser Thr Leu Lys Asn Phe Ala Ile Lys Arg Cys Phe
1               5                   10                  15

Gln His Ile Ala Tyr Arg Asn Thr Pro Ala Met Arg Ser Val Ala Leu
            20                  25                  30

Ala Gln Arg Phe Tyr Ser Ser Ser Arg Tyr Tyr Ser Ala Ser Pro
        35                  40                  45

Leu Pro Ala Ser Lys Arg Pro Glu Pro Ala Pro Ser Phe Asn Val Asp
    50                  55                  60

Pro Leu Glu Gln Pro Ala Glu Pro Ser Lys Leu Ala Lys Lys Leu Arg
65                  70                  75                  80

Ala Glu Pro Asp Met Asp Thr Ser Phe Val Gly Leu Thr Gly Gly Gln
                85                  90                  95

Ile Phe Asn Glu Met Met Ser Arg Gln Asn Val Asp Thr Val Phe Gly
            100                 105                 110

Tyr Pro Gly Gly Ala Ile Leu Pro Val Tyr Asp Ala Ile His Asn Ser
```

```
            115                 120                 125
Asp Lys Phe Asn Phe Val Leu Pro Lys His Glu Gln Gly Ala Gly His
130                 135                 140
Met Ala Glu Gly Tyr Ala Arg Ala Ser Gly Lys Pro Gly Val Val Leu
145                 150                 155                 160
Val Thr Ser Gly Pro Gly Ala Thr Asn Val Val Thr Pro Met Ala Asp
                165                 170                 175
Ala Phe Ala Asp Gly Ile Pro Met Val Val Phe Thr Gly Gln Val Pro
                180                 185                 190
Thr Ser Ala Ile Gly Thr Asp Ala Phe Gln Glu Ala Asp Val Val Gly
                195                 200                 205
Ile Ser Arg Ser Cys Thr Lys Trp Asn Val Met Val Lys Ser Val Glu
                210                 215                 220
Glu Leu Pro Leu Arg Ile Asn Glu Ala Phe Glu Ile Ala Thr Ser Gly
225                 230                 235                 240
Arg Pro Gly Pro Val Leu Val Asp Leu Pro Lys Asp Val Thr Ala Ala
                245                 250                 255
Ile Leu Arg Asn Pro Ile Pro Thr Lys Thr Thr Leu Pro Ser Asn Ala
                260                 265                 270
Leu Asn Gln Leu Thr Ser Arg Ala Gln Asp Glu Phe Val Met Gln Ser
                275                 280                 285
Ile Asn Lys Ala Ala Asp Leu Ile Asn Leu Ala Lys Lys Pro Val Leu
                290                 295                 300
Tyr Val Gly Ala Gly Ile Leu Asn His Ala Asp Gly Pro Arg Leu Leu
305                 310                 315                 320
Lys Glu Leu Ser Asp Arg Ala Gln Ile Pro Val Thr Thr Thr Leu Gln
                325                 330                 335
Gly Leu Gly Ser Phe Asp Gln Glu Asp Pro Lys Ser Leu Asp Met Leu
                340                 345                 350
Gly Met His Gly Cys Ala Thr Ala Asn Leu Ala Val Gln Asn Ala Asp
                355                 360                 365
Leu Ile Ile Ala Val Gly Ala Arg Phe Asp Asp Arg Val Thr Gly Asn
370                 375                 380
Ile Ser Lys Phe Ala Pro Glu Ala Arg Arg Ala Ala Ala Glu Gly Arg
385                 390                 395                 400
Gly Gly Ile Ile His Phe Glu Val Ser Pro Lys Asn Ile Asn Lys Val
                405                 410                 415
Val Gln Thr Gln Ile Ala Val Glu Gly Asp Ala Thr Thr Asn Leu Gly
                420                 425                 430
Lys Met Met Ser Lys Ile Phe Pro Val Lys Glu Arg Ser Glu Trp Phe
                435                 440                 445
Ala Gln Ile Asn Lys Trp Lys Lys Glu Tyr Pro Tyr Ala Tyr Met Glu
                450                 455                 460
Glu Thr Pro Gly Ser Lys Ile Lys Pro Gln Thr Val Ile Lys Lys Leu
465                 470                 475                 480
Ser Lys Val Ala Asn Asp Thr Gly Arg His Val Ile Val Thr Thr Gly
                485                 490                 495
Val Gly Gln His Gln Met Trp Ala Ala Gln His Trp Thr Trp Arg Asn
                500                 505                 510
Pro His Thr Phe Ile Thr Ser Gly Gly Leu Gly Thr Met Gly Tyr Gly
                515                 520                 525
Leu Pro Ala Ala Ile Gly Ala Gln Val Ala Lys Pro Glu Ser Leu Val
530                 535                 540
```

```
Ile Asp Ile Asp Gly Asp Ala Ser Phe Asn Met Thr Leu Thr Glu Leu
545                 550                 555                 560
Ser Ser Ala Val Gln Ala Gly Thr Pro Val Lys Ile Leu Ile Leu Asn
                565                 570                 575
Asn Glu Glu Gln Gly Met Val Thr Gln Trp Gln Ser Leu Phe Tyr Glu
            580                 585                 590
His Arg Tyr Ser His Thr His Gln Leu Asn Pro Asp Phe Ile Lys Leu
        595                 600                 605
Ala Glu Ala Met Gly Leu Lys Gly Leu Arg Val Lys Lys Gln Glu Glu
    610                 615                 620
Leu Asp Ala Lys Leu Lys Glu Phe Val Ser Thr Lys Gly Pro Val Leu
625                 630                 635                 640
Leu Glu Val Glu Val Asp Lys Lys Val Pro Val Leu Pro Met Val Ala
                645                 650                 655
Gly Gly Ser Gly Leu Asp Glu Phe Ile Asn Phe Asp Pro Glu Val Glu
            660                 665                 670
Arg Gln Gln Thr Glu Leu Arg His Lys Arg Thr Gly Gly Lys His
        675                 680                 685

<210> SEQ ID NO 3
<211> LENGTH: 930
<212> TYPE: DNA
<213> ORGANISM: Saccharomyces cerevisiae

<400> SEQUENCE: 3
atgctgagat cgttattgca aagcggccac cgcagggtgg ttgcttcttc atgtgctacc     60
atggtgcgtt gcagttcctc gtcgacctcc gcgttggcgt acaagcagat gcacagacac    120
gcaacaagac ctcccttgcc cacactagac actccttcct ggaatgccaa cagtgccgtt    180
tcatccatca tttacgaaac accagcgcct tctcgtcaac caagaaaaca gcatgtcttg    240
aactgtttgg tgcaaaacga acccggtgtc ttgtccagag tctcgggtac gttagctgcc    300
agaggcttta acatcgattc gttggtcgtg tgcaacaccg aggtcaaaga cctaagtaga    360
atgaccattg ttttgcaagg gcaagatggc gtagtcgaac aagcacgcag acaaatcgaa    420
gacttggtcc ccgtctacgc cgtcctagac tataccaatt ctgagatcat caaaagagag    480
ctagtgatgg ccagaatctc tctattgggt actgaatact tcgaagacct actattgcac    540
caccacactt ccaccaatgc tggcgccgct gactcccaag aattggtcgc cgaaatcaga    600
gaaaagcaat ccaccctgc caacttgccc gccagtgagg tattaaggtt gaagcacgag    660
catttgaacg atatcaccaa cttgaccaac aactttggag gtcgtgtcgt cgacatcagc    720
gaaacaagct gtattgtgga gttgtctgca aaacccacac gtatctctgc cttcttgaag    780
ttggtcgagc cattcggtgt cctagagtgt gcaagaagcg gtatgatggc attgccaaga    840
actcctttga agacaagcac cgaggaagct gccgacgaag acgaaaagat cagcgaaatc    900
gtcgacattt cccaactacc acctggttag                                     930

<210> SEQ ID NO 4
<211> LENGTH: 309
<212> TYPE: PRT
<213> ORGANISM: Saccharomyces cerevisiae

<400> SEQUENCE: 4

Met Leu Arg Ser Leu Leu Gln Ser Gly His Arg Arg Val Val Ala Ser
1               5                   10                  15
Ser Cys Ala Thr Met Val Arg Cys Ser Ser Ser Thr Ser Ala Leu
            20                  25                  30
```

```
Ala Tyr Lys Gln Met His Arg His Ala Thr Arg Pro Pro Leu Pro Thr
         35                  40                  45

Leu Asp Thr Pro Ser Trp Asn Ala Asn Ser Ala Val Ser Ser Ile Ile
 50                  55                  60

Tyr Glu Thr Pro Ala Pro Ser Arg Gln Pro Arg Lys Gln His Val Leu
 65                  70                  75                  80

Asn Cys Leu Val Gln Asn Glu Pro Gly Val Leu Ser Arg Val Ser Gly
                 85                  90                  95

Thr Leu Ala Ala Arg Gly Phe Asn Ile Asp Ser Leu Val Val Cys Asn
            100                 105                 110

Thr Glu Val Lys Asp Leu Ser Arg Met Thr Ile Val Leu Gln Gly Gln
        115                 120                 125

Asp Gly Val Val Glu Gln Ala Arg Arg Gln Ile Glu Asp Leu Val Pro
    130                 135                 140

Val Tyr Ala Val Leu Asp Tyr Thr Asn Ser Glu Ile Ile Lys Arg Glu
145                 150                 155                 160

Leu Val Met Ala Arg Ile Ser Leu Leu Gly Thr Glu Tyr Phe Glu Asp
                165                 170                 175

Leu Leu His His His Thr Ser Thr Asn Ala Gly Ala Ala Asp Ser
            180                 185                 190

Gln Glu Leu Val Ala Glu Ile Arg Glu Lys Gln Phe His Pro Ala Asn
        195                 200                 205

Leu Pro Ala Ser Glu Val Leu Arg Leu Lys His Glu His Leu Asn Asp
    210                 215                 220

Ile Thr Asn Leu Thr Asn Asn Phe Gly Gly Arg Val Val Asp Ile Ser
225                 230                 235                 240

Glu Thr Ser Cys Ile Val Glu Leu Ser Ala Lys Pro Thr Arg Ile Ser
                245                 250                 255

Ala Phe Leu Lys Leu Val Glu Pro Phe Gly Val Leu Glu Cys Ala Arg
            260                 265                 270

Ser Gly Met Met Ala Leu Pro Arg Thr Pro Leu Lys Thr Ser Thr Glu
        275                 280                 285

Glu Ala Ala Asp Glu Asp Glu Lys Ile Ser Glu Ile Val Asp Ile Ser
    290                 295                 300

Gln Leu Pro Pro Gly
305

<210> SEQ ID NO 5
<211> LENGTH: 1188
<212> TYPE: DNA
<213> ORGANISM: Saccharomyces cerevisiae

<400> SEQUENCE: 5
atgttgagaa ctcaagccgc cagattgatc tgcaactccc gtgtcatcac tgctaagaga      60
acctttgctt tggccacccg tgctgctgct tacagcagac cagctgcccg tttcgttaag     120
ccaatgatca ctacccgtgg tttgaagcaa atcaacttcg gtggtactgt tgaaaccgtc     180
tacgaaagag ctgactggcc aagagaaaag ttgttggact acttcaagaa cgacactttt     240
gctttgatcg gttacggttc ccaaggttac ggtcaaggtt tgaacttgag agacaacggt     300
ttgaacgtta tcattggtgt ccgtaaagat ggtgcttctt ggaaggctgc atcgaagac      360 ggttgggttc aggcaagaa cttgttcact gttgaagatg ctatcaagag aggtagttac     420
gttatgaact tgttgtccga tgccgctcaa tcagaaacct ggcctgctat caagccattg     480
ttgaccaagg gtaagacttt gtacttctcc cacggtttct ccccagtctt caaggacttg     540
```

-continued

```
actcacgttg aaccaccaaa ggacttagat gttatcttgg ttgctccaaa gggttccggt    600
agaactgtca gatctttgtt caaggaaggt cgtggtatta actcttctta cgccgtctgg    660
aacgatgtca ccggtaaggc tcacgaaaag gcccaagctt tggccgttgc cattggttcc    720
ggttacgttt accaaaccac tttcgaaaga gaagtcaact ctgacttgta cggtgaaaga    780
ggttgtttaa tgggtggtat ccacggtatg ttcttggctc aatacgacgt cttgagagaa    840
aacggtcact ccccatctga agctttcaac gaaaccgtcg aagaagctac ccaatctcta    900
tacccattga tcggtaagta cggtatggat tacatgtacg atgcttgttc caccaccgcc    960
agaagaggtg ctttggactg gtacccaatc ttcaagaatg ctttgaagcc tgttttccaa   1020
gacttgtacg aatctaccaa gaacggtacc gaaaccaaga gatctttgga attcaactct   1080
caacctgact acagagaaaa gctagaaaag gaattagaca ccatcagaaa catggaaatc   1140
tggaaggttg gtaaggaagt cagaaagttg agaccagaaa accaataa              1188
```

<210> SEQ ID NO 6
<211> LENGTH: 395
<212> TYPE: PRT
<213> ORGANISM: Saccharomyces cerevisiae

<400> SEQUENCE: 6

```
Met Leu Arg Thr Gln Ala Ala Arg Leu Ile Cys Asn Ser Arg Val Ile
  1               5                  10                  15

Thr Ala Lys Arg Thr Phe Ala Leu Ala Thr Arg Ala Ala Ala Tyr Ser
                 20                  25                  30

Arg Pro Ala Ala Arg Phe Val Lys Pro Met Ile Thr Thr Arg Gly Leu
             35                  40                  45

Lys Gln Ile Asn Phe Gly Gly Thr Val Glu Thr Val Tyr Glu Arg Ala
         50                  55                  60

Asp Trp Pro Arg Glu Lys Leu Leu Asp Tyr Phe Lys Asn Asp Thr Phe
 65                  70                  75                  80

Ala Leu Ile Gly Tyr Gly Ser Gln Tyr Gly Gln Gly Leu Asn Leu
                 85                  90                  95

Arg Asp Asn Gly Leu Asn Val Ile Ile Gly Val Arg Lys Asp Gly Ala
                100                 105                 110

Ser Trp Lys Ala Ala Ile Glu Asp Gly Trp Val Pro Gly Lys Asn Leu
            115                 120                 125

Phe Thr Val Glu Asp Ala Ile Lys Arg Gly Ser Tyr Val Met Asn Leu
        130                 135                 140

Leu Ser Asp Ala Ala Gln Ser Glu Thr Trp Pro Ala Ile Lys Pro Leu
145                 150                 155                 160

Leu Thr Lys Gly Lys Thr Leu Tyr Phe Ser His Gly Phe Ser Pro Val
                165                 170                 175

Phe Lys Asp Leu Thr His Val Glu Pro Pro Lys Asp Leu Asp Val Ile
            180                 185                 190

Leu Val Ala Pro Lys Gly Ser Gly Arg Thr Val Arg Ser Leu Phe Lys
        195                 200                 205

Glu Gly Arg Gly Ile Asn Ser Ser Tyr Ala Val Trp Asn Asp Val Thr
    210                 215                 220

Gly Lys Ala His Glu Lys Ala Gln Ala Leu Ala Val Ala Ile Gly Ser
225                 230                 235                 240

Gly Tyr Val Tyr Gln Thr Thr Phe Glu Arg Glu Val Asn Ser Asp Leu
                245                 250                 255

Tyr Gly Glu Arg Gly Cys Leu Met Gly Gly Ile His Gly Met Phe Leu
```

```
              260                 265                 270
Ala Gln Tyr Asp Val Leu Arg Glu Asn Gly His Ser Pro Ser Glu Ala
            275                 280                 285

Phe Asn Glu Thr Val Glu Ala Thr Gln Ser Leu Tyr Pro Leu Ile
        290                 295                 300

Gly Lys Tyr Gly Met Asp Tyr Met Tyr Asp Ala Cys Ser Thr Thr Ala
305                 310                 315                 320

Arg Arg Gly Ala Leu Asp Trp Tyr Pro Ile Phe Lys Asn Ala Leu Lys
                325                 330                 335

Pro Val Phe Gln Asp Leu Tyr Glu Ser Thr Lys Asn Gly Thr Glu Thr
            340                 345                 350

Lys Arg Ser Leu Glu Phe Asn Ser Gln Pro Asp Tyr Arg Glu Lys Leu
        355                 360                 365

Glu Lys Glu Leu Asp Thr Ile Arg Asn Met Glu Ile Trp Lys Val Gly
    370                 375                 380

Lys Glu Val Arg Lys Leu Arg Pro Glu Asn Gln
385                 390                 395

<210> SEQ ID NO 7
<211> LENGTH: 1758
<212> TYPE: DNA
<213> ORGANISM: Saccharomyces cerevisiae

<400> SEQUENCE: 7
```

| | | | | | |
|---|---|---|---|---|---|
| atgggcttgt | aacgaaagt | tgctacatct | agacaattct | ctacaacgag | atgcgttgca | 60 |
| aagaagctca | acaagtactc | gtatatcatc | actgaaccta | agggccaagg | tgcgtcccag | 120 |
| gccatgcttt | atgccaccgg | tttcaagaag | gaagatttca | agaagcctca | agtcggggtt | 180 |
| ggttcctgtt | ggtggtccgg | taacccatgt | aacatgcatc | tattggactt | gaataacaga | 240 |
| tgttctcaat | ccattgaaaa | agcgggtttg | aaagctatgc | agttcaacac | catcggtgtt | 300 |
| tcagacggta | tctctatggg | tactaaaggt | atgagatact | cgttacaaag | tagagaaatc | 360 |
| attgcagact | cctttgaaac | catcatgatg | gcacaacact | acgatgctaa | catcgccatc | 420 |
| ccatcatgtg | acaaaaacat | gcccggtgtc | atgatggcca | tgggtagaca | taacagacct | 480 |
| tccatcatgg | tatatggtgg | tactatcttg | cccggtcatc | caacatgtgg | ttcttcgaag | 540 |
| atctctaaaa | acatcgatat | cgtctctgcg | ttccaatcct | acggtgaata | tatttccaag | 600 |
| caattcactg | aagaagaaag | agaagatgtt | gtggaacatg | catgcccagg | tcctggttct | 660 |
| tgtggtggta | tgtatactgc | caacacaatg | gcttctgccg | ctgaagtgct | aggttttgacc | 720 |
| attccaaact | cctcttcctt | cccagccgtt | tccaaggaga | agttagctga | gtgtgacaac | 780 |
| attggtgaat | acatcaagaa | gacaatggaa | ttgggtattt | tacctcgtga | tatcctcaca | 840 |
| aaagaggctt | ttgaaaacgc | cattacttat | gtcgttgcaa | ccggtgggtc | cactaatgct | 900 |
| gttttgcatt | tggtggctgt | tgctcactct | gcgggtgtca | agttgtcacc | agatgatttc | 960 |
| caaagaatca | gtgatactac | accattgatc | ggtgacttca | aaccttctgg | taaatacgtc | 1020 |
| atggccgatt | tgattaacgt | tggtggtacc | caatctgtga | ttaagtatct | atatgaaaac | 1080 |
| aacatgttgc | acggtaacac | aatgactgtt | accggtgaca | ctttggcaga | acgtgcaaag | 1140 |
| aaagcaccaa | gcctacctga | aggacaagag | attattaagc | cactctccca | cccaatcaag | 1200 |
| gccaacggtc | acttgcaaat | tctgtacggt | tcattggcac | aggtggagc | tgtgggtaaa | 1260 |
| attaccggta | aggaaggtac | ttacttcaag | ggtagagcac | gtgtgttcga | agaggaaggt | 1320 |
| gcctttattg | aagccttgga | aagaggtgaa | atcaagaagg | gtgaaaaaac | cgttgttgtt | 1380 |

-continued

```
atcagatatg aaggtccaag aggtgcacca ggtatgcctg aaatgctaaa gccttcctct    1440
gctctgatgg gttacggttt gggtaaagat gttgcattgt tgactgatgg tagattctct    1500
ggtggttctc acgggttctt aatcggccac attgttcccg aagccgctga aggtggtcct    1560
atcgggttgg tcagagacgg cgatgagatt atcattgatg ctgataataa caagattgac    1620
ctattagtct ctgataagga aatggctcaa cgtaaacaaa gttgggttgc acctccacct    1680
cgttacacaa gaggtactct atccaagtat gctaagttgg tttccaacgc ttccaacggt    1740
tgtgttttag atgcttga                                                  1758
```

<210> SEQ ID NO 8
<211> LENGTH: 585
<212> TYPE: PRT
<213> ORGANISM: Saccharomyces cerevisiae

<400> SEQUENCE: 8

```
Met Gly Leu Leu Thr Lys Val Ala Thr Ser Arg Gln Phe Ser Thr Thr
1               5                   10                  15

Arg Cys Val Ala Lys Lys Leu Asn Lys Tyr Ser Tyr Ile Ile Thr Glu
            20                  25                  30

Pro Lys Gly Gln Gly Ala Ser Gln Ala Met Leu Tyr Ala Thr Gly Phe
        35                  40                  45

Lys Lys Glu Asp Phe Lys Lys Pro Gln Val Gly Val Gly Ser Cys Trp
    50                  55                  60

Trp Ser Gly Asn Pro Cys Asn Met His Leu Leu Asp Leu Asn Asn Arg
65                  70                  75                  80

Cys Ser Gln Ser Ile Glu Lys Ala Gly Leu Lys Ala Met Gln Phe Asn
                85                  90                  95

Thr Ile Gly Val Ser Asp Gly Ile Ser Met Gly Thr Lys Gly Met Arg
            100                 105                 110

Tyr Ser Leu Gln Ser Arg Glu Ile Ile Ala Asp Ser Phe Glu Thr Ile
        115                 120                 125

Met Met Ala Gln His Tyr Asp Ala Asn Ile Ala Ile Pro Ser Cys Asp
    130                 135                 140

Lys Asn Met Pro Gly Val Met Met Ala Met Gly Arg His Asn Arg Pro
145                 150                 155                 160

Ser Ile Met Val Tyr Gly Gly Thr Ile Leu Pro Gly His Pro Thr Cys
                165                 170                 175

Gly Ser Ser Lys Ile Ser Lys Asn Ile Asp Ile Val Ser Ala Phe Gln
            180                 185                 190

Ser Tyr Gly Glu Tyr Ile Ser Lys Gln Phe Thr Glu Glu Arg Glu
        195                 200                 205

Asp Val Val Glu His Ala Cys Pro Gly Pro Gly Ser Cys Gly Gly Met
    210                 215                 220

Tyr Thr Ala Asn Thr Met Ala Ser Ala Ala Glu Val Leu Gly Leu Thr
225                 230                 235                 240

Ile Pro Asn Ser Ser Ser Phe Pro Ala Val Ser Lys Glu Lys Leu Ala
                245                 250                 255

Glu Cys Asp Asn Ile Gly Glu Tyr Ile Lys Lys Thr Met Glu Leu Gly
            260                 265                 270

Ile Leu Pro Arg Asp Ile Leu Thr Lys Glu Ala Phe Glu Asn Ala Ile
        275                 280                 285

Thr Tyr Val Val Ala Thr Gly Gly Ser Thr Asn Ala Val Leu His Leu
    290                 295                 300

Val Ala Val Ala His Ser Ala Gly Val Lys Leu Ser Pro Asp Asp Phe
```

```
                305                 310                 315                 320
Gln Arg Ile Ser Asp Thr Thr Pro Leu Ile Gly Asp Phe Lys Pro Ser
                325                 330                 335
Gly Lys Tyr Val Met Ala Asp Leu Ile Asn Val Gly Gly Thr Gln Ser
                340                 345                 350
Val Ile Lys Tyr Leu Tyr Glu Asn Asn Met Leu His Gly Asn Thr Met
                355                 360                 365
Thr Val Thr Gly Asp Thr Leu Ala Glu Arg Ala Lys Lys Ala Pro Ser
                370                 375                 380
Leu Pro Glu Gly Gln Glu Ile Ile Lys Pro Leu Ser His Pro Ile Lys
385                 390                 395                 400
Ala Asn Gly His Leu Gln Ile Leu Tyr Gly Ser Leu Ala Pro Gly Gly
                405                 410                 415
Ala Val Gly Lys Ile Thr Gly Lys Glu Gly Thr Tyr Phe Lys Gly Arg
                420                 425                 430
Ala Arg Val Phe Glu Glu Glu Gly Ala Phe Ile Glu Ala Leu Glu Arg
                435                 440                 445
Gly Glu Ile Lys Lys Gly Glu Lys Thr Val Val Ile Arg Tyr Glu
                450                 455                 460
Gly Pro Arg Gly Ala Pro Gly Met Pro Glu Met Leu Lys Pro Ser Ser
465                 470                 475                 480
Ala Leu Met Gly Tyr Gly Leu Gly Lys Asp Val Ala Leu Leu Thr Asp
                485                 490                 495
Gly Arg Phe Ser Gly Gly Ser His Gly Phe Leu Ile Gly His Ile Val
                500                 505                 510
Pro Glu Ala Ala Glu Gly Gly Pro Ile Gly Leu Val Arg Asp Gly Asp
                515                 520                 525
Glu Ile Ile Ile Asp Ala Asp Asn Asn Lys Ile Asp Leu Leu Val Ser
                530                 535                 540
Asp Lys Glu Met Ala Gln Arg Lys Gln Ser Trp Val Ala Pro Pro Pro
545                 550                 555                 560
Arg Tyr Thr Arg Gly Thr Leu Ser Lys Tyr Ala Lys Leu Val Ser Asn
                565                 570                 575
Ala Ser Asn Gly Cys Val Leu Asp Ala
                580                 585

<210> SEQ ID NO 9
<211> LENGTH: 1182
<212> TYPE: DNA
<213> ORGANISM: Saccharomyces cerevisiae

<400> SEQUENCE: 9
atgttgcaga gacattcctt gaagttgggg aaattctcca tcagaacact cgctactggt        60
gccccattag atgcatccaa actaaaaatt actagaaacc caaatccatc caagccaaga       120
ccaaatgaag aattagtgtt cggccagaca ttcaccgatc atatgttgac cattccttgg       180
tcagccaaag aagggtgggg cactccacac atcaagcctt acggtaatct ttctcttgac       240
ccatctgctt gtgtattcca ttatgcattt gaattatttg aaggtttgaa agcctacaga       300
actcctcaaa atactatcac catgttccgt ccggataaga acatggcccg tatgaacaag       360
tctgccgcta gaatttgttt gccaactttc gaatctgaag aattgatcaa acttaccggg       420
aaattgatcg aacaagataa acacttggtt cctcaaggta atggttactc attatacatc       480
agaccaacaa tgattggtac atccaagggt ttaggtgttg cactccctc cgaggctctt       540 ctttatgtta ttacttctcc agtcggtcct tattataaga ctggtttcaa agccgtacgt       600
```

```
cttgaagcaa cagactatgc tacaagagct tggccaggtg gtgttggcga caaaaaattg      660
ggtgctaact atgccccatg catcttacct caactacaag ctgccaaaag agggtaccaa      720
caaaatctat ggttgttcgg cccagaaaag aacatcactg aggttggtac tatgaacgtg      780
ttcttcgttt tcctcaacaa agtcactggc aagaaggaat tggttaccgc tccattagat      840
ggtaccattt tagaaggtgt taccagagac tctgttttaa cattggctcg tgacaaacta      900
gatcctcaag aatgggacat caacgagcgt tattacacta ttactgaagt cgccactaga      960
gcaaaacaag gtgaactatt agaagccttc ggttctggta ctgctgctgt cgtttcacct     1020
atcaaggaaa ttggctggaa caacgaagat attcatgttc cactattgcc tggtgaacaa     1080
tgtggtgcat tgaccaagca agttgctcaa tggattgctg atatccaata cggtagagtc     1140
aattatggta actggtcaaa aactgttgcc gacttgaact aa                        1182

<210> SEQ ID NO 10
<211> LENGTH: 393
<212> TYPE: PRT
<213> ORGANISM: Saccharomyces cerevisiae

<400> SEQUENCE: 10

Met Leu Gln Arg His Ser Leu Lys Leu Gly Lys Phe Ser Ile Arg Thr
1               5                   10                  15

Leu Ala Thr Gly Ala Pro Leu Asp Ala Ser Lys Leu Lys Ile Thr Arg
            20                  25                  30

Asn Pro Asn Pro Ser Lys Pro Arg Pro Asn Glu Glu Leu Val Phe Gly
        35                  40                  45

Gln Thr Phe Thr Asp His Met Leu Thr Ile Pro Trp Ser Ala Lys Glu
    50                  55                  60

Gly Trp Gly Thr Pro His Ile Lys Pro Tyr Gly Asn Leu Ser Leu Asp
65                  70                  75                  80

Pro Ser Ala Cys Val Phe His Tyr Ala Phe Glu Leu Phe Glu Gly Leu
                85                  90                  95

Lys Ala Tyr Arg Thr Pro Gln Asn Thr Ile Thr Met Phe Arg Pro Asp
            100                 105                 110

Lys Asn Met Ala Arg Met Asn Lys Ser Ala Ala Arg Ile Cys Leu Pro
        115                 120                 125

Thr Phe Glu Ser Glu Glu Leu Ile Lys Leu Thr Gly Lys Leu Ile Glu
    130                 135                 140

Gln Asp Lys His Leu Val Pro Gln Gly Asn Gly Tyr Ser Leu Tyr Ile
145                 150                 155                 160

Arg Pro Thr Met Ile Gly Thr Ser Lys Gly Leu Gly Val Gly Thr Pro
                165                 170                 175

Ser Glu Ala Leu Leu Tyr Val Ile Thr Ser Pro Val Gly Pro Tyr Tyr
            180                 185                 190

Lys Thr Gly Phe Lys Ala Val Arg Leu Glu Ala Thr Asp Tyr Ala Thr
        195                 200                 205

Arg Ala Trp Pro Gly Gly Val Gly Asp Lys Lys Leu Gly Ala Asn Tyr
    210                 215                 220

Ala Pro Cys Ile Leu Pro Gln Leu Gln Ala Ala Lys Arg Gly Tyr Gln
225                 230                 235                 240

Gln Asn Leu Trp Leu Phe Gly Pro Glu Lys Asn Ile Thr Glu Val Gly
                245                 250                 255

Thr Met Asn Val Phe Phe Val Phe Leu Asn Lys Val Thr Gly Lys Lys
            260                 265                 270
```

Glu Leu Val Thr Ala Pro Leu Asp Gly Thr Ile Leu Glu Gly Val Thr
        275                 280                 285

Arg Asp Ser Val Leu Thr Leu Ala Arg Asp Lys Leu Asp Pro Gln Glu
        290                 295                 300

Trp Asp Ile Asn Glu Arg Tyr Tyr Thr Ile Thr Glu Val Ala Thr Arg
305                 310                 315                 320

Ala Lys Gln Gly Glu Leu Leu Glu Ala Phe Gly Ser Gly Thr Ala Ala
                325                 330                 335

Val Val Ser Pro Ile Lys Glu Ile Gly Trp Asn Asn Glu Asp Ile His
                340                 345                 350

Val Pro Leu Leu Pro Gly Glu Gln Cys Gly Ala Leu Thr Lys Gln Val
                355                 360                 365

Ala Gln Trp Ile Ala Asp Ile Gln Tyr Gly Arg Val Asn Tyr Gly Asn
        370                 375                 380

Trp Ser Lys Thr Val Ala Asp Leu Asn
385                 390

<210> SEQ ID NO 11
<211> LENGTH: 1131
<212> TYPE: DNA
<213> ORGANISM: Saccharomyces cerevisiae

<400> SEQUENCE: 11
atgaccttgg caccccctaga cgcctccaaa gttaagataa ctaccacaca acatgcatct        60
aagccaaaac cgaacagtga gttagtgttt ggcaagagct tcacggacca catgttaact       120
gcggaatgga cagctgaaaa agggtggggt accccagaga ttaaacctta tcaaaatctg       180
tctttagacc cttccgcggt ggttttccat tatgcttttg agctattcga agggatgaag       240
gcttacagaa cggtggacaa caaaattaca atgtttcgtc agatatgaa tatgaagcgc        300 atgaataagt ctgctcagag aatctgtttg ccaacgttcg acccagaaga gttgattacc       360
ctaattggga aactgatcca gcaagataag tgcttagttc ctgaaggaaa aggttactct       420
ttatatatca ggcctacatt aatcggcact acggccggtt tagggggtttc cacgcctgat       480 agagccttgc tatatgtcat ttgctgccct gtgggtcctt attacaaaac tggatttaag       540
gcggtcagac tggaagccac tgattatgcc acaagagctt ggccaggagg ctgtggtgac       600
aagaaactag gtgcaaacta cgcccccctgc gtcctgccac aattgcaagc tgcttcaagg       660
ggttaccaac aaaatttatg gctatttggt ccaaataaca acattactga agtcggcacc       720
atgaatgctt ttttcgtgtt taaagatagt aaaacgggca agaaggaact agttactgct       780
ccactagacg gtaccatttt ggaaggtgtt actagggatt ccattttaaa tcttgctaaa       840
gaaagactcg aaccaagtga atggaccatt agtgaacgct acttcactat aggcgaagtt       900
actgagagat ccaagaacgg tgaactactt gaagcctttg gttctggtac tgctgcgatt       960
gtttctccca ttaaggaaat cggctggaaa ggcgaacaaa ttaatattcc gttgttgccc      1020
ggcgaacaaa ccggtccatt ggccaaagaa gttgcacaat ggattaatgg aatccaatat      1080
ggcgagactg agcatggcaa ttggtcaagg gttgttactg atttgaactg a            1131

<210> SEQ ID NO 12
<211> LENGTH: 376
<212> TYPE: PRT
<213> ORGANISM: Saccharomyces cerevisiae

<400> SEQUENCE: 12

Met Thr Leu Ala Pro Leu Asp Ala Ser Lys Val Lys Ile Thr Thr Thr
1               5                   10                  15

```
Gln His Ala Ser Lys Pro Lys Pro Asn Ser Glu Leu Val Phe Gly Lys
            20                  25                  30

Ser Phe Thr Asp His Met Leu Thr Ala Glu Trp Thr Ala Glu Lys Gly
        35                  40                  45

Trp Gly Thr Pro Glu Ile Lys Pro Tyr Gln Asn Leu Ser Leu Asp Pro
50                  55                  60

Ser Ala Val Val Phe His Tyr Ala Phe Glu Leu Phe Glu Gly Met Lys
65                  70                  75                  80

Ala Tyr Arg Thr Val Asp Asn Lys Ile Thr Met Phe Arg Pro Asp Met
                85                  90                  95

Asn Met Lys Arg Met Asn Lys Ser Ala Gln Arg Ile Cys Leu Pro Thr
            100                 105                 110

Phe Asp Pro Glu Glu Leu Ile Thr Leu Ile Gly Lys Leu Ile Gln Gln
        115                 120                 125

Asp Lys Cys Leu Val Pro Glu Gly Lys Gly Tyr Ser Leu Tyr Ile Arg
    130                 135                 140

Pro Thr Leu Ile Gly Thr Thr Ala Gly Leu Gly Val Ser Thr Pro Asp
145                 150                 155                 160

Arg Ala Leu Leu Tyr Val Ile Cys Cys Pro Val Gly Pro Tyr Tyr Lys
                165                 170                 175

Thr Gly Phe Lys Ala Val Arg Leu Glu Ala Thr Asp Tyr Ala Thr Arg
            180                 185                 190

Ala Trp Pro Gly Gly Cys Gly Asp Lys Lys Leu Gly Ala Asn Tyr Ala
        195                 200                 205

Pro Cys Val Leu Pro Gln Leu Gln Ala Ala Ser Arg Gly Tyr Gln Gln
    210                 215                 220

Asn Leu Trp Leu Phe Gly Pro Asn Asn Ile Thr Glu Val Gly Thr
225                 230                 235                 240

Met Asn Ala Phe Phe Val Phe Lys Asp Ser Lys Thr Gly Lys Lys Glu
                245                 250                 255

Leu Val Thr Ala Pro Leu Asp Gly Thr Ile Leu Glu Gly Val Thr Arg
            260                 265                 270

Asp Ser Ile Leu Asn Leu Ala Lys Glu Arg Leu Glu Pro Ser Glu Trp
        275                 280                 285

Thr Ile Ser Glu Arg Tyr Phe Thr Ile Gly Glu Val Thr Glu Arg Ser
    290                 295                 300

Lys Asn Gly Glu Leu Leu Glu Ala Phe Gly Ser Gly Thr Ala Ala Ile
305                 310                 315                 320

Val Ser Pro Ile Lys Glu Ile Gly Trp Lys Gly Glu Gln Ile Asn Ile
                325                 330                 335

Pro Leu Leu Pro Gly Glu Gln Thr Gly Pro Leu Ala Lys Glu Val Ala
            340                 345                 350

Gln Trp Ile Asn Gly Ile Gln Tyr Gly Glu Thr Glu His Gly Asn Trp
        355                 360                 365

Ser Arg Val Val Thr Asp Leu Asn
    370                 375

<210> SEQ ID NO 13
<211> LENGTH: 1692
<212> TYPE: DNA
<213> ORGANISM: Saccharomyces cerevisiae

<400> SEQUENCE: 13
atgtctgaaa ttactttggg taaatatttg ttcgaaagat taaagcaagt caacgttaac      60
```

```
accgttttcg gtttgccagg tgacttcaac ttgtccttgt tggacaagat ctacgaagtt      120
gaaggtatga gatgggctgg taacgccaac gaattgaacg ctgcttacgc cgctgatggt      180
tacgctcgta tcaagggtat gtcttgtatc atcaccacct tcggtgtcgg tgaattgtct      240
gctttgaacg gtattgccgg ttcttacgct gaacacgtcg gtgttttgca cgttgttggt      300
gtcccatcca tctctgctca agctaagcaa ttgttgttgc accacacctt gggtaacggt      360
gacttcactg ttttccacag aatgtctgcc aacatttctg aaaccactgc tatgatcact      420
gacattgcta ccgccccagc tgaaattgac agatgtatca aaccacttac gtcacccaa       480
agaccagtct acttaggttt gccagctaac ttggtcgact gaacgtccc agctaagttg        540
ttgcaaactc caattgacat gtctttgaag ccaaacgatg ctgaatccga aaggaagtc        600
attgacacca tcttggcttt ggtcaaggat gctaagaacc cagttatctt ggctgatgct      660
tgttgttcca gacacgacgt caaggctgaa actaagaagt tgattgactt gactcaattc      720
ccagctttcg tcaccccaat gggtaagggt tccattgacg aacaacaccc aagatacggt      780
ggtgtttacg tcggtaccct tgtccaagcc aagttaagg aagccgttga atctgctgac       840
ttgatttttgt ctgtcggtgc tttgttgtct gatttcaaca ccggttcttt ctcttactct    900
tacaagacca agaacattgt cgaattccac tccgaccaca tgaagatcag aaacgccact      960
ttcccaggtg tccaaatgaa attcgttttg caaaagttgt tgaccactat tgctgacgcc    1020
gctaagggtt acaagccagt tgctgtccca gctagaactc cagctaacgc tgctgtccca    1080
gcttctaccc cattgaagca agaatggatg tggaaccaat tgggtaactt cttgcaagaa    1140
ggtgatgttg tcattgctga aaccggtacc tccgctttcg gtatcaacca aaccactttc    1200
ccaaacaaca cctacggtat ctctcaagtc ttatggggtt ccattggttt caccactggt    1260
gctaccttgg gtgctgcttt cgctgctgaa gaaattgatc aaagaagag agttatctta     1320
ttcattggtg acggttcttt gcaattgact gttcaagaaa tctccaccat gatcagatgg    1380
ggcttgaagc catacttgtt cgtcttgaac aacgatggtc acaccattga aaagttgatt    1440
cacggtccaa aggctcaata caacgaaatt caaggttggg accacctatc cttgttgcca    1500
actttcggtg ctaaggacta tgaaacccac agagtcgcta ccaccggtga atgggacaag    1560
ttgacccaag acaagtcttt caacgacaac tctaagatca gaatgattga atcatgttg     1620
ccagtcttcg atgctccaca aaacttggtt gaacaagcta gttgactgc tgctaccaac     1680
gctaagcaat aa                                                         1692
```

<210> SEQ ID NO 14
<211> LENGTH: 563
<212> TYPE: PRT
<213> ORGANISM: Saccharomyces cerevisiae

<400> SEQUENCE: 14

```
Met Ser Glu Ile Thr Leu Gly Lys Tyr Leu Phe Glu Arg Leu Lys Gln
1               5                   10                  15

Val Asn Val Asn Thr Val Phe Gly Leu Pro Gly Asp Phe Asn Leu Ser
            20                  25                  30

Leu Leu Asp Lys Ile Tyr Glu Val Glu Gly Met Arg Trp Ala Gly Asn
        35                  40                  45

Ala Asn Glu Leu Asn Ala Ala Tyr Ala Ala Asp Gly Tyr Ala Arg Ile
    50                  55                  60

Lys Gly Met Ser Cys Ile Ile Thr Thr Phe Gly Val Gly Glu Leu Ser
65                  70                  75                  80

Ala Leu Asn Gly Ile Ala Gly Ser Tyr Ala Glu His Val Gly Val Leu
```

```
                    85                  90                  95
His Val Val Gly Val Pro Ser Ile Ser Ala Gln Ala Lys Gln Leu Leu
                100                 105                 110
Leu His His Thr Leu Gly Asn Gly Asp Phe Thr Val Phe His Arg Met
                115                 120                 125
Ser Ala Asn Ile Ser Glu Thr Thr Ala Met Ile Thr Asp Ile Ala Thr
                130                 135                 140
Ala Pro Ala Glu Ile Asp Arg Cys Ile Arg Thr Thr Tyr Val Thr Gln
145                 150                 155                 160
Arg Pro Val Tyr Leu Gly Leu Pro Ala Asn Leu Val Asp Leu Asn Val
                165                 170                 175
Pro Ala Lys Leu Leu Gln Thr Pro Ile Asp Met Ser Leu Lys Pro Asn
                180                 185                 190
Asp Ala Glu Ser Glu Lys Glu Val Ile Asp Thr Ile Leu Ala Leu Val
                195                 200                 205
Lys Asp Ala Lys Asn Pro Val Ile Leu Ala Asp Ala Cys Cys Ser Arg
210                 215                 220
His Asp Val Lys Ala Glu Thr Lys Lys Leu Ile Asp Leu Thr Gln Phe
225                 230                 235                 240
Pro Ala Phe Val Thr Pro Met Gly Lys Gly Ser Ile Asp Glu Gln His
                245                 250                 255
Pro Arg Tyr Gly Gly Val Tyr Val Gly Thr Leu Ser Lys Pro Glu Val
                260                 265                 270
Lys Glu Ala Val Glu Ser Ala Asp Leu Ile Leu Ser Val Gly Ala Leu
                275                 280                 285
Leu Ser Asp Phe Asn Thr Gly Ser Phe Ser Tyr Ser Tyr Lys Thr Lys
                290                 295                 300
Asn Ile Val Glu Phe His Ser Asp His Met Lys Ile Arg Asn Ala Thr
305                 310                 315                 320
Phe Pro Gly Val Gln Met Lys Phe Val Leu Gln Lys Leu Leu Thr Thr
                325                 330                 335
Ile Ala Asp Ala Ala Lys Gly Tyr Lys Pro Val Ala Val Pro Ala Arg
                340                 345                 350
Thr Pro Ala Asn Ala Ala Val Pro Ala Ser Thr Pro Leu Lys Gln Glu
                355                 360                 365
Trp Met Trp Asn Gln Leu Gly Asn Phe Leu Gln Glu Gly Asp Val Val
                370                 375                 380
Ile Ala Glu Thr Gly Thr Ser Ala Phe Gly Ile Asn Gln Thr Thr Phe
385                 390                 395                 400
Pro Asn Asn Thr Tyr Gly Ile Ser Gln Val Leu Trp Gly Ser Ile Gly
                405                 410                 415
Phe Thr Thr Gly Ala Thr Leu Gly Ala Ala Phe Ala Ala Glu Glu Ile
                420                 425                 430
Asp Pro Lys Lys Arg Val Ile Leu Phe Ile Gly Asp Gly Ser Leu Gln
                435                 440                 445
Leu Thr Val Gln Glu Ile Ser Thr Met Ile Arg Trp Gly Leu Lys Pro
                450                 455                 460
Tyr Leu Phe Val Leu Asn Asn Asp Gly Tyr Thr Ile Glu Lys Leu Ile
465                 470                 475                 480
His Gly Pro Lys Ala Gln Tyr Asn Glu Ile Gln Gly Trp Asp His Leu
                485                 490                 495
Ser Leu Leu Pro Thr Phe Gly Ala Lys Asp Tyr Glu Thr His Arg Val
                500                 505                 510
```

```
Ala Thr Thr Gly Glu Trp Asp Lys Leu Thr Gln Asp Lys Ser Phe Asn
        515                 520                 525

Asp Asn Ser Lys Ile Arg Met Ile Glu Ile Met Leu Pro Val Phe Asp
        530                 535                 540

Ala Pro Gln Asn Leu Val Glu Gln Ala Lys Leu Thr Ala Ala Thr Asn
545                 550                 555                 560

Ala Lys Gln

<210> SEQ ID NO 15
<211> LENGTH: 1692
<212> TYPE: DNA
<213> ORGANISM: Saccharomyces cerevisiae

<400> SEQUENCE: 15
```

| | | | | | |
|---|---|---|---|---|---|
| atgtctgaaa | taaccttagg | taaatattta | tttgaaagat | tgagccaagt | caactgtaac | 60 |
| accgtcttcg | gtttgccagg | tgactttaac | ttgtctcttt | tggataagct | ttatgaagtc | 120 |
| aaaggtatga | gatgggctgg | taacgctaac | gaattgaacg | ctgcctatgc | tgctgatggt | 180 |
| tacgctcgta | tcaagggtat | gtcctgtatt | attaccacct | tcggtgttgg | tgaattgtct | 240 |
| gctttgaatg | gtattgccgg | ttcttacgct | gaacatgtcg | gtgttttgca | cgttgttggt | 300 |
| gttccatcca | tctcttctca | agctaagcaa | ttgttgttgc | atcataccct | gggtaacggt | 360 |
| gacttcactg | ttttccacag | aatgtctgcc | aacatttctg | aaaccactgc | catgatcact | 420 |
| gatattgcta | acgctccagc | tgaaattgac | agatgtatca | aaccaccta | cactacccaa | 480 |
| agaccagtct | acttgggttt | gccagctaac | ttggttgact | gaacgtccc | agccaagtta | 540 |
| ttggaaactc | caattgactt | gtctttgaag | ccaaacgacg | ctgaagctga | agctgaagtt | 600 |
| gttagaactg | ttgttgaatt | gatcaaggat | gctaagaacc | cagttatctt | ggctgatgct | 660 |
| tgtgcttcta | gacatgatgt | caaggctgaa | actaagaagt | tgatggactt | gactcaattc | 720 |
| ccagtttacg | tcaccccaat | gggtaagggt | gctattgacg | aacaacaccc | aagatacggt | 780 |
| ggtgtttacg | ttggtacctt | gtctagacca | gaagttaaga | aggctgtaga | atctgctgat | 840 |
| ttgatattgt | ctatcggtgc | tttgttgtct | gatttcaata | ccggttcttt | ctcttactcc | 900 |
| tacaagacca | aaaatatcgt | tgaattccac | tctgaccaca | tcaagatcag | aaacgccacc | 960 |
| ttcccaggtg | ttcaaatgaa | atttgccttg | caaaaattgt | tggatgctat | tccagaagtc | 1020 |
| gtcaaggact | acaaacctgt | tgctgtccca | gctagagttc | caattaccaa | gtctactcca | 1080 |
| gctaacactc | caatgaagca | agaatggatg | tggaaccatt | tgggtaactt | cttgagagaa | 1140 |
| ggtgatattg | ttattgctga | aaccggtact | tccgccttcg | gtattaacca | aactactttc | 1200 |
| ccaacagatg | tatacgctat | cgtccaagtc | ttgtggggtt | ccattggttt | cacagtcggc | 1260 |
| gctctattgg | gtgctactat | ggccgctgaa | gaacttgatc | aaagaagag | agttatttta | 1320 |
| ttcattggtg | acggttctct | acaattgact | gttcaagaaa | tctctaccat | gattagatgg | 1380 |
| ggtttgaagc | catacatttt | tgtcttgaat | aacaacggtt | acaccattga | aaaattgatt | 1440 |
| cacggtcctc | atgccgaata | taatgaaatt | caaggttggg | accacttggc | cttattgcca | 1500 |
| acttttggtg | ctagaaacta | cgaaacccac | agagttgcta | ccactggtga | atgggaaaag | 1560 |
| ttgactcaag | acaaggactt | ccaagacaac | tctaagatta | gaatgattga | agttatgttg | 1620 |
| ccagtctttg | atgctccaca | aaacttggtt | aaacaagctc | aattgactgc | cgctactaac | 1680 |
| gctaaacaat | aa | | | | | 1692 |

```
<210> SEQ ID NO 16
<211> LENGTH: 563
```

```
<212> TYPE: PRT
<213> ORGANISM: Saccharomyces cerevisiae

<400> SEQUENCE: 16

Met Ser Glu Ile Thr Leu Gly Lys Tyr Leu Phe Glu Arg Leu Ser Gln
1               5                   10                  15

Val Asn Cys Asn Thr Val Phe Gly Leu Pro Gly Asp Phe Asn Leu Ser
                20                  25                  30

Leu Leu Asp Lys Leu Tyr Glu Val Lys Gly Met Arg Trp Ala Gly Asn
            35                  40                  45

Ala Asn Glu Leu Asn Ala Ala Tyr Ala Ala Asp Gly Tyr Ala Arg Ile
        50                  55                  60

Lys Gly Met Ser Cys Ile Ile Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95

His Val Val Gly Val Pro Ser Ile Ser Ser Gln Ala Lys Gln Leu Leu
                100                 105                 110

Leu His His Thr Leu Gly Asn Gly Asp Phe Thr Val Phe His Arg Met
            115                 120                 125

Ser Ala Asn Ile Ser Glu Thr Thr Ala Met Ile Thr Asp Ile Ala Asn
        130                 135                 140

Ala Pro Ala Glu Ile Asp Arg Cys Ile Arg Thr Thr Tyr Thr Thr Gln
145                 150                 155                 160

Arg Pro Val Tyr Leu Gly Leu Pro Ala Asn Leu Val Asp Leu Asn Val
                165                 170                 175

Pro Ala Lys Leu Leu Glu Thr Pro Ile Asp Leu Ser Leu Lys Pro Asn
                180                 185                 190

Asp Ala Glu Ala Glu Ala Glu Val Val Arg Thr Val Val Glu Leu Ile
            195                 200                 205

Lys Asp Ala Lys Asn Pro Val Ile Leu Ala Asp Ala Cys Ala Ser Arg
210                 215                 220

His Asp Val Lys Ala Glu Thr Lys Lys Leu Met Asp Leu Thr Gln Phe
225                 230                 235                 240

Pro Val Tyr Val Thr Pro Met Gly Lys Gly Ala Ile Asp Glu Gln His
                245                 250                 255

Pro Arg Tyr Gly Gly Val Tyr Val Gly Thr Leu Ser Arg Pro Glu Val
                260                 265                 270

Lys Lys Ala Val Glu Ser Ala Asp Leu Ile Leu Ser Ile Gly Ala Leu
            275                 280                 285

Leu Ser Asp Phe Asn Thr Gly Ser Phe Ser Tyr Ser Tyr Lys Thr Lys
        290                 295                 300

Asn Ile Val Glu Phe His Ser Asp His Ile Lys Ile Arg Asn Ala Thr
305                 310                 315                 320

Phe Pro Gly Val Gln Met Lys Phe Ala Leu Gln Lys Leu Leu Asp Ala
                325                 330                 335

Ile Pro Glu Val Val Lys Asp Tyr Lys Pro Val Ala Val Pro Ala Arg
                340                 345                 350

Val Pro Ile Thr Lys Ser Thr Pro Ala Asn Thr Pro Met Lys Gln Glu
            355                 360                 365

Trp Met Trp Asn His Leu Gly Asn Phe Leu Arg Glu Gly Asp Ile Val
370                 375                 380

Ile Ala Glu Thr Gly Thr Ser Ala Phe Gly Ile Asn Gln Thr Thr Phe
385                 390                 395                 400
```

```
Pro Thr Asp Val Tyr Ala Ile Val Gln Val Leu Trp Gly Ser Ile Gly
                405                 410                 415
Phe Thr Val Gly Ala Leu Leu Gly Ala Thr Met Ala Ala Glu Leu
            420                 425                 430
Asp Pro Lys Lys Arg Val Ile Leu Phe Ile Gly Asp Gly Ser Leu Gln
            435                 440                 445
Leu Thr Val Gln Glu Ile Ser Thr Met Ile Arg Trp Gly Leu Lys Pro
450                 455                 460
Tyr Ile Phe Val Leu Asn Asn Asn Gly Tyr Thr Ile Glu Lys Leu Ile
465                 470                 475                 480
His Gly Pro His Ala Glu Tyr Asn Glu Ile Gln Gly Trp Asp His Leu
                485                 490                 495
Ala Leu Leu Pro Thr Phe Gly Ala Arg Asn Tyr Glu Thr His Arg Val
            500                 505                 510
Ala Thr Thr Gly Glu Trp Glu Lys Leu Thr Gln Asp Lys Asp Phe Gln
            515                 520                 525
Asp Asn Ser Lys Ile Arg Met Ile Glu Val Met Leu Pro Val Phe Asp
            530                 535                 540
Ala Pro Gln Asn Leu Val Lys Gln Ala Gln Leu Thr Ala Ala Thr Asn
545                 550                 555                 560
Ala Lys Gln
```

<210> SEQ ID NO 17
<211> LENGTH: 1692
<212> TYPE: DNA
<213> ORGANISM: Saccharomyces cerevisiae

<400> SEQUENCE: 17

```
atgtctgaaa ttactcttgg aaaatactta tttgaaagat tgaagcaagt taatgttaac      60
accattttg  ggctaccagg cgacttcaac ttgtccctat tggacaagat ttacgaggta     120
gatggattga gatgggctgg taatgcaaat gagctgaacg ccgcctatgc cgccgatggt     180
tacgcacgca tcaagggttt atctgtgctg gtaactactt ttggcgtagg tgaattatcc     240
gccttgaatg gtattgcagg atcgtatgca gaacacgtcg gtgtactgca tgttgttggt     300
gtcccctcta tctccgctca ggctaagcaa ttgttgttgc atcatacctt gggtaacggt     360
gattttaccg ttttcacag  aatgtccgcc aatatctcag aaactacatc aatgattaca     420
gacattgcta cagccccttc agaaatcgat aggttgatca ggacaacatt tataacacaa     480
aggcctagct acttggggtt gccagcgaat ttggtagatc taaggttcc  tggttctctt     540
ttggaaaaac cgattgatct atcattaaaa cctaacgatc ccgaagctga aaaggaagtt     600
attgataccg tactagaatt gatccagaat tcgaaaaacc tgttatact  atcggatgcc     660
tgtgcttcta ggcacaacgt taaaaaagaa acccagaagt taattgattt gacgcaattc     720
ccagcttttg tgacacctct aggtaaaggg tcaatagatg aacagcatcc cagatatggc     780
ggtgtttatg tgggaacgct gtccaaacaa gacgtgaaac aggccgttga gtcggctgat     840
ttgatccttt cggtcggtgc tttgctctct gatttttaaca caggttcgtt ttcctactcc     900
tacaagacta aaaatgtagt ggagtttcat tccgattacg taaaggtgaa gaacgctacg     960
ttcctcggtg tacaaatgaa atttgcacta caaaacttac tgaaggttat tcccgatgtt    1020
gttaagggct acaagagcgt tcccgtacca accaaaactc ccgcaaacaa aggtgtacct    1080
gctagcacgc ccttgaaaca agagtggttg tggaacgaat gtccaaatt  cttgcaagaa    1140
ggtgatgtta tcatttccga gaccggcacg tctgccttcg gtatcaatca aactatcttt    1200
```

-continued

```
cctaaggacg cctacggtat ctcgcaggtg ttgtgggggt ccatcggttt tacaacagga    1260
gcaactttag gtgctgcctt tgccgctgag gagattgacc ccaacaagag agtcatctta    1320
ttcataggtg acgggtcttt gcagttaacc gtccaagaaa tctccaccat gatcagatgg    1380
gggttaaagc cgtatctttt tgtccttaac aacgacggct acactatcga aaagctgatt    1440
catgggcctc acgcagagta caacgaaatc cagacctggg atcacctcgc cctgttgccc    1500
gcatttggtg cgaaaagta cgaaaatcac aagatcgcca ctacgggtga gtgggatgcc    1560
ttaaccactg attcagagtt ccagaaaaac tcggtgatca gactaattga actgaaactg    1620
cccgtctttg atgctccgga aagtttgatc aaacaagcgc aattgactgc cgctacaaat    1680
gccaaacaat aa                                                        1692
```

<210> SEQ ID NO 18
<211> LENGTH: 563
<212> TYPE: PRT
<213> ORGANISM: Saccharomyces cerevisiae

<400> SEQUENCE: 18

```
Met Ser Glu Ile Thr Leu Gly Lys Tyr Leu Phe Glu Arg Leu Lys Gln
1               5                   10                  15

Val Asn Val Asn Thr Ile Phe Gly Leu Pro Gly Asp Phe Asn Leu Ser
            20                  25                  30

Leu Leu Asp Lys Ile Tyr Glu Val Asp Gly Leu Arg Trp Ala Gly Asn
        35                  40                  45

Ala Asn Glu Leu Asn Ala Ala Tyr Ala Ala Asp Gly Tyr Ala Arg Ile
    50                  55                  60

Lys Gly Leu Ser Val Leu Val Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95

His Val Val Gly Val Pro Ser Ile Ser Ala Gln Ala Lys Gln Leu Leu
            100                 105                 110

Leu His His Thr Leu Gly Asn Gly Asp Phe Thr Val Phe His Arg Met
        115                 120                 125

Ser Ala Asn Ile Ser Glu Thr Thr Ser Met Ile Thr Asp Ile Ala Thr
130                 135                 140

Ala Pro Ser Glu Ile Asp Arg Leu Ile Arg Thr Thr Phe Ile Thr Gln
145                 150                 155                 160

Arg Pro Ser Tyr Leu Gly Leu Pro Ala Asn Leu Val Asp Leu Lys Val
                165                 170                 175

Pro Gly Ser Leu Leu Glu Lys Pro Ile Asp Leu Ser Leu Lys Pro Asn
            180                 185                 190

Asp Pro Glu Ala Glu Lys Glu Val Ile Asp Thr Val Leu Glu Leu Ile
        195                 200                 205

Gln Asn Ser Lys Asn Pro Val Ile Leu Ser Asp Ala Cys Ala Ser Arg
    210                 215                 220

His Asn Val Lys Lys Glu Thr Gln Lys Leu Ile Asp Leu Thr Gln Phe
225                 230                 235                 240

Pro Ala Phe Val Thr Pro Leu Gly Lys Gly Ser Ile Asp Glu Gln His
                245                 250                 255

Pro Arg Tyr Gly Gly Val Tyr Val Gly Thr Leu Ser Lys Gln Asp Val
            260                 265                 270

Lys Gln Ala Val Glu Ser Ala Asp Leu Ile Leu Ser Val Gly Ala Leu
        275                 280                 285
```

| | | | | | | | | | | | | |
|---|---|---|---|---|---|---|---|---|---|---|---|---|
|Leu|Ser|Asp|Phe|Asn|Thr|Gly|Ser|Phe|Ser|Tyr|Ser|Tyr|Lys|Thr|Lys|
| |290| | | |295| | | |300| | | | | | |

Leu Ser Asp Phe Asn Thr Gly Ser Phe Ser Tyr Ser Tyr Lys Thr Lys
    290                 295                 300

Asn Val Val Glu Phe His Ser Asp Tyr Val Lys Val Lys Asn Ala Thr
305                 310                 315                 320

Phe Leu Gly Val Gln Met Lys Phe Ala Leu Gln Asn Leu Leu Lys Val
                325                 330                 335

Ile Pro Asp Val Val Lys Gly Tyr Lys Ser Val Pro Val Pro Thr Lys
                340                 345                 350

Thr Pro Ala Asn Lys Gly Val Pro Ala Ser Thr Pro Leu Lys Gln Glu
            355                 360                 365

Trp Leu Trp Asn Glu Leu Ser Lys Phe Leu Gln Glu Gly Asp Val Ile
370                 375                 380

Ile Ser Glu Thr Gly Thr Ser Ala Phe Gly Ile Asn Gln Thr Ile Phe
385                 390                 395                 400

Pro Lys Asp Ala Tyr Gly Ile Ser Gln Val Leu Trp Gly Ser Ile Gly
                405                 410                 415

Phe Thr Thr Gly Ala Thr Leu Gly Ala Ala Phe Ala Ala Glu Ile
                420                 425                 430

Asp Pro Asn Lys Arg Val Ile Leu Phe Ile Gly Asp Gly Ser Leu Gln
            435                 440                 445

Leu Thr Val Gln Glu Ile Ser Thr Met Ile Arg Trp Gly Leu Lys Pro
450                 455                 460

Tyr Leu Phe Val Leu Asn Asn Asp Gly Tyr Thr Ile Glu Lys Leu Ile
465                 470                 475                 480

His Gly Pro His Ala Glu Tyr Asn Glu Ile Gln Thr Trp Asp His Leu
                485                 490                 495

Ala Leu Leu Pro Ala Phe Gly Ala Lys Lys Tyr Glu Asn His Lys Ile
            500                 505                 510

Ala Thr Thr Gly Glu Trp Asp Ala Leu Thr Thr Asp Ser Glu Phe Gln
            515                 520                 525

Lys Asn Ser Val Ile Arg Leu Ile Glu Leu Lys Leu Pro Val Phe Asp
            530                 535                 540

Ala Pro Glu Ser Leu Ile Lys Gln Ala Gln Leu Thr Ala Ala Thr Asn
545                 550                 555                 560

Ala Lys Gln

<210> SEQ ID NO 19
<211> LENGTH: 1908
<212> TYPE: DNA
<213> ORGANISM: Saccharomyces cerevisiae

<400> SEQUENCE: 19

```
atggcacctg ttacaattga aaagttcgta aatcaagaag aacgacacct tgtttccaac      60
cgatcagcaa caattccgtt tggtgaatac atatttaaaa gattgttgtc catcgatacg     120
aaatcagttt tcggtgttcc tggtgacttc aacttatctc tattagaata tctctattca     180
cctagtgttg aatcagctgg cctaagatgg gtcggcacgt gtaatgaact gaacgccgct     240
tatgcggccg acggatattc ccgttactct aataagattg ctgtttaat aaccacgtat     300 ggcgttggtg aattaagcgc cttgaacggt atagccggtt cgttcgctga aatgtcaaa     360 gttttgcaca ttgttggtgt ggccaagtcc atagattcgc gttcaagtaa ctttagtgat     420
cggaacctac atcatttggt cccacagcta catgattcaa attttaaagg gccaaatcat     480
aaagtatatc atgatatggt aaaagatga gtcgcttgct cggtagccta cttggaggat     540
attgaaactg catgtgacca agtcgataat gttatccgcg atatttacaa gtattctaaa    600
```

```
cctggttata ttttttgttcc tgcagatttt gcggatatgt ctgttacatg tgataatttg    660
gttaatgttc cacgtatatc tcaacaagat tgtatagtat acccttctga aaaccaattg    720
tctgacataa tcaacaagat tactagttgg atatattcca gtaaaacacc tgcgatcctt    780
ggagacgtac tgactgatag gtatggtgtg agtaactttt tgaacaagct tatctgcaaa    840
actgggattt ggaatttttc cactgttatg ggaaaatctg taattgatga gtcaaaccca    900
acttatatgg gtcaatataa tggtaaagaa ggtttaaaac aagtctatga acattttgaa    960
ctgtgcgact tggtcttgca ttttggagtc gacatcaatg aaattaataa tgggcattat   1020
acttttactt ataaaccaaa tgctaaaatc attcaatttc atccgaatta tattcgcctt   1080
gtggacacta gcagggcaa tgagcaaatg ttcaaaggaa tcaattttgc ccctattta    1140 aaagaactat acaagcgcat tgacgtttct aaactttctt tgcaatatga ttcaaatgta   1200
actcaatata cgaacgaaac aatgcggtta gaagatccta ccaatggaca atcaagcatt   1260
attacacaag ttcacttaca aaagacgatg cctaaatttt tgaaccctgg tgatgttgtc   1320
gtttgtgaaa caggctcttt tcaattctct gttcgtgatt tcgcgtttcc ttcgcaatta   1380
aaatatatat cgcaaggatt tttcctttcc attggcatgg cccttcctgc cgccctaggt   1440
gttggaattg ccatgcaaga ccactcaaac gctcacatca atggtggcaa cgtaaaagag   1500
gactataagc caagattaat tttgtttgaa ggtgacggtg cagcacagat gacaatccaa   1560
gaactgagca ccattctgaa gtgcaatatt ccactagaag ttatcatttg gaacaataac   1620
ggctacacta ttgaaagagc catcatgggc cctaccaggt cgtataacga cgttatgtct   1680
tggaaatgga ccaaactatt tgaagcattc ggagacttcg acggaaagta tactaatagc   1740
actctcattc aatgtccctc taaattagca ctgaaattgg aggagcttaa gaattcaaac   1800
aaaagaagcg ggatagaact tttagaagtc aaattaggcg aattggattt ccccgaacag   1860
ctaaagtgca tggttgaagc agcggcactt aaaagaaata aaaaatag              1908
```

<210> SEQ ID NO 20
<211> LENGTH: 635
<212> TYPE: PRT
<213> ORGANISM: Saccharomyces cerevisiae

<400> SEQUENCE: 20

```
Met Ala Pro Val Thr Ile Glu Lys Phe Val Asn Gln Glu Glu Arg His
1               5                   10                  15

Leu Val Ser Asn Arg Ser Ala Thr Ile Pro Phe Gly Glu Tyr Ile Phe
            20                  25                  30

Lys Arg Leu Leu Ser Ile Asp Thr Lys Ser Val Phe Gly Val Pro Gly
        35                  40                  45

Asp Phe Asn Leu Ser Leu Leu Glu Tyr Leu Tyr Ser Pro Ser Val Glu
    50                  55                  60

Ser Ala Gly Leu Arg Trp Val Gly Thr Cys Asn Glu Leu Asn Ala Ala
65                  70                  75                  80

Tyr Ala Ala Asp Gly Tyr Ser Arg Tyr Ser Asn Lys Ile Gly Cys Leu
                85                  90                  95

Ile Thr Thr Tyr Gly Val Gly Glu Leu Ser Ala Leu Asn Gly Ile Ala
            100                 105                 110

Gly Ser Phe Ala Glu Asn Val Lys Val Leu His Ile Val Gly Val Ala
        115                 120                 125

Lys Ser Ile Asp Ser Arg Ser Ser Asn Phe Ser Asp Arg Asn Leu His
    130                 135                 140
```

-continued

His Leu Val Pro Gln Leu His Asp Ser Asn Phe Lys Gly Pro Asn His
145                 150                 155                 160

Lys Val Tyr His Asp Met Val Lys Asp Arg Val Ala Cys Ser Val Ala
            165                 170                 175

Tyr Leu Glu Asp Ile Glu Thr Ala Cys Asp Gln Val Asp Asn Val Ile
            180                 185                 190

Arg Asp Ile Tyr Lys Tyr Ser Lys Pro Gly Tyr Ile Phe Val Pro Ala
            195                 200                 205

Asp Phe Ala Asp Met Ser Val Thr Cys Asp Asn Leu Val Asn Val Pro
210                 215                 220

Arg Ile Ser Gln Gln Asp Cys Ile Val Tyr Pro Ser Glu Asn Gln Leu
225                 230                 235                 240

Ser Asp Ile Ile Asn Lys Ile Thr Ser Trp Ile Tyr Ser Ser Lys Thr
            245                 250                 255

Pro Ala Ile Leu Gly Asp Val Leu Thr Asp Arg Tyr Gly Val Ser Asn
            260                 265                 270

Phe Leu Asn Lys Leu Ile Cys Lys Thr Gly Ile Trp Asn Phe Ser Thr
            275                 280                 285

Val Met Gly Lys Ser Val Ile Asp Glu Ser Asn Pro Thr Tyr Met Gly
290                 295                 300

Gln Tyr Asn Gly Lys Glu Gly Leu Lys Gln Val Tyr Glu His Phe Glu
305                 310                 315                 320

Leu Cys Asp Leu Val Leu His Phe Gly Val Asp Ile Asn Glu Ile Asn
            325                 330                 335

Asn Gly His Tyr Thr Phe Thr Tyr Lys Pro Asn Ala Lys Ile Ile Gln
            340                 345                 350

Phe His Pro Asn Tyr Ile Arg Leu Val Asp Thr Arg Gln Gly Asn Glu
            355                 360                 365

Gln Met Phe Lys Gly Ile Asn Phe Ala Pro Ile Leu Lys Glu Leu Tyr
            370                 375                 380

Lys Arg Ile Asp Val Ser Lys Leu Ser Leu Gln Tyr Asp Ser Asn Val
385                 390                 395                 400

Thr Gln Tyr Thr Asn Glu Thr Met Arg Leu Glu Asp Pro Thr Asn Gly
            405                 410                 415

Gln Ser Ser Ile Ile Thr Gln Val His Leu Gln Lys Thr Met Pro Lys
            420                 425                 430

Phe Leu Asn Pro Gly Asp Val Val Cys Glu Thr Gly Ser Phe Gln
            435                 440                 445

Phe Ser Val Arg Asp Phe Ala Phe Pro Ser Gln Leu Lys Tyr Ile Ser
            450                 455                 460

Gln Gly Phe Phe Leu Ser Ile Gly Met Ala Leu Pro Ala Ala Leu Gly
465                 470                 475                 480

Val Gly Ile Ala Met Gln Asp His Ser Asn Ala His Ile Asn Gly Gly
            485                 490                 495

Asn Val Lys Glu Asp Tyr Lys Pro Arg Leu Ile Leu Phe Glu Gly Asp
            500                 505                 510

Gly Ala Ala Gln Met Thr Ile Gln Glu Leu Ser Thr Ile Leu Lys Cys
            515                 520                 525

Asn Ile Pro Leu Glu Val Ile Ile Trp Asn Asn Gly Tyr Thr Ile
            530                 535                 540

Glu Arg Ala Ile Met Gly Pro Thr Arg Ser Tyr Asn Asp Val Met Ser
545                 550                 555                 560

Trp Lys Trp Thr Lys Leu Phe Glu Ala Phe Gly Asp Phe Asp Gly Lys
            565                 570                 575

Tyr Thr Asn Ser Thr Leu Ile Gln Cys Pro Ser Lys Leu Ala Leu Lys
            580                 585                 590

Leu Glu Glu Leu Lys Asn Ser Asn Lys Arg Ser Gly Ile Glu Leu Leu
        595                 600                 605

Glu Val Lys Leu Gly Glu Leu Asp Phe Pro Glu Gln Leu Lys Cys Met
    610                 615                 620

Val Glu Ala Ala Ala Leu Lys Arg Asn Lys Lys
625                 630                 635

<210> SEQ ID NO 21
<211> LENGTH: 1830
<212> TYPE: DNA
<213> ORGANISM: Saccharomyces cerevisiae

<400> SEQUENCE: 21

| | | | | | |
|---|---|---|---|---|---|
| atgaattcta | gctatacaca | gagatatgca | ctgccgaagt | gtatagcaat | atcagattat | 60 |
| cttttccatc | ggctcaacca | gctgaacata | cataccatat | ttggactctc | cggagaattt | 120 |
| agcatgccgt | tgctggataa | actatacaac | attccgaact | tacgatgggc | cggtaattct | 180 |
| aatgagttaa | atgctgccta | cgcagcagat | ggatactcac | gactaaaagg | cttgggatgt | 240 |
| ctcataacaa | cctttggtgt | aggcgaatta | tcggcaatca | atggcgtggc | cggatcttac | 300 |
| gctgaacatg | taggaatact | tcacatagtg | ggtatgccgc | caacaagtgc | acaaacgaaa | 360 |
| caactactac | tgcatcatac | tctgggcaat | ggtgatttca | cggtatttca | tagaatagcc | 420 |
| agtgatgtag | catgctatac | aacattgatt | attgactctg | aattatgtgc | cgacgaagtc | 480 |
| gataagtgca | tcaaaaaggc | ttggatagaa | cagaggccag | tatacatggg | catgcctgtc | 540 |
| aaccaggtaa | atctcccgat | tgaatcagca | aggcttaata | cacctctgga | tttacaattg | 600 |
| cataaaaacg | acccagacgt | agagaaagaa | gttatttctc | gaatattgag | ttttatatac | 660 |
| aaaagccaga | atccggcaat | catcgtagat | gcatgtacta | gtcgacagaa | tttaatcgag | 720 |
| gagactaaag | agctttgtaa | taggcttaaa | tttccagttt | ttgttacacc | tatgggtaag | 780 |
| ggtacagtaa | acgaaacaga | cccgcaattt | ggggcgtat | tcacgggctc | gatatcagcc | 840 |
| ccagaagtaa | gagaagtagt | tgattttgcc | gattttatca | tcgtcattgg | ttgcatgctc | 900 |
| tccgaattca | gcacgtcaac | tttccacttc | aatataaaa | ctaagaattg | tgcgctacta | 960 |
| tattctacat | ctgtgaaatt | gaaaaatgcc | acatatcctg | acttgagcat | taaattacta | 1020 |
| ctacagaaaa | tattagcaaa | tcttgatgaa | tctaaactgt | cttaccaacc | aagcgaacaa | 1080 |
| cccagtatga | tggttccaag | accttaccca | gcaggaaatg | tcctcttgag | acaagaatgg | 1140 |
| gtctggaatg | aaatatccca | ttggttccaa | ccaggtgaca | taatcataac | agaaactggt | 1200 |
| gcttctgcat | ttggagttaa | ccagaccaga | tttccggtaa | atacactagg | tatttcgcaa | 1260 |
| gctctttggg | gatctgtcgg | atatacaatg | ggggcgtgtc | ttggggcaga | atttgctgtt | 1320 |
| caagagataa | acaaggataa | aattccccgca | actaaacata | gagttattct | gtttatgggt | 1380 |
| gacggtgctt | tccaattgac | agttcaagaa | ttatccacaa | ttgttaagtg | gggattgaca | 1440 |
| ccttatattt | ttgtgatgaa | taccaaggt | tactctgtgg | acaggttttt | gcatcacagg | 1500 |
| tcagatgcta | ttattacga | tatccaacct | tggaactact | tgggattatt | gcgagtattt | 1560 |
| ggttgcacga | actacgaaac | gaaaaaaatt | attactgttg | gagaattcag | atccatgatc | 1620 |
| agtgacccaa | actttgcgac | caatgacaaa | attcggatga | tagagattat | gctaccacca | 1680 |
| agggatgttc | cacaggctct | gcttgacagg | tgggtgtag | aaaaagaaca | gagcaaacaa | 1740 |
| gtgcaagagg | agaacgaaaa | ttctagcgca | gtaaatacgc | caactccaga | attccaacca | 1800 | cttctaaaaa aaaatcaagt tggatactga                                                      1830

<210> SEQ ID NO 22
<211> LENGTH: 609
<212> TYPE: PRT
<213> ORGANISM: Saccharomyces cerevisiae

<400> SEQUENCE: 22

Met Asn Ser Ser Tyr Thr Gln Arg Tyr Ala Leu Pro Lys Cys Ile Ala
1               5                   10                  15

Ile Ser Asp Tyr Leu Phe His Arg Leu Asn Gln Leu Asn Ile His Thr
            20                  25                  30

Ile Phe Gly Leu Ser Gly Glu Phe Ser Met Pro Leu Leu Asp Lys Leu
        35                  40                  45

Tyr Asn Ile Pro Asn Leu Arg Trp Ala Gly Asn Ser Asn Glu Leu Asn
    50                  55                  60

Ala Ala Tyr Ala Ala Asp Gly Tyr Ser Arg Leu Lys Gly Leu Gly Cys
65                  70                  75                  80

Leu Ile Thr Thr Phe Gly Val Gly Glu Leu Ser Ala Ile Asn Gly Val
                85                  90                  95

Ala Gly Ser Tyr Ala Glu His Val Gly Ile Leu His Ile Val Gly Met
            100                 105                 110

Pro Pro Thr Ser Ala Gln Thr Lys Gln Leu Leu Leu His His Thr Leu
        115                 120                 125

Gly Asn Gly Asp Phe Thr Val Phe His Arg Ile Ala Ser Asp Val Ala
    130                 135                 140

Cys Tyr Thr Thr Leu Ile Ile Asp Ser Glu Leu Cys Ala Asp Glu Val
145                 150                 155                 160

Asp Lys Cys Ile Lys Lys Ala Trp Ile Glu Gln Arg Pro Val Tyr Met
                165                 170                 175

Gly Met Pro Val Asn Gln Val Asn Leu Pro Ile Glu Ser Ala Arg Leu
            180                 185                 190

Asn Thr Pro Leu Asp Leu Gln Leu His Lys Asn Asp Pro Asp Val Glu
        195                 200                 205

Lys Glu Val Ile Ser Arg Ile Leu Ser Phe Ile Tyr Lys Ser Gln Asn
    210                 215                 220

Pro Ala Ile Ile Val Asp Ala Cys Thr Ser Arg Gln Asn Leu Ile Glu
225                 230                 235                 240

Glu Thr Lys Glu Leu Cys Asn Arg Leu Lys Phe Pro Val Phe Val Thr
                245                 250                 255

Pro Met Gly Lys Gly Thr Val Asn Glu Thr Asp Pro Gln Phe Gly Gly
            260                 265                 270

Val Phe Thr Gly Ser Ile Ser Ala Pro Glu Val Arg Glu Val Val Asp
        275                 280                 285

Phe Ala Asp Phe Ile Ile Val Ile Gly Cys Met Leu Ser Glu Phe Ser
    290                 295                 300

Thr Ser Thr Phe His Phe Gln Tyr Lys Thr Lys Asn Cys Ala Leu Leu
305                 310                 315                 320

Tyr Ser Thr Ser Val Lys Leu Lys Asn Ala Thr Tyr Pro Asp Leu Ser
                325                 330                 335

Ile Lys Leu Leu Leu Gln Lys Ile Leu Ala Asn Leu Asp Glu Ser Lys
            340                 345                 350

Leu Ser Tyr Gln Pro Ser Glu Gln Pro Ser Met Met Val Pro Arg Pro
        355                 360                 365

```
Tyr Pro Ala Gly Asn Val Leu Leu Arg Gln Glu Trp Val Trp Asn Glu
        370                 375                 380

Ile Ser His Trp Phe Gln Pro Gly Asp Ile Ile Thr Glu Thr Gly
385                 390                 395                 400

Ala Ser Ala Phe Gly Val Asn Gln Thr Arg Phe Pro Val Asn Thr Leu
                405                 410                 415

Gly Ile Ser Gln Ala Leu Trp Gly Ser Val Gly Tyr Thr Met Gly Ala
                420                 425                 430

Cys Leu Gly Ala Glu Phe Ala Val Gln Glu Ile Asn Lys Asp Lys Phe
            435                 440                 445

Pro Ala Thr Lys His Arg Val Ile Leu Phe Met Gly Asp Gly Ala Phe
        450                 455                 460

Gln Leu Thr Val Gln Glu Leu Ser Thr Ile Val Lys Trp Gly Leu Thr
465                 470                 475                 480

Pro Tyr Ile Phe Val Met Asn Asn Gln Gly Tyr Ser Val Asp Arg Phe
                485                 490                 495

Leu His His Arg Ser Asp Ala Ser Tyr Tyr Asp Ile Gln Pro Trp Asn
                500                 505                 510

Tyr Leu Gly Leu Leu Arg Val Phe Gly Cys Thr Asn Tyr Glu Thr Lys
            515                 520                 525

Lys Ile Ile Thr Val Gly Glu Phe Arg Ser Met Ile Ser Asp Pro Asn
        530                 535                 540

Phe Ala Thr Asn Asp Lys Ile Arg Met Ile Glu Ile Met Leu Pro Pro
545                 550                 555                 560

Arg Asp Val Pro Gln Ala Leu Leu Asp Arg Trp Val Val Glu Lys Glu
                565                 570                 575

Gln Ser Lys Gln Val Gln Glu Glu Asn Glu Asn Ser Ser Ala Val Asn
            580                 585                 590

Thr Pro Thr Pro Glu Phe Gln Pro Leu Leu Lys Lys Asn Gln Val Gly
        595                 600                 605

Tyr

<210> SEQ ID NO 23
<211> LENGTH: 1047
<212> TYPE: DNA
<213> ORGANISM: Saccharomyces cerevisiae

<400> SEQUENCE: 23
atgtctatcc cagaaactca aaaggtgtt atcttctacg aatcccacgg taagttggaa      60
tacaaagata ttccagttcc aaagccaaag ccaacgaat tgttgatcaa cgttaaatac    120
tctggtgtct gtcacactga cttgcacgct tggcacggtg actggccatt gccagttaag    180
ctaccattag tcggtggtca cgaaggtgcc ggtgtcgttg tcggcatggg tgaaaacgtt    240
aagggctgga gatcggtga ctacgccggt atcaaatggt tgaacggttc ttgtatggcc    300
tgtgaatact gtgaattggg taacgaatcc aactgtcctc acgctgactt gtctggttac    360
acccacgacg ttctcttcca acaatacgct accgctgacg ctgttcaagc cgctcacatt    420
cctcaaggta ccgacttggc ccaagtcgcc cccatcttgt gtgctggtat caccgtctac    480
aaggctttga gtctgctaa cttgatggcc ggtcactggg ttgctatctc cggtgctgct    540
ggtggtctag gttcttggc tgttcaatac gccaaggcta tgggttacag agtcttgggt    600
attgacggtg gtgaaggtaa ggaagaatta ttcagatcca tcggtggtga agtcttcatt    660
gacttcacta aggaaaagga cattgtcggt gctgttctaa aggccactga cggtggtgct    720
cacggtgtca tcaacgtttc cgtttccgaa gccgctattg aagcttctac cagatacgtt    780
```

-continued

```
agagctaacg gtaccaccgt tttggtcggt atgccagctg gtgccaagtg ttgttctgat    840
gtcttcaacc aagtcgtcaa gtccatctct attgttggtt cttacgtcgg taacagagct    900
gacaccagag aagctttgga cttcttcgcc agaggtttgg tcaagtctcc aatcaaggtt    960
gtcggcttgt ctaccttgcc agaaatttac gaaaagatgg aaaagggtca aatcgttggt   1020
agatacgttg ttgacacttc taaataa                                         1047
```

<210> SEQ ID NO 24
<211> LENGTH: 348
<212> TYPE: PRT
<213> ORGANISM: Saccharomyces cerevisiae

<400> SEQUENCE: 24

```
Met Ser Ile Pro Glu Thr Gln Lys Gly Val Ile Phe Tyr Glu Ser His
1               5                   10                  15

Gly Lys Leu Glu Tyr Lys Asp Ile Pro Val Pro Lys Pro Lys Ala Asn
                20                  25                  30

Glu Leu Leu Ile Asn Val Lys Tyr Ser Gly Val Cys His Thr Asp Leu
            35                  40                  45

His Ala Trp His Gly Asp Trp Pro Leu Pro Val Lys Leu Pro Leu Val
        50                  55                  60

Gly Gly His Glu Gly Ala Gly Val Val Val Gly Met Gly Glu Asn Val
65                  70                  75                  80

Lys Gly Trp Lys Ile Gly Asp Tyr Ala Gly Ile Lys Trp Leu Asn Gly
                85                  90                  95

Ser Cys Met Ala Cys Glu Tyr Cys Glu Leu Gly Asn Glu Ser Asn Cys
            100                 105                 110

Pro His Ala Asp Leu Ser Gly Tyr Thr His Asp Gly Ser Phe Gln Gln
        115                 120                 125

Tyr Ala Thr Ala Asp Ala Val Gln Ala Ala His Ile Pro Gln Gly Thr
130                 135                 140

Asp Leu Ala Gln Val Ala Pro Ile Leu Cys Ala Gly Ile Thr Val Tyr
145                 150                 155                 160

Lys Ala Leu Lys Ser Ala Asn Leu Met Ala Gly His Trp Val Ala Ile
                165                 170                 175

Ser Gly Ala Ala Gly Gly Leu Gly Ser Leu Ala Val Gln Tyr Ala Lys
            180                 185                 190

Ala Met Gly Tyr Arg Val Leu Gly Ile Asp Gly Gly Glu Gly Lys Glu
        195                 200                 205

Glu Leu Phe Arg Ser Ile Gly Gly Glu Val Phe Ile Asp Phe Thr Lys
210                 215                 220

Glu Lys Asp Ile Val Gly Ala Val Leu Lys Ala Thr Asp Gly Gly Ala
225                 230                 235                 240

His Gly Val Ile Asn Val Ser Val Ser Glu Ala Ala Ile Glu Ala Ser
                245                 250                 255

Thr Arg Tyr Val Arg Ala Asn Gly Thr Thr Val Leu Val Gly Met Pro
            260                 265                 270

Ala Gly Ala Lys Cys Cys Ser Asp Val Phe Asn Gln Val Val Lys Ser
        275                 280                 285

Ile Ser Ile Val Gly Ser Tyr Val Gly Asn Arg Ala Asp Thr Arg Glu
        290                 295                 300

Ala Leu Asp Phe Phe Ala Arg Gly Leu Val Lys Ser Pro Ile Lys Val
305                 310                 315                 320

Val Gly Leu Ser Thr Leu Pro Glu Ile Tyr Glu Lys Met Glu Lys Gly
```

```
                    325                 330                 335
Gln Ile Val Gly Arg Tyr Val Val Asp Thr Ser Lys
                340                 345

<210> SEQ ID NO 25
<211> LENGTH: 1047
<212> TYPE: DNA
<213> ORGANISM: Saccharomyces cerevisiae

<400> SEQUENCE: 25
atgtctattc cagaaactca aaaagccatt atcttctacg aatccaacgg caagttggag      60
cataaggata tcccagttcc aaagccaaag cccaacgaat tgttaatcaa cgtcaagtac     120
tctggtgtct gccacaccga tttgcacgct tggcatggtg actggccatt gccaactaag     180
ttaccattag ttggtggtca cgaaggtgcc ggtgtcgttg tcggcatggg tgaaaacgtt     240
aagggctgga gatcggtga ctacgccggt atcaaatggt tgaacggttc ttgtatggcc      300
tgtgaatact gtgaattggg taacgaatcc aactgtcctc acgctgactt gtctggttac     360
acccacgacg gttcttttcca agaatacgct accgctgacg ctgttcaagc cgctcacatt    420
cctcaaggta ctgacttggc tgaagtcgcg ccaatcttgt gtgctggtat caccgtatac     480
aaggctttga gtctgccaa cttgagagca ggccactggg cggccatttc tggtgctgct     540
ggtggtctag gttcttggc tgttcaatat gctaaggcga tgggttacag agtcttaggt     600
attgatggtg gtccaggaaa ggaagaattg tttacctcgc tcggtggtga agtattcatc     660
gacttcacca agagaagga cattgttagc gcagtcgtta aggctaccaa cggcggtgcc      720
cacggtatca tcaatgtttc cgtttccgaa gccgctatcg aagcttctac cagatactgt     780
agggcgaacg gtactgttgt cttggttggt ttgccagccg gtgcaaagtg ctcctctgat     840
gtcttcaacc acgttgtcaa gtctatctcc attgtcggct cttacgtggg gaacagagct     900
gataccagag aagccttaga tttctttgcc agaggtctag tcaagtctcc aataaaggta     960
gttggcttat ccagtttacc agaaatttac gaaaagatgg agaagggcca aattgctggt    1020
agatacgttg ttgacacttc taaataa                                        1047

<210> SEQ ID NO 26
<211> LENGTH: 348
<212> TYPE: PRT
<213> ORGANISM: Saccharomyces cerevisiae

<400> SEQUENCE: 26

Met Ser Ile Pro Glu Thr Gln Lys Ala Ile Ile Phe Tyr Glu Ser Asn
1               5                   10                  15

Gly Lys Leu Glu His Lys Asp Ile Pro Val Pro Lys Pro Lys Pro Asn
            20                  25                  30

Glu Leu Leu Ile Asn Val Lys Tyr Ser Gly Val Cys His Thr Asp Leu
        35                  40                  45

His Ala Trp His Gly Asp Trp Pro Leu Pro Thr Lys Leu Pro Leu Val
    50                  55                  60

Gly Gly His Glu Gly Ala Gly Val Val Val Gly Met Gly Glu Asn Val
65                  70                  75                  80

Lys Gly Trp Lys Ile Gly Asp Tyr Ala Gly Ile Lys Trp Leu Asn Gly
                85                  90                  95

Ser Cys Met Ala Cys Glu Tyr Cys Glu Leu Gly Asn Glu Ser Asn Cys
            100                 105                 110

Pro His Ala Asp Leu Ser Gly Tyr Thr His Asp Gly Ser Phe Gln Glu
        115                 120                 125
```

Tyr Ala Thr Ala Asp Ala Val Gln Ala Ala His Ile Pro Gln Gly Thr
                130                 135                 140

Asp Leu Ala Glu Val Ala Pro Ile Leu Cys Ala Gly Ile Thr Val Tyr
145                 150                 155                 160

Lys Ala Leu Lys Ser Ala Asn Leu Arg Ala Gly His Trp Ala Ala Ile
                165                 170                 175

Ser Gly Ala Ala Gly Gly Leu Gly Ser Leu Ala Val Gln Tyr Ala Lys
                180                 185                 190

Ala Met Gly Tyr Arg Val Leu Gly Ile Asp Gly Gly Pro Gly Lys Glu
                195                 200                 205

Glu Leu Phe Thr Ser Leu Gly Gly Glu Val Phe Ile Asp Phe Thr Lys
210                 215                 220

Glu Lys Asp Ile Val Ser Ala Val Val Lys Ala Thr Asn Gly Gly Ala
225                 230                 235                 240

His Gly Ile Ile Asn Val Ser Val Ser Glu Ala Ala Ile Glu Ala Ser
                245                 250                 255

Thr Arg Tyr Cys Arg Ala Asn Gly Thr Val Val Leu Val Gly Leu Pro
                260                 265                 270

Ala Gly Ala Lys Cys Ser Ser Asp Val Phe Asn His Val Val Lys Ser
                275                 280                 285

Ile Ser Ile Val Gly Ser Tyr Val Gly Asn Arg Ala Asp Thr Arg Glu
290                 295                 300

Ala Leu Asp Phe Phe Ala Arg Gly Leu Val Lys Ser Pro Ile Lys Val
305                 310                 315                 320

Val Gly Leu Ser Ser Leu Pro Glu Ile Tyr Glu Lys Met Glu Lys Gly
                325                 330                 335

Gln Ile Ala Gly Arg Tyr Val Val Asp Thr Ser Lys
                340                 345

<210> SEQ ID NO 27
<211> LENGTH: 1128
<212> TYPE: DNA
<213> ORGANISM: Saccharomyces cerevisiae

<400> SEQUENCE: 27
atgttgagaa cgtcaacatt gttcaccagg cgtgtccaac caagcctatt ttctagaaac      60
attcttagat tgcaatccac agctgcaatc cctaagactc aaaaaggtgt catcttttat     120
gagaataagg ggaagctgca ttacaaagat atccctgtcc ccgagcctaa gccaaatgaa     180
attttaatca acgttaaata ttctggtgta tgtcacaccg atttacatgc ttggcacggc     240
gattggccat tacctgttaa actaccatta gtaggtggtc atgaaggtgc tggtgtagtt     300
gtcaaactag gttccaatgt caagggctgg aaagtcggtg atttagcagg tatcaaatgg     360
ctgaacggtt cttgtatgac atgcgaattc tgtgaatcag gtcatgaatc aaattgtcca     420
gatgctgatt tatctggtta cactcatgat ggttctttcc aacaatttgc gaccgctgat     480
gctattcaag ccgccaaaat tcaacagggt accgacttgg ccgaagtagc cccaatatta     540
tgtgctggtg ttactgtata taagcactaa aagaggcag acttgaaagc tggtgactgg     600
gttgccatct ctggtgctgc aggtggcttg ggttccttgg ccgttcaata tgcaactgcg     660
atgggttaca gagttctagg tattgatgca ggtgaggaaa aggaaaaact tttcaagaaa     720
ttgggggggtg aagtattcat cgactttact aaaacaaaga atatggtttc tgacattcaa     780
gaagctacca aaggtggccc tcatggtgtc attaacgttt ccgttctga  agccgctatt     840
tctctatcta cggaatatgt tagaccatgt ggtaccgtcg ttttggttgg tttgcccgct     900

```
aacgcctacg ttaaatcaga ggtattctct catgtggtga agtccatcaa tatcaagggt    960
tcttatgttg gtaacagagc tgatacgaga gaagccttag acttctttag cagaggtttg   1020
atcaaatcac caatcaaaat tgttggatta tctgaattac caaaggttta tgacttgatg   1080
gaaaagggca agattttggg tagatacgtc gtcgatacta gtaaataa                1128
```

<210> SEQ ID NO 28
<211> LENGTH: 375
<212> TYPE: PRT
<213> ORGANISM: Saccharomyces cerevisiae

<400> SEQUENCE: 28

```
Met Leu Arg Thr Ser Thr Leu Phe Thr Arg Arg Val Gln Pro Ser Leu
1               5                   10                  15

Phe Ser Arg Asn Ile Leu Arg Leu Gln Ser Thr Ala Ala Ile Pro Lys
            20                  25                  30

Thr Gln Lys Gly Val Ile Phe Tyr Glu Asn Lys Gly Lys Leu His Tyr
        35                  40                  45

Lys Asp Ile Pro Val Pro Glu Pro Lys Pro Asn Glu Ile Leu Ile Asn
    50                  55                  60

Val Lys Tyr Ser Gly Val Cys His Thr Asp Leu His Ala Trp His Gly
65                  70                  75                  80

Asp Trp Pro Leu Pro Val Lys Leu Pro Leu Val Gly Gly His Glu Gly
                85                  90                  95

Ala Gly Val Val Val Lys Leu Gly Ser Asn Val Lys Gly Trp Lys Val
            100                 105                 110

Gly Asp Leu Ala Gly Ile Lys Trp Leu Asn Gly Ser Cys Met Thr Cys
        115                 120                 125

Glu Phe Cys Glu Ser Gly His Glu Ser Asn Cys Pro Asp Ala Asp Leu
    130                 135                 140

Ser Gly Tyr Thr His Asp Gly Ser Phe Gln Gln Phe Ala Thr Ala Asp
145                 150                 155                 160

Ala Ile Gln Ala Ala Lys Ile Gln Gln Gly Thr Asp Leu Ala Glu Val
                165                 170                 175

Ala Pro Ile Leu Cys Ala Gly Val Thr Val Tyr Lys Ala Leu Lys Glu
            180                 185                 190

Ala Asp Leu Lys Ala Gly Asp Trp Val Ala Ile Ser Gly Ala Ala Gly
        195                 200                 205

Gly Leu Gly Ser Leu Ala Val Gln Tyr Ala Thr Ala Met Gly Tyr Arg
    210                 215                 220

Val Leu Gly Ile Asp Ala Gly Glu Glu Lys Glu Lys Leu Phe Lys Lys
225                 230                 235                 240

Leu Gly Gly Glu Val Phe Ile Asp Phe Thr Lys Thr Lys Asn Met Val
                245                 250                 255

Ser Asp Ile Gln Glu Ala Thr Lys Gly Gly Pro His Gly Val Ile Asn
            260                 265                 270

Val Ser Val Ser Glu Ala Ala Ile Ser Leu Ser Thr Glu Tyr Val Arg
        275                 280                 285

Pro Cys Gly Thr Val Val Leu Val Gly Leu Pro Ala Asn Ala Tyr Val
    290                 295                 300

Lys Ser Glu Val Phe Ser His Val Val Lys Ser Ile Asn Ile Lys Gly
305                 310                 315                 320

Ser Tyr Val Gly Asn Arg Ala Asp Thr Arg Glu Ala Leu Asp Phe Phe
                325                 330                 335
```

Ser Arg Gly Leu Ile Lys Ser Pro Ile Lys Ile Val Gly Leu Ser Glu
            340                 345                 350

Leu Pro Lys Val Tyr Asp Leu Met Glu Lys Gly Lys Ile Leu Gly Arg
            355                 360                 365

Tyr Val Val Asp Thr Ser Lys
            370                 375

<210> SEQ ID NO 29
<211> LENGTH: 1149
<212> TYPE: DNA
<213> ORGANISM: Saccharomyces cerevisiae

<400> SEQUENCE: 29

| | | | | | |
|---|---|---|---|---|---|
| atgtcttccg | ttactgggtt | ttacattcca | ccaatctctt | tctttggtga | aggtgcttta | 60 |
| gaagaaaccg | ctgattacat | caaaaacaag | gattacaaaa | aggctttgat | cgttactgat | 120 |
| cctggtattg | cagctattgg | tctctccggt | agagtccaaa | agatgttgga | agaacgtgac | 180 |
| ttaaacgttg | ctatctatga | caaaactcaa | ccaaacccaa | atattgccaa | tgtcacagct | 240 |
| ggtttgaagg | ttttgaagga | acaaaactct | gaaattgttg | tttccattgg | tggtggttct | 300 |
| gctcacgaca | atgctaaggc | cattgcttta | ttggctacta | cggtgggga | aatcggagac | 360 |
| tatgaaggtg | tcaatcaatc | taagaaggct | gctttaccac | tatttgccat | caacactact | 420 |
| gctggtactg | cttccgaaat | gaccagattc | actattatct | ctaatgaaga | aaagaaaatc | 480 |
| aagatggcta | tcattgacaa | caacgtcact | ccagctgttg | ctgtcaacga | tccatctacc | 540 |
| atgtttggtt | tgccacctgc | tttgactgct | gctactggtc | tagatgcttt | gactcactgt | 600 |
| atcgaagctt | atgtttccac | cgcctctaac | ccaatcaccg | atgcctgtgc | tttgaagggt | 660 |
| attgatttga | tcaatgaaag | cttagtcgct | gcatacaaag | acggtaaaga | caagaaggcc | 720 |
| agaactgaca | tgtgttacgc | tgaatacttg | gcaggtatgg | ctttcaacaa | tgcttctcta | 780 |
| ggttatgttc | atgcccttgc | tcatcaactt | ggtggtttct | accacttgcc | tcatggtgtt | 840 |
| tgtaacgctg | tcttgttgcc | tcatgttcaa | gaggccaaca | tgcaatgtcc | aaaggccaag | 900 |
| aagagattag | gtgaaattgc | tttgcatttc | ggtgcttctc | aagaagatcc | agaagaaacc | 960 |
| atcaaggctt | tgcacgtttt | aaacagaacc | atgaacattc | aagaaacttt | gaaagaatta | 1020 |
| ggtgttaaaa | ccgaagattt | tgaaattttg | gctgaacacg | ccatgcatga | tgcctgccat | 1080 |
| ttgactaacc | cagttcaatt | caccaaagaa | caagtggttg | ccattatcaa | gaaagcctat | 1140 |
| gaatattaa | | | | | | 1149 |

<210> SEQ ID NO 30
<211> LENGTH: 382
<212> TYPE: PRT
<213> ORGANISM: Saccharomyces cerevisiae

<400> SEQUENCE: 30

Met Ser Ser Val Thr Gly Phe Tyr Ile Pro Ile Ser Phe Phe Gly
1               5                   10                  15

Glu Gly Ala Leu Glu Glu Thr Ala Asp Tyr Ile Lys Asn Lys Asp Tyr
            20                  25                  30

Lys Lys Ala Leu Ile Val Thr Asp Pro Gly Ile Ala Ala Ile Gly Leu
        35                  40                  45

Ser Gly Arg Val Gln Lys Met Leu Glu Glu Arg Asp Leu Asn Val Ala
        50                  55                  60

Ile Tyr Asp Lys Thr Gln Pro Asn Pro Asn Ile Ala Asn Val Thr Ala
65                  70                  75                  80

-continued

Gly Leu Lys Val Leu Lys Glu Gln Asn Ser Glu Ile Val Val Ser Ile
                 85                  90                  95

Gly Gly Gly Ser Ala His Asp Asn Ala Lys Ala Ile Ala Leu Leu Ala
            100                 105                 110

Thr Asn Gly Gly Glu Ile Gly Asp Tyr Glu Gly Val Asn Gln Ser Lys
            115                 120                 125

Lys Ala Ala Leu Pro Leu Phe Ala Ile Asn Thr Thr Ala Gly Thr Ala
130                 135                 140

Ser Glu Met Thr Arg Phe Thr Ile Ile Ser Asn Glu Glu Lys Lys Ile
145                 150                 155                 160

Lys Met Ala Ile Ile Asp Asn Asn Val Thr Pro Ala Val Ala Val Asn
                165                 170                 175

Asp Pro Ser Thr Met Phe Gly Leu Pro Pro Ala Leu Thr Ala Ala Thr
            180                 185                 190

Gly Leu Asp Ala Leu Thr His Cys Ile Glu Ala Tyr Val Ser Thr Ala
            195                 200                 205

Ser Asn Pro Ile Thr Asp Ala Cys Ala Leu Lys Gly Ile Asp Leu Ile
210                 215                 220

Asn Glu Ser Leu Val Ala Ala Tyr Lys Asp Gly Lys Asp Lys Lys Ala
225                 230                 235                 240

Arg Thr Asp Met Cys Tyr Ala Glu Tyr Leu Ala Gly Met Ala Phe Asn
                245                 250                 255

Asn Ala Ser Leu Gly Tyr Val His Ala Leu Ala His Gln Leu Gly Gly
            260                 265                 270

Phe Tyr His Leu Pro His Gly Val Cys Asn Ala Val Leu Leu Pro His
            275                 280                 285

Val Gln Glu Ala Asn Met Gln Cys Pro Lys Ala Lys Lys Arg Leu Gly
290                 295                 300

Glu Ile Ala Leu His Phe Gly Ala Ser Gln Glu Asp Pro Glu Glu Thr
305                 310                 315                 320

Ile Lys Ala Leu His Val Leu Asn Arg Thr Met Asn Ile Pro Arg Asn
                325                 330                 335

Leu Lys Glu Leu Gly Val Lys Thr Glu Asp Phe Glu Ile Leu Ala Glu
            340                 345                 350

His Ala Met His Asp Ala Cys His Leu Thr Asn Pro Val Gln Phe Thr
            355                 360                 365

Lys Glu Gln Val Val Ala Ile Ile Lys Lys Ala Tyr Glu Tyr
370                 375                 380

<210> SEQ ID NO 31
<211> LENGTH: 1056
<212> TYPE: DNA
<213> ORGANISM: Saccharomyces cerevisiae

<400> SEQUENCE: 31
atgccttcgc aagtcattcc tgaaaaacaa aaggctattg tcttttatga cacagatgga      60
aaattggaat ataaagacgt cacagttccg gaacctaagc ctaacgaaat tttagtccac     120
gttaaatatt ctggtgtttg tcatagtgac ttgcacgcgt ggcacggtga ttggccattt     180
caattgaaat ttccattaat cggtggtcac gaaggtgctg gtgttgttgt taagttggga     240
tctaacgtta agggctggaa agtcggtgat tttgcaggta taaatggtt gaatgggact      300 tgcatgtcct gtgaatattg tgaagtaggt aatgaatctc aatgtccttta tttggatggt     360 actggcttca cacatgatgg tacttttcaa gaatacgcaa ctgccgatgc cgttcaagct     420
gcccatattc caccaaacgt caatcttgct gaagttgccc caatcttgtg tgcaggtatc     480

```
actgtttata aggcgttgaa aagagccaat gtgataccag gccaatgggt cactatatcc    540
ggtgcatgcg gtggcttggg ttctctggca atccaatacg cccttgctat gggttacagg    600
gtcattggta tcgatggtgg taatgccaag cgaaagttat ttgaacaatt aggcggagaa    660
atattcatcg atttcacgga agaaaaagac attgttggtg ctataataaa ggccactaat    720
ggcggttctc atggagttat taatgtgtct gtttctgaag cagctatcga ggcttctacg    780
aggtattgta ggcccaatgg tactgtcgtc ctggttggta tgccagctca tgcttactgc    840
aattccgatg ttttcaatca agttgtaaaa tcaatctcca tcgttggatc ttgtgttgga    900
aatagagctg atacaaggga ggctttagat ttcttcgcca gaggtttgat caaatctccg    960
atccacttag ctggcctatc ggatgttcct gaaatttttg caaagatgga aagggtgaa    1020 attgttggta gatatgttgt tgagacttct aaatga                              1056
```

<210> SEQ ID NO 32
<211> LENGTH: 351
<212> TYPE: PRT
<213> ORGANISM: Saccharomyces cerevisiae

<400> SEQUENCE: 32

```
Met Pro Ser Gln Val Ile Pro Glu Lys Gln Lys Ala Ile Val Phe Tyr
1               5                   10                  15

Glu Thr Asp Gly Lys Leu Glu Tyr Lys Asp Val Thr Val Pro Glu Pro
            20                  25                  30

Lys Pro Asn Glu Ile Leu Val His Val Lys Tyr Ser Gly Val Cys His
        35                  40                  45

Ser Asp Leu His Ala Trp His Gly Asp Trp Pro Phe Gln Leu Lys Phe
    50                  55                  60

Pro Leu Ile Gly Gly His Glu Gly Ala Gly Val Val Lys Leu Gly
65                  70                  75                  80

Ser Asn Val Lys Gly Trp Lys Val Gly Asp Phe Ala Gly Ile Lys Trp
                85                  90                  95

Leu Asn Gly Thr Cys Met Ser Cys Glu Tyr Cys Glu Val Gly Asn Glu
            100                 105                 110

Ser Gln Cys Pro Tyr Leu Asp Gly Thr Gly Phe Thr His Asp Gly Thr
        115                 120                 125

Phe Gln Glu Tyr Ala Thr Ala Asp Ala Val Gln Ala Ala His Ile Pro
    130                 135                 140

Pro Asn Val Asn Leu Ala Glu Val Ala Pro Ile Leu Cys Ala Gly Ile
145                 150                 155                 160

Thr Val Tyr Lys Ala Leu Lys Arg Ala Asn Val Ile Pro Gly Gln Trp
                165                 170                 175

Val Thr Ile Ser Gly Ala Cys Gly Gly Leu Gly Ser Leu Ala Ile Gln
            180                 185                 190

Tyr Ala Leu Ala Met Gly Tyr Arg Val Ile Gly Ile Asp Gly Gly Asn
        195                 200                 205

Ala Lys Arg Lys Leu Phe Glu Gln Leu Gly Gly Glu Ile Phe Ile Asp
    210                 215                 220

Phe Thr Glu Glu Lys Asp Ile Val Gly Ala Ile Ile Lys Ala Thr Asn
225                 230                 235                 240

Gly Gly Ser His Gly Val Ile Asn Val Ser Val Ser Glu Ala Ala Ile
                245                 250                 255

Glu Ala Ser Thr Arg Tyr Cys Arg Pro Asn Gly Thr Val Val Leu Val
            260                 265                 270
```

```
Gly Met Pro Ala His Ala Tyr Cys Asn Ser Asp Val Phe Asn Gln Val
        275                 280                 285

Val Lys Ser Ile Ser Ile Val Gly Ser Cys Val Gly Asn Arg Ala Asp
        290                 295                 300

Thr Arg Glu Ala Leu Asp Phe Phe Ala Arg Gly Leu Ile Lys Ser Pro
305                 310                 315                 320

Ile His Leu Ala Gly Leu Ser Asp Val Pro Glu Ile Phe Ala Lys Met
                325                 330                 335

Glu Lys Gly Glu Ile Val Gly Arg Tyr Val Val Glu Thr Ser Lys
                340                 345                 350

<210> SEQ ID NO 33
<211> LENGTH: 1083
<212> TYPE: DNA
<213> ORGANISM: Saccharomyces cerevisiae

<400> SEQUENCE: 33
atgtcttatc ctgagaaatt tgaaggtatc gctattcaat cacacgaaga ttggaaaaac     60
ccaaagaaga caaagtatga cccaaaacca ttttacgatc atgacattga cattaagatc    120
gaagcatgtg gtgtctgcgg tagtgatatt cattgtgcag ctggtcattg ggcaatatg    180
aagatgccgc tagtcgttgg tcatgaaatc gttggtaaag ttgtcaagct agggcccaag    240
tcaaacagtg ggttgaaagt cggtcaacgt gttggtgtag gtgctcaagt cttttcatgc    300
ttggaatgtg accgttgtaa aatgataat gaaccatact gcaccaagtt tgttaccaca    360
tacagtcagc cttatgaaga cggctatgtg tcgcagggtg gctatgcaaa ctacgtcaga    420
gttcatgaac attttgtggt gcctatccca gagaatattc catcacattt ggctgctcca    480
ctattatgtg tggtttgac tgtgtactct ccattggttc gtaacggttg cggtccaggt    540
aaaaaagttg gtatagttgg tcttggtggt atcggcagta tgggtacatt gatttccaaa    600
gccatggggg cagagacgta tgttatttct cgttcttcga gaaaaagaga gatgcaatg    660
aagatgggcg ccgatcacta cattgctaca ttagaagaag gtgattgggg tgaaaagtac    720
tttgacacct cgacctgat tgtagtctgt gcttcctccc ttaccgacat tgacttcaac    780
attatgccaa aggctatgaa ggttggtggt agaattgtct caatctctat accagaacaa    840
cacgaaatgt tatcgctaaa gccatatggc ttaaaggctg tctccatttc ttacagtgct    900
ttaggttcca tcaaagaatt gaaccaactc ttgaaattag tctctgaaaa agatatcaaa    960
atttgggtgg aaacattacc tgttggtgaa gccggcgtcc atgaagcctt cgaaaggatg   1020
gaaaagggtg acgttagata tagatttacc ttagtcggct acgacaaaga attttcagac   1080
tag                                                                  1083

<210> SEQ ID NO 34
<211> LENGTH: 360
<212> TYPE: PRT
<213> ORGANISM: Saccharomyces cerevisiae

<400> SEQUENCE: 34

Met Ser Tyr Pro Glu Lys Phe Glu Gly Ile Ala Ile Gln Ser His Glu
1               5                   10                  15

Asp Trp Lys Asn Pro Lys Lys Thr Lys Tyr Asp Pro Lys Pro Phe Tyr
            20                  25                  30

Asp His Asp Ile Asp Ile Lys Ile Glu Ala Cys Gly Val Cys Gly Ser
        35                  40                  45

Asp Ile His Cys Ala Ala Gly His Trp Gly Asn Met Lys Met Pro Leu
    50                  55                  60
```

Val Val Gly His Glu Ile Val Gly Lys Val Lys Leu Gly Pro Lys
65                  70                  75                  80

Ser Asn Ser Gly Leu Lys Val Gly Gln Arg Val Gly Val Gly Ala Gln
            85                  90                  95

Val Phe Ser Cys Leu Glu Cys Asp Arg Cys Lys Asn Asp Asn Glu Pro
            100                 105                 110

Tyr Cys Thr Lys Phe Val Thr Thr Tyr Ser Gln Pro Tyr Glu Asp Gly
            115                 120                 125

Tyr Val Ser Gln Gly Gly Tyr Ala Asn Tyr Val Arg Val His Glu His
            130                 135                 140

Phe Val Val Pro Ile Pro Glu Asn Ile Pro Ser His Leu Ala Ala Pro
145                 150                 155                 160

Leu Leu Cys Gly Gly Leu Thr Val Tyr Ser Pro Leu Val Arg Asn Gly
            165                 170                 175

Cys Gly Pro Gly Lys Lys Val Gly Ile Val Gly Leu Gly Gly Ile Gly
            180                 185                 190

Ser Met Gly Thr Leu Ile Ser Lys Ala Met Gly Ala Glu Thr Tyr Val
            195                 200                 205

Ile Ser Arg Ser Ser Arg Lys Arg Glu Asp Ala Met Lys Met Gly Ala
210                 215                 220

Asp His Tyr Ile Ala Thr Leu Glu Glu Gly Asp Trp Gly Glu Lys Tyr
225                 230                 235                 240

Phe Asp Thr Phe Asp Leu Ile Val Val Cys Ala Ser Ser Leu Thr Asp
            245                 250                 255

Ile Asp Phe Asn Ile Met Pro Lys Ala Met Lys Val Gly Gly Arg Ile
            260                 265                 270

Val Ser Ile Ser Ile Pro Glu Gln His Glu Met Leu Ser Leu Lys Pro
            275                 280                 285

Tyr Gly Leu Lys Ala Val Ser Ile Ser Tyr Ser Ala Leu Gly Ser Ile
            290                 295                 300

Lys Glu Leu Asn Gln Leu Leu Lys Leu Val Ser Glu Lys Asp Ile Lys
305                 310                 315                 320

Ile Trp Val Glu Thr Leu Pro Val Gly Glu Ala Gly Val His Glu Ala
            325                 330                 335

Phe Glu Arg Met Glu Lys Gly Asp Val Arg Tyr Arg Phe Thr Leu Val
            340                 345                 350

Gly Tyr Asp Lys Glu Phe Ser Asp
            355                 360

<210> SEQ ID NO 35
<211> LENGTH: 1086
<212> TYPE: DNA
<213> ORGANISM: Saccharomyces cerevisiae

<400> SEQUENCE: 35
atgctttacc cagaaaaatt tcagggcatc ggtatttcca acgcaaagga ttggaagcat      60
cctaaattag tgagttttga cccaaaaccc tttggcgatc atgacgttga tgttgaaatt     120
gaagcctgtg gtatctgcgg atctgatttt catatagccg ttggtaattg gggtccagtc     180
ccagaaaatc aaatccttgg acatgaaata attggccgcg tggtgaaggt tggatccaag     240
tgccacactg gggtaaaaat cggtgaccgt gttggtgttg gtcccaagc cttggcgtgt     300 tttgagtgtg aacgttgcaa aagtgacaac gagcaatact gtaccaatga ccacgttttg     360
actatgtgga ctccttacaa ggacggctac atttcacaag gaggctttgc ctcccacgtg     420

```
aggcttcatg aacactttgc tattcaaata ccagaaaata ttccaagtcc gctagccgct    480
ccattattgt gtggtggtat tacagttttc tctccactac taagaaatgg ctgtggtcca    540
ggtaagaggg taggtattgt tggcatcggt ggtattgggc atatggggat tctgttggct    600
aaagctatgg gagccgaggt ttatgcgttt tcgcgaggcc actccaagcg ggaggattct    660
atgaaactcg gtgctgatca ctatattgct atgttggagg ataaaggctg gacagaacaa    720
tactctaacg ctttggacct tcttgtcgtt tgctcatcat ctttgtcgaa agttaatttt    780
gacagtatcg ttaagattat gaagattgga ggctccatcg tttcaattgc tgctcctgaa    840
gttaatgaaa agcttgtttt aaaaccgttg ggcctaatgg gagtatcaat ctcaagcagt    900
gctatcggat ctaggaagga aatcgaacaa ctattgaaat tagtttccga aaagaatgtc    960
aaaatatggg tggaaaaact tccgatcagc gaagaaggcg tcagccatgc ctttacaagg   1020
atggaaagcg gagacgtcaa atacagattt actttggtcg attatgataa gaaattccat   1080
aaatag                                                              1086

<210> SEQ ID NO 36
<211> LENGTH: 361
<212> TYPE: PRT
<213> ORGANISM: Saccharomyces cerevisiae

<400> SEQUENCE: 36

Met Leu Tyr Pro Glu Lys Phe Gln Gly Ile Gly Ile Ser Asn Ala Lys
1               5                   10                  15

Asp Trp Lys His Pro Lys Leu Val Ser Phe Asp Pro Lys Pro Phe Gly
            20                  25                  30

Asp His Asp Val Asp Val Glu Ile Glu Ala Cys Gly Ile Cys Gly Ser
        35                  40                  45

Asp Phe His Ile Ala Val Gly Asn Trp Gly Pro Val Pro Glu Asn Gln
    50                  55                  60

Ile Leu Gly His Glu Ile Ile Gly Arg Val Val Lys Val Gly Ser Lys
65                  70                  75                  80

Cys His Thr Gly Val Lys Ile Gly Asp Arg Val Gly Val Gly Ala Gln
                85                  90                  95

Ala Leu Ala Cys Phe Glu Cys Glu Arg Cys Lys Ser Asp Asn Glu Gln
            100                 105                 110

Tyr Cys Thr Asn Asp His Val Leu Thr Met Trp Thr Pro Tyr Lys Asp
        115                 120                 125

Gly Tyr Ile Ser Gln Gly Gly Phe Ala Ser His Val Arg Leu His Glu
    130                 135                 140

His Phe Ala Ile Gln Ile Pro Glu Asn Ile Pro Ser Pro Leu Ala Ala
145                 150                 155                 160

Pro Leu Leu Cys Gly Gly Ile Thr Val Phe Ser Pro Leu Leu Arg Asn
                165                 170                 175

Gly Cys Gly Pro Gly Lys Arg Val Gly Ile Val Gly Ile Gly Gly Ile
            180                 185                 190

Gly His Met Gly Ile Leu Leu Ala Lys Ala Met Gly Ala Glu Val Tyr
        195                 200                 205

Ala Phe Ser Arg Gly His Ser Lys Arg Glu Asp Ser Met Lys Leu Gly
    210                 215                 220

Ala Asp His Tyr Ile Ala Met Leu Glu Asp Lys Gly Trp Thr Glu Gln
225                 230                 235                 240

Tyr Ser Asn Ala Leu Asp Leu Val Val Cys Ser Ser Ser Leu Ser
                245                 250                 255
```

```
Lys Val Asn Phe Asp Ser Ile Val Lys Ile Met Lys Ile Gly Gly Ser
            260                 265                 270

Ile Val Ser Ile Ala Ala Pro Glu Val Asn Glu Lys Leu Val Leu Lys
        275                 280                 285

Pro Leu Gly Leu Met Gly Val Ser Ile Ser Ser Ala Ile Gly Ser
    290                 295                 300

Arg Lys Glu Ile Glu Gln Leu Leu Lys Leu Val Ser Glu Lys Asn Val
305                 310                 315                 320

Lys Ile Trp Val Glu Lys Leu Pro Ile Ser Glu Gly Val Ser His
                325                 330                 335

Ala Phe Thr Arg Met Glu Ser Gly Asp Val Lys Tyr Arg Phe Thr Leu
                340                 345                 350

Val Asp Tyr Asp Lys Lys Phe His Lys
            355                 360

<210> SEQ ID NO 37
<211> LENGTH: 1161
<212> TYPE: DNA
<213> ORGANISM: Saccharomyces cerevisiae

<400> SEQUENCE: 37
atgtccgccg ctactgttgg taaacctatt aagtgcattg ctgctgttgc gtatgatgcg      60
aagaaaccat taagtgttga agaaatcacg gtagacgccc aaaagcgca cgaagtacgt     120
atcaaaattg aatatactgc tgtatgccac actgatgcgt acactttatc aggctctgat     180
ccagaaggac ttttcccttg cgttctgggc acgaaggag ccggtatcgt agaatctgta     240
ggcgatgatg tcataacagt taagcctggt gatcatgtta ttgctttgta cactgctgag     300
tgtggcaaat gtaagttctg tacttccggt aaaaccaact tatgtggtgc tgttagagct     360
actcaaggga aggtgtaat gcctgatggg accacaagat tcataatgc gaaaggtgaa     420
gatatatacc atttcatggg ttgctctact ttttccgaat atactgtggt ggcagatgtc     480
tctgtggttg ccatcgatcc aaaagctccc ttggatgctg cctgtttact gggttgtggt     540
gttactactg ttttggggc ggctcttaag acagctaatg tgcaaaaagg cgataccgtt     600
gcagtatttg gctgcgggac tgtaggactc tccgttatcc aaggtgcaaa gttaaggggc     660
gcttccaaga tcattgccat tgacattaac aataagaaaa aacaatattg ttctcaattt     720
ggtgccacgg attttgttaa tcccaaggaa gatttggcca agatcaaac tatcgttgaa     780
aagttaattg aaatgactga tgggggtctg gattttactt ttgactgtac tggtaatacc     840
aaaattatga gagatgcttt ggaagcctgt cataaaggtt ggggtcaatc tattatcatt     900
ggtgtggctg ccgctggtga agaaattct acaaggccgt tccagctggt cactggtaga     960
gtgtggaaag gctctgcttt tggtggcatc aaaggtagat ctgaaatggg cggtttaatt    1020
aaagactatc aaaaggtgc cttaaaagtc gaagaattta tcactcacag gagaccattc    1080
aaagaaatca atcaagcctt tgaagatttg cataacggtg attgcttaag aaccgtcttg    1140
aagtctgatg aaataaaata g                                             1161

<210> SEQ ID NO 38
<211> LENGTH: 386
<212> TYPE: PRT
<213> ORGANISM: Saccharomyces cerevisiae

<400> SEQUENCE: 38

Met Ser Ala Ala Thr Val Gly Lys Pro Ile Lys Cys Ile Ala Ala Val
1               5                   10                  15
```

-continued

Ala Tyr Asp Ala Lys Lys Pro Leu Ser Val Glu Glu Ile Thr Val Asp
        20                  25                  30

Ala Pro Lys Ala His Glu Val Arg Ile Lys Ile Glu Tyr Thr Ala Val
        35                  40                  45

Cys His Thr Asp Ala Tyr Thr Leu Ser Gly Ser Asp Pro Glu Gly Leu
 50                  55                  60

Phe Pro Cys Val Leu Gly His Glu Gly Ala Gly Ile Val Glu Ser Val
 65                  70                  75                  80

Gly Asp Asp Val Ile Thr Val Lys Pro Gly Asp His Val Ile Ala Leu
                85                  90                  95

Tyr Thr Ala Glu Cys Gly Lys Cys Lys Phe Cys Thr Ser Gly Lys Thr
                100                 105                 110

Asn Leu Cys Gly Ala Val Arg Ala Thr Gln Gly Lys Gly Val Met Pro
            115                 120                 125

Asp Gly Thr Thr Arg Phe His Asn Ala Lys Gly Glu Asp Ile Tyr His
            130                 135                 140

Phe Met Gly Cys Ser Thr Phe Ser Glu Tyr Thr Val Val Ala Asp Val
145                 150                 155                 160

Ser Val Val Ala Ile Asp Pro Lys Ala Pro Leu Asp Ala Ala Cys Leu
                165                 170                 175

Leu Gly Cys Gly Val Thr Thr Gly Phe Gly Ala Ala Leu Lys Thr Ala
                180                 185                 190

Asn Val Gln Lys Gly Asp Thr Val Ala Val Phe Gly Cys Gly Thr Val
            195                 200                 205

Gly Leu Ser Val Ile Gln Gly Ala Lys Leu Arg Gly Ala Ser Lys Ile
            210                 215                 220

Ile Ala Ile Asp Ile Asn Asn Lys Lys Lys Gln Tyr Cys Ser Gln Phe
225                 230                 235                 240

Gly Ala Thr Asp Phe Val Asn Pro Lys Glu Asp Leu Ala Lys Asp Gln
                245                 250                 255

Thr Ile Val Glu Lys Leu Ile Glu Met Thr Asp Gly Gly Leu Asp Phe
                260                 265                 270

Thr Phe Asp Cys Thr Gly Asn Thr Lys Ile Met Arg Asp Ala Leu Glu
            275                 280                 285

Ala Cys His Lys Gly Trp Gly Gln Ser Ile Ile Ile Gly Val Ala Ala
            290                 295                 300

Ala Gly Glu Glu Ile Ser Thr Arg Pro Phe Gln Leu Val Thr Gly Arg
305                 310                 315                 320

Val Trp Lys Gly Ser Ala Phe Gly Gly Ile Lys Gly Arg Ser Glu Met
                325                 330                 335

Gly Gly Leu Ile Lys Asp Tyr Gln Lys Gly Ala Leu Lys Val Glu Glu
            340                 345                 350

Phe Ile Thr His Arg Arg Pro Phe Lys Glu Ile Asn Gln Ala Phe Glu
            355                 360                 365

Asp Leu His Asn Gly Asp Cys Leu Arg Thr Val Leu Lys Ser Asp Glu
            370                 375                 380

Ile Lys
385

<210> SEQ ID NO 39
<211> LENGTH: 939
<212> TYPE: DNA
<213> ORGANISM: Saccharomyces cerevisiae

<400> SEQUENCE: 39

```
atgcctgcta cgttaaagaa ttcttctgct acattaaaac taaatactgg tgcctccatt      60
ccagtgttgg gtttcggcac ttggcgttcc gttgacaata acggttacca ttctgtaatt     120
gcagctttga aagctggata cagacacatt gatgctgcgg ctatctattt gaatgaagaa     180
gaagttggca gggctattaa agattccgga gtccctcgtg aggaaatttt tattactact     240
aagctttggg gtacggaaca acgtgatccg gaagctgctc taaacaagtc tttgaaaaga     300
ctaggcttgg attatgttga cctatatctg atgcattggc cagtgccttt gaaaaccgac     360
agagttactg atggtaacgt tctgtgcatt ccaacattag aagatggcac tgttgacatc     420
gatactaagg aatggaattt tatcaagacg tgggagttga tgcaagagtt gccaaagacg     480
ggcaaaacta aagccgttgg tgtctctaat ttttctatta acaacattaa agaattatta     540
gaatctccaa ataacaaggt ggtaccagct actaatcaaa ttgaaattca tccattgcta     600
ccacaagacg aattgattgc ctttgtaag gaaaagggta ttgttgttga agcctactca      660
ccatttggga gtgctaatgc tcctttacta aaagagcaag caattattga tatggctaaa     720
aagcacggcg ttgagccagc acagcttatt atcagttgga gtattcaaag aggctacgtt     780
gttctggcca aatcggttaa tcctgaaaga attgtatcca attttaagat tttcactctg     840
cctgaggatg atttcaagac tattagtaac ctatccaaag tgcatggtac aaagagagtc     900
gttgatatga agtggggatc cttcccaatt ttccaatga                            939
```

<210> SEQ ID NO 40
<211> LENGTH: 312
<212> TYPE: PRT
<213> ORGANISM: Saccharomyces cerevisiae

<400> SEQUENCE: 40

```
Met Pro Ala Thr Leu Lys Asn Ser Ser Ala Thr Leu Lys Leu Asn Thr
1               5                   10                  15

Gly Ala Ser Ile Pro Val Leu Gly Phe Gly Thr Trp Arg Ser Val Asp
            20                  25                  30

Asn Asn Gly Tyr His Ser Val Ile Ala Ala Leu Lys Ala Gly Tyr Arg
        35                  40                  45

His Ile Asp Ala Ala Ala Ile Tyr Leu Asn Glu Glu Glu Val Gly Arg
    50                  55                  60

Ala Ile Lys Asp Ser Gly Val Pro Arg Glu Glu Ile Phe Ile Thr Thr
65                  70                  75                  80

Lys Leu Trp Gly Thr Glu Gln Arg Asp Pro Glu Ala Ala Leu Asn Lys
                85                  90                  95

Ser Leu Lys Arg Leu Gly Leu Asp Tyr Val Asp Leu Tyr Leu Met His
            100                 105                 110

Trp Pro Val Pro Leu Lys Thr Asp Arg Val Thr Asp Gly Asn Val Leu
        115                 120                 125

Cys Ile Pro Thr Leu Glu Asp Gly Thr Val Asp Ile Asp Thr Lys Glu
    130                 135                 140

Trp Asn Phe Ile Lys Thr Trp Glu Leu Met Gln Glu Leu Pro Lys Thr
145                 150                 155                 160

Gly Lys Thr Lys Ala Val Gly Val Ser Asn Phe Ser Ile Asn Asn Ile
                165                 170                 175

Lys Glu Leu Leu Glu Ser Pro Asn Asn Lys Val Val Pro Ala Thr Asn
            180                 185                 190

Gln Ile Glu Ile His Pro Leu Leu Pro Gln Asp Glu Leu Ile Ala Phe
        195                 200                 205

Cys Lys Glu Lys Gly Ile Val Val Glu Ala Tyr Ser Pro Phe Gly Ser
```

```
            210                 215                 220
Ala Asn Ala Pro Leu Leu Lys Glu Gln Ala Ile Ile Asp Met Ala Lys
225                 230                 235                 240

Lys His Gly Val Glu Pro Ala Gln Leu Ile Ile Ser Trp Ser Ile Gln
                245                 250                 255

Arg Gly Tyr Val Val Leu Ala Lys Ser Val Asn Pro Glu Arg Ile Val
                260                 265                 270

Ser Asn Phe Lys Ile Phe Thr Leu Pro Glu Asp Phe Lys Thr Ile
            275                 280                 285

Ser Asn Leu Ser Lys Val His Gly Thr Lys Arg Val Val Asp Met Lys
            290                 295                 300

Trp Gly Ser Phe Pro Ile Phe Gln
305                 310

<210> SEQ ID NO 41
<211> LENGTH: 999
<212> TYPE: DNA
<213> ORGANISM: Saccharomyces cerevisiae

<400> SEQUENCE: 41
atgatcagaa ttgctattaa cggtttcggt agaatcggta gattggtctt gagattggct       60
ttgcaaagaa aagacattga ggttgttgct gtcaacgatc catttatctc taacgattat      120
gctgcttaca tggtcaagta cgattctact catggtagat acaagggtac tgtttcccat      180
gacgacaagc acatcatcat tgatggtgtc aagatcgcta cctaccaaga aagagaccca      240
gctaacttgc catggggttc tctaaagatc gatgtcgctg ttgactccac tggtgttttc      300
aaggaattgg acaccgctca aaagcacatt gacgctggtg ccaagaaggt tgtcatcact      360
gctccatctt cttctgctcc aatgtttgtt gttggtgtta ccacactaa atacactcca      420 gacaagaaga ttgtctccaa cgcttcttgt accaccaact gtttggctcc attggccaag      480
gttatcaacg atgctttcgg tattgaagaa ggtttgatga ccactgttca ctccatgacc      540
gccactcaaa agactgttga tggtccatcc cacaaggact ggagaggtgg tagaaccgct      600
tccggtaaca ttatcccatc ctctaccggt gctgctaagg ctgtcggtaa ggtcttgcca      660
gaattgcaag gtaagttgac cggtatggct ttcagagtcc caaccgtcga tgtttccgtt      720
gttgacttga ctgtcaagtt ggaaaaggaa gctacttacg accaaatcaa gaaggctgtt      780
aaggctgccg ctgaaggtcc aatgaagggt gttttgggtt acaccgaaga tgccgttgtc      840
tcctctgatt tcttgggtga cactcacgct tccatcttcg atgcctccgc tggtatccaa      900
ttgtctccaa agttcgtcaa gttgatttcc tggtacgata cgaatacgg ttactccgcc       960 agagttgttg acttgatcga atatgttgcc aaggcttaa                              999

<210> SEQ ID NO 42
<211> LENGTH: 332
<212> TYPE: PRT
<213> ORGANISM: Saccharomyces cerevisiae

<400> SEQUENCE: 42

Met Ile Arg Ile Ala Ile Asn Gly Phe Gly Arg Ile Gly Arg Leu Val
1               5                   10                  15

Leu Arg Leu Ala Leu Gln Arg Lys Asp Ile Glu Val Val Ala Val Asn
                20                  25                  30

Asp Pro Phe Ile Ser Asn Asp Tyr Ala Ala Tyr Met Val Lys Tyr Asp
            35                  40                  45

Ser Thr His Gly Arg Tyr Lys Gly Thr Val Ser His Asp Asp Lys His
```

```
                  50                  55                  60
Ile Ile Ile Asp Gly Val Lys Ile Ala Thr Tyr Gln Glu Arg Asp Pro
 65                  70                  75                  80

Ala Asn Leu Pro Trp Gly Ser Leu Lys Ile Asp Val Ala Val Asp Ser
                 85                  90                  95

Thr Gly Val Phe Lys Glu Leu Asp Thr Ala Gln Lys His Ile Asp Ala
                100                 105                 110

Gly Ala Lys Lys Val Val Ile Thr Ala Pro Ser Ser Ala Pro Met
                115                 120                 125

Phe Val Val Gly Val Asn His Thr Lys Tyr Thr Pro Asp Lys Lys Ile
130                 135                 140

Val Ser Asn Ala Ser Cys Thr Thr Asn Cys Leu Ala Pro Leu Ala Lys
145                 150                 155                 160

Val Ile Asn Asp Ala Phe Gly Ile Glu Glu Gly Leu Met Thr Thr Val
                165                 170                 175

His Ser Met Thr Ala Thr Gln Lys Thr Val Asp Gly Pro Ser His Lys
                180                 185                 190

Asp Trp Arg Gly Gly Arg Thr Ala Ser Gly Asn Ile Ile Pro Ser Ser
            195                 200                 205

Thr Gly Ala Ala Lys Ala Val Gly Lys Val Leu Pro Glu Leu Gln Gly
210                 215                 220

Lys Leu Thr Gly Met Ala Phe Arg Val Pro Thr Val Asp Val Ser Val
225                 230                 235                 240

Val Asp Leu Thr Val Lys Leu Glu Lys Glu Ala Thr Tyr Asp Gln Ile
                245                 250                 255

Lys Lys Ala Val Lys Ala Ala Ala Glu Gly Pro Met Lys Gly Val Leu
                260                 265                 270

Gly Tyr Thr Glu Asp Ala Val Val Ser Ser Asp Phe Leu Gly Asp Thr
            275                 280                 285

His Ala Ser Ile Phe Asp Ala Ser Ala Gly Ile Gln Leu Ser Pro Lys
            290                 295                 300

Phe Val Lys Leu Ile Ser Trp Tyr Asp Asn Glu Tyr Gly Tyr Ser Ala
305                 310                 315                 320

Arg Val Val Asp Leu Ile Glu Tyr Val Ala Lys Ala
                325                 330
```

<210> SEQ ID NO 43
<211> LENGTH: 999
<212> TYPE: DNA
<213> ORGANISM: Saccharomyces cerevisiae

<400> SEQUENCE: 43

```
atggttagag ttgctattaa cggtttcggt agaatcggta gattggttat gagaattgct      60
ttgcaaagaa agaacgtcga agttgttgct ttgaacgatc ctttcatctc taacgactac     120
tccgcttaca tgttcaagta cgactctact cacggtagat acgctggtga agtttcccac     180
gatgacaagc acatcatcgt tgatggtcac aagatcgcca ctttccaaga aagagaccca     240
gctaacttgc catgggcttc tctaaacatt gacatcgcca ttgactccac tggtgttttc     300
aaggaattgg acactgctca aaagcacatt gacgctggtg ccaagaaggt tgtcatcact     360
gctccatctt ccaccgcccc aatgttcgtc atgggtgtta acgaagaaaa atacactttct    420 gacttgaaga ttgttccaa cgcttcttgt accaccaact gtttggctcc attggccaag     480
gttatcaacg atgctttcgg tattgaagaa ggtttgatga ccactgttca ctccatgacc     540
gccacccaaa agactgttga cggtccatcc cacaaggact ggagaggtgg tagaaccgct     600
```

```
tccggtaaca tcatcccatc ctctaccggt gctgctaagg ctgtcggtaa ggtcttgcca    660
gaattgcaag gtaagttgac cggtatggct ttcagagtcc caaccgtcga tgtttccgtt    720
gttgacttga ctgtcaagtt gaacaaggaa accacctacg atgaaatcaa gaaggttgtc    780
aaggctgccg ctgaaggtaa gttgaagggt gtcttgggtt acactgaaga cgctgttgtc    840
tcctctgact tcttgggtga ctctaactct tccatcttcg atgctgccgc tggtatccaa    900
ttgtctccaa agttcgtcaa gttggtttcc tggtacgaca acgaatacgg ttactctacc    960
agagttgtcg acttggttga acacgttgcc aaggcttaa                            999
```

```
<210> SEQ ID NO 44
<211> LENGTH: 332
<212> TYPE: PRT
<213> ORGANISM: Saccharomyces cerevisiae

<400> SEQUENCE: 44

Met Val Arg Val Ala Ile Asn Gly Phe Gly Arg Ile Gly Arg Leu Val
1               5                   10                  15

Met Arg Ile Ala Leu Gln Arg Lys Asn Val Glu Val Val Ala Leu Asn
            20                  25                  30

Asp Pro Phe Ile Ser Asn Asp Tyr Ser Ala Tyr Met Phe Lys Tyr Asp
        35                  40                  45

Ser Thr His Gly Arg Tyr Ala Gly Glu Val Ser His Asp Asp Lys His
    50                  55                  60

Ile Ile Val Asp Gly His Lys Ile Ala Thr Phe Gln Glu Arg Asp Pro
65                  70                  75                  80

Ala Asn Leu Pro Trp Ala Ser Leu Asn Ile Asp Ile Ala Ile Asp Ser
                85                  90                  95

Thr Gly Val Phe Lys Glu Leu Asp Thr Ala Gln Lys His Ile Asp Ala
            100                 105                 110

Gly Ala Lys Lys Val Val Ile Thr Ala Pro Ser Ser Thr Ala Pro Met
        115                 120                 125

Phe Val Met Gly Val Asn Glu Glu Lys Tyr Thr Ser Asp Leu Lys Ile
    130                 135                 140

Val Ser Asn Ala Ser Cys Thr Thr Asn Cys Leu Ala Pro Leu Ala Lys
145                 150                 155                 160

Val Ile Asn Asp Ala Phe Gly Ile Glu Glu Gly Leu Met Thr Thr Val
                165                 170                 175

His Ser Met Thr Ala Thr Gln Lys Thr Val Asp Gly Pro Ser His Lys
            180                 185                 190

Asp Trp Arg Gly Gly Arg Thr Ala Ser Gly Asn Ile Ile Pro Ser Ser
        195                 200                 205

Thr Gly Ala Ala Lys Ala Val Gly Lys Val Leu Pro Glu Leu Gln Gly
    210                 215                 220

Lys Leu Thr Gly Met Ala Phe Arg Val Pro Thr Val Asp Val Ser Val
225                 230                 235                 240

Val Asp Leu Thr Val Lys Leu Asn Lys Glu Thr Thr Tyr Asp Glu Ile
                245                 250                 255

Lys Lys Val Val Lys Ala Ala Ala Glu Gly Lys Leu Lys Gly Val Leu
            260                 265                 270

Gly Tyr Thr Glu Asp Ala Val Val Ser Ser Asp Phe Leu Gly Asp Ser
        275                 280                 285

Asn Ser Ser Ile Phe Asp Ala Ala Ala Gly Ile Gln Leu Ser Pro Lys
    290                 295                 300
```

Phe Val Lys Leu Val Ser Trp Tyr Asp Asn Glu Tyr Gly Tyr Ser Thr
305                 310                 315                 320

Arg Val Val Asp Leu Val Glu His Val Ala Lys Ala
                325                 330

<210> SEQ ID NO 45
<211> LENGTH: 999
<212> TYPE: DNA
<213> ORGANISM: Saccharomyces cerevisiae

<400> SEQUENCE: 45

```
atggttagag ttgctattaa cggtttcggt agaatcggta gattggtcat gagaattgct      60
ttgtctagac caaacgtcga agttgttgct ttgaacgacc cattcatcac caacgactac    120
gctgcttaca tgttcaagta cgactccact cacggtagat acgctggtga agtttcccac    180
gatgacaagc acatcattgt cgatggtaag aagattgcta cttaccaaga aagagaccca    240
gctaacttgc catggggttc ttccaacgtt gacatcgcca ttgactccac tggtgttttc    300
aaggaattag acactgctca aaagcacatt gacgctggtg ccaagaaggt tgttatcact    360
gctccatctt ccaccgcccc aatgttcgtc atgggtgtta cgaagaaaa atacacttct    420
gacttgaaga ttgtttccaa cgcttcttgt accaccaact gtttggctcc attggccaag    480
gttatcaacg atgctttcgg tattgaagaa ggtttgatga ccactgtcca ctctttgact    540
gctactcaaa agactgttga cggtccatcc acaaggact ggagaggtgg tagaaccgct    600
tccggtaaca tcatcccatc ctccaccggt gctgctaagg ctgtcggtaa ggtcttgcca    660
gaattgcaag gtaagttgac cggtatggct ttcagagtcc caaccgtcga tgtctccgtt    720
gttgacttga ctgtcaagtt gaacaaggaa accacctacg atgaaatcaa gaaggttgtt    780
aaggctgccg ctgaaggtaa gttgaagggt gttttgggtt acaccgaaga cgctgttgtc    840
tcctctgact tcttgggtga ctctcactct tccatcttcg atgcttccgc tggtatccaa    900
ttgtctccaa agttcgtcaa gttggtctcc tggtacgaca cgaatacgg ttactctacc    960
agagttgtcg acttggttga acacgttgcc aaggcttaa                            999
```

<210> SEQ ID NO 46
<211> LENGTH: 332
<212> TYPE: PRT
<213> ORGANISM: Saccharomyces cerevisiae

<400> SEQUENCE: 46

Met Val Arg Val Ala Ile Asn Gly Phe Gly Arg Ile Gly Arg Leu Val
1               5                   10                  15

Met Arg Ile Ala Leu Ser Arg Pro Asn Val Glu Val Val Ala Leu Asn
                20                  25                  30

Asp Pro Phe Ile Thr Asn Asp Tyr Ala Ala Tyr Met Phe Lys Tyr Asp
            35                  40                  45

Ser Thr His Gly Arg Tyr Ala Gly Glu Val Ser His Asp Asp Lys His
        50                  55                  60

Ile Ile Val Asp Gly Lys Lys Ile Ala Thr Tyr Gln Glu Arg Asp Pro
65                  70                  75                  80

Ala Asn Leu Pro Trp Gly Ser Ser Asn Val Asp Ile Ala Ile Asp Ser
                85                  90                  95

Thr Gly Val Phe Lys Glu Leu Asp Thr Ala Gln Lys His Ile Asp Ala
            100                 105                 110

Gly Ala Lys Lys Val Val Ile Thr Ala Pro Ser Ser Thr Ala Pro Met
        115                 120                 125

-continued

```
Phe Val Met Gly Val Asn Glu Glu Lys Tyr Thr Ser Asp Leu Lys Ile
            130                 135                 140

Val Ser Asn Ala Ser Cys Thr Thr Asn Cys Leu Ala Pro Leu Ala Lys
145                 150                 155                 160

Val Ile Asn Asp Ala Phe Gly Ile Glu Glu Gly Leu Met Thr Thr Val
                165                 170                 175

His Ser Leu Thr Ala Thr Gln Lys Thr Val Asp Gly Pro Ser His Lys
            180                 185                 190

Asp Trp Arg Gly Gly Arg Thr Ala Ser Gly Asn Ile Ile Pro Ser Ser
        195                 200                 205

Thr Gly Ala Ala Lys Ala Val Gly Lys Val Leu Pro Glu Leu Gln Gly
    210                 215                 220

Lys Leu Thr Gly Met Ala Phe Arg Val Pro Thr Val Asp Val Ser Val
225                 230                 235                 240

Val Asp Leu Thr Val Lys Leu Asn Lys Glu Thr Thr Tyr Asp Glu Ile
                245                 250                 255

Lys Lys Val Val Lys Ala Ala Ala Glu Gly Lys Leu Lys Gly Val Leu
            260                 265                 270

Gly Tyr Thr Glu Asp Ala Val Val Ser Ser Asp Phe Leu Gly Asp Ser
        275                 280                 285

His Ser Ser Ile Phe Asp Ala Ser Ala Gly Ile Gln Leu Ser Pro Lys
    290                 295                 300

Phe Val Lys Leu Val Ser Trp Tyr Asp Asn Glu Tyr Gly Tyr Ser Thr
305                 310                 315                 320

Arg Val Val Asp Leu Val Glu His Val Ala Lys Ala
                325                 330

<210> SEQ ID NO 47
<211> LENGTH: 1071
<212> TYPE: DNA
<213> ORGANISM: Kluyveromyces lactis

<400> SEQUENCE: 47
atgcccgata tgacaaacga atcttcttct aagccagctc aaattaacat tggtatcaat      60
ggttttggta gaatcggtag attggttcta cgtgctgctt tgacgcaccc agaagttaag     120
gtcagattaa tcaataatcc atccacaaca ccagaatacg ctgcttattt gttcaaatac     180
gattctactc acggcaagta tcgtggtgaa gttgaattcg acgatgaacg tatcatcatt     240
caaaatgacc atgtttcggc tcatatccct ctatctcatt ttagggaacc agagcgtatc     300
ccatgggctt cctacaacgt cgattatgta attgactcaa ccggtgtctt caaggaagtc     360
gatacagcct ctagacataa aggtgtcaaa aaagttatca ttactgctcc atcaaagacc     420
gcgccaatgt acgtctatgg tgttaaccac gttaaataca cccattgac ggatcacgtg      480 gtctctaatg cctcctgtac taccaactgt ttggctccgt tggttaaggc tttggacgat     540
gagttcggta tcgaagaagc cttgatgaca actattcatg caactactgc ttctcaaaag     600
actgtcgatg gtaccagttc tggtggtaag gactggagag gcggtagatc ttgccaggga     660
aatatcattc cttcatctac tggtgcagct aaggctgtag gaaaatcttt gcctgaactt     720
aatggtaaga tcaccggtat gtctataaga gtcccaacaa ttaatatttc cctggttgac     780
ttgacattcc gtacagcaaa gaaaacttct tacgatgaca ttatgaaggc cctagaacaa     840
agatctcgca gcgatatgaa gggtgttttg ggtgttacca agacgccgt tgtgtcctct      900 gacttcacat ccgattcacg ttcatctatt gttgatgcca aggccggtat tgaattgaac     960
gaccattttt tcaaggtcct ttcttggtat gataatgaat atggttactc ttcaagagtg    1020
```
gttgatttat ccattttcat ggctcaaaag gacttcgaag ctggtgttta a          1071

<210> SEQ ID NO 48
<211> LENGTH: 356
<212> TYPE: PRT
<213> ORGANISM: Kluyveromyces lactis

<400> SEQUENCE: 48

Met Pro Asp Met Thr Asn Glu Ser Ser Lys Pro Ala Gln Ile Asn
1               5                   10                  15

Ile Gly Ile Asn Gly Phe Gly Arg Ile Gly Arg Leu Val Leu Arg Ala
            20                  25                  30

Ala Leu Thr His Pro Glu Val Lys Val Arg Leu Ile Asn Asn Pro Ser
            35                  40                  45

Thr Thr Pro Glu Tyr Ala Ala Tyr Leu Phe Lys Tyr Asp Ser Thr His
    50                  55                  60

Gly Lys Tyr Arg Gly Glu Val Glu Phe Asp Asp Glu Arg Ile Ile Ile
65                  70                  75                  80

Gln Asn Asp His Val Ser Ala His Ile Pro Leu Ser His Phe Arg Glu
                85                  90                  95

Pro Glu Arg Ile Pro Trp Ala Ser Tyr Asn Val Asp Tyr Val Ile Asp
            100                 105                 110

Ser Thr Gly Val Phe Lys Glu Val Asp Thr Ala Ser Arg His Lys Gly
            115                 120                 125

Val Lys Lys Val Ile Ile Thr Ala Pro Ser Lys Thr Ala Pro Met Tyr
130                 135                 140

Val Tyr Gly Val Asn His Val Lys Tyr Asn Pro Leu Thr Asp His Val
145                 150                 155                 160

Val Ser Asn Ala Ser Cys Thr Thr Asn Cys Leu Ala Pro Leu Val Lys
                165                 170                 175

Ala Leu Asp Asp Glu Phe Gly Ile Glu Glu Ala Leu Met Thr Thr Ile
            180                 185                 190

His Ala Thr Thr Ala Ser Gln Lys Thr Val Asp Gly Thr Ser Ser Gly
            195                 200                 205

Gly Lys Asp Trp Arg Gly Gly Arg Ser Cys Gln Gly Asn Ile Ile Pro
    210                 215                 220

Ser Ser Thr Gly Ala Ala Lys Ala Val Gly Lys Ile Leu Pro Glu Leu
225                 230                 235                 240

Asn Gly Lys Ile Thr Gly Met Ser Ile Arg Val Pro Thr Ile Asn Ile
                245                 250                 255

Ser Leu Val Asp Leu Thr Phe Arg Thr Ala Lys Lys Thr Ser Tyr Asp
            260                 265                 270

Asp Ile Met Lys Ala Leu Glu Gln Arg Ser Arg Ser Asp Met Lys Gly
            275                 280                 285

Val Leu Gly Val Thr Lys Asp Ala Val Val Ser Ser Phe Thr Ser
    290                 295                 300

Asp Ser Arg Ser Ser Ile Val Asp Ala Lys Ala Gly Ile Glu Leu Asn
305                 310                 315                 320

Asp His Phe Phe Lys Val Leu Ser Trp Tyr Asp Asn Glu Tyr Gly Tyr
                325                 330                 335

Ser Ser Arg Val Val Asp Leu Ser Ile Phe Met Ala Gln Lys Asp Phe
            340                 345                 350

Glu Ala Gly Val
        355

<210> SEQ ID NO 49
<211> LENGTH: 1023
<212> TYPE: DNA
<213> ORGANISM: Bacillus subtilis

<400> SEQUENCE: 49

```
atgaaggtaa aagtagcgat caacgggttt ggaagaatcg gaagaatggt ttttagaaaa     60
gcgatgttag acgatcaaat tcaagtagtg gccattaacg ccagctattc cgcagaaacg    120
ctggctcatt taataaagta tgacacaatt cacggcagat acgacaaaga ggttgtggct    180
ggtgaagata gcctgatcgt aaatggaaag aaagtgcttt tgttaaacag ccgtgatcca    240
aaacagctgc cttggcggga atatgatatt gacatagtcg tcgaagcaac agggaagttt    300
aatgctaaag ataaagcgat gggccatata gaagcaggtg caaaaaaagt gattttgacc    360
gctccgggaa aaatgaaga cgttaccatt gtgatgggcg taaatgagga ccaattcgac    420
gctgagcgcc atgtcattat ttcaaatgcg tcatgcacga caaattgcct tgcgcctgtt    480
gtaaaagtgc tggatgaaga gtttggcatt gagagcggtc tgatgactac agttcatgcg    540
tatacgaatg accaaaaaaa tattgataac ccgcacaaag atttgcgccg ggcgcgggct    600
tgcggtgaat ccatcattcc aacaacaaca ggagcggcaa aggcgctttc gcttgtgctg    660
ccgcatctga aggaaaaact tcacggcctc gccttgcgtg tccctgttcc gaacgtctca    720
ttggttgatc tcgttgttga tctgaaaacg gatgttacgg ctgaagaagt aaacgaggca    780
tttaaacgcg ctgccaaaac gtcgatgtac ggtgtacttg attactcaga tgaaccgctc    840
gtttcgactg attataatac gaatccgcat tcagcggtca ttgacgggct acaacaatg    900
gtaatggaag acaggaaagt aaaggtgctg gcgtggtatg acaacgaatg gggctactcc    960
tgcagagttg ttgatctaat ccgccatgta gcggcacgaa tgaaacatcc gtctgctgta   1020
taa                                                                1023
```

<210> SEQ ID NO 50
<211> LENGTH: 340
<212> TYPE: PRT
<213> ORGANISM: Bacillus subtilis

<400> SEQUENCE: 50

Met Lys Val Lys Val Ala Ile Asn Gly Phe Gly Arg Ile Gly Arg Met
1               5                   10                  15

Val Phe Arg Lys Ala Met Leu Asp Asp Gln Ile Gln Val Val Ala Ile
            20                  25                  30

Asn Ala Ser Tyr Ser Ala Glu Thr Leu Ala His Leu Ile Lys Tyr Asp
        35                  40                  45

Thr Ile His Gly Arg Tyr Asp Lys Glu Val Val Ala Gly Glu Asp Ser
    50                  55                  60

Leu Ile Val Asn Gly Lys Lys Val Leu Leu Asn Ser Arg Asp Pro
65                  70                  75                  80

Lys Gln Leu Pro Trp Arg Glu Tyr Asp Ile Asp Ile Val Val Glu Ala
                85                  90                  95

Thr Gly Lys Phe Asn Ala Lys Asp Lys Ala Met Gly His Ile Glu Ala
            100                 105                 110

Gly Ala Lys Lys Val Ile Leu Thr Ala Pro Gly Lys Asn Glu Asp Val
        115                 120                 125

Thr Ile Val Met Gly Val Asn Glu Asp Gln Phe Asp Ala Glu Arg His
    130                 135                 140

Val Ile Ile Ser Asn Ala Ser Cys Thr Thr Asn Cys Leu Ala Pro Val

```
145                 150                 155                 160
Val Lys Val Leu Asp Glu Glu Phe Gly Ile Glu Ser Gly Leu Met Thr
                165                 170                 175
Thr Val His Ala Tyr Thr Asn Asp Gln Lys Asn Ile Asp Asn Pro His
            180                 185                 190
Lys Asp Leu Arg Arg Ala Arg Ala Cys Gly Glu Ser Ile Ile Pro Thr
        195                 200                 205
Thr Thr Gly Ala Ala Lys Ala Leu Ser Leu Val Leu Pro His Leu Lys
    210                 215                 220
Gly Lys Leu His Gly Leu Ala Leu Arg Val Pro Val Pro Asn Val Ser
225                 230                 235                 240
Leu Val Asp Leu Val Val Asp Leu Lys Thr Asp Val Thr Ala Glu Glu
                245                 250                 255
Val Asn Glu Ala Phe Lys Arg Ala Ala Lys Thr Ser Met Tyr Gly Val
            260                 265                 270
Leu Asp Tyr Ser Asp Glu Pro Leu Val Ser Thr Asp Tyr Asn Thr Asn
        275                 280                 285
Pro His Ser Ala Val Ile Asp Gly Leu Thr Thr Met Val Met Glu Asp
    290                 295                 300
Arg Lys Val Lys Val Leu Ala Trp Tyr Asp Asn Glu Trp Gly Tyr Ser
305                 310                 315                 320
Cys Arg Val Val Asp Leu Ile Arg His Val Ala Ala Arg Met Lys His
                325                 330                 335
Pro Ser Ala Val
            340
```